(12) United States Patent
Melin et al.

(10) Patent No.: US 11,673,137 B2
(45) Date of Patent: Jun. 13, 2023

(54) SAMPLE HOLDER

(71) Applicant: Q-LINEA AB, Uppsala (SE)

(72) Inventors: Jonas Melin, Uppsala (SE); Simon Uhrberg, Uppsala (SE); Jonas Jarvius, Uppsala (SE)

(73) Assignee: Q-LINEA AB, Uppsala (SE)

( * ) Notice: Subject to any disclaimer, the term of this patent is extended or adjusted under 35 U.S.C. 154(b) by 307 days.

(21) Appl. No.: 16/963,427

(22) PCT Filed: Jan. 22, 2019

(86) PCT No.: PCT/EP2019/051526
§ 371 (c)(1),
(2) Date: Jul. 20, 2020

(87) PCT Pub. No.: WO2019/141875
PCT Pub. Date: Jul. 25, 2019

(65) Prior Publication Data
US 2021/0094035 A1    Apr. 1, 2021

(30) Foreign Application Priority Data

Jan. 22, 2018 (GB) ..................................... 1801019
Apr. 20, 2018 (GB) ..................................... 1806504

(51) Int. Cl.
*C12N 15/10* (2006.01)
*B01L 3/00* (2006.01)
(Continued)

(52) U.S. Cl.
CPC ... *B01L 3/502715* (2013.01); *B01L 3/502707* (2013.01); *B01L 3/502723* (2013.01);
(Continued)

(58) Field of Classification Search
CPC ......... B01L 3/502715; B01L 3/502707; B01L 3/502723; B01L 9/00; B01L 2200/027;
(Continued)

(56) References Cited

U.S. PATENT DOCUMENTS 5,248,479 A    9/1993  Parsons et al.
8,133,741 B2   3/2012  Potyrailo et al.
(Continued)

FOREIGN PATENT DOCUMENTS

CN         1250522        4/2000
CN       101297189       10/2008
(Continued)

OTHER PUBLICATIONS

International Search Report and Written Opinion of the International Searching Authority, dated Mar. 28, 2018 in corresponding International Patent Application No. PCT/EP2019/051526.
(Continued)

*Primary Examiner* — Jennifer Wecker
*Assistant Examiner* — Oyeleye Alexander Alabi
(74) *Attorney, Agent, or Firm* — Wenderoth, Lind & Ponack, L.L.P.

(57) ABSTRACT

A sample holder (10) comprises a sample chamber (33), a gas reservoir (32) and an upper layer (20) covering over the sample chamber (33) and gas reservoir (32), wherein a bottom surface of the upper layer (20) comprises a microstructure array (23) which overlies at least a portion of a top periphery of the sample chamber (33), and wherein the microstructure array (23) is in communication with a gas path which extends to the gas reservoir (32), to allow gas exchange between the sample chamber (33) and the gas reservoir (32).

25 Claims, 22 Drawing Sheets

(51) Int. Cl.
*B01L 7/00* (2006.01)
*F28F 3/12* (2006.01)
*B01L 9/00* (2006.01)
*C12M 3/06* (2006.01)
*C12M 1/00* (2006.01)
*C12M 1/34* (2006.01)
*C12Q 1/18* (2006.01)
*G01N 21/03* (2006.01)

(52) U.S. Cl.
CPC .............. *B01L 9/00* (2013.01); *C12M 23/16* (2013.01); *C12M 23/26* (2013.01); *C12M 41/00* (2013.01); *C12Q 1/18* (2013.01); *G01N 21/03* (2013.01); *B01L 2200/027* (2013.01); *B01L 2200/0684* (2013.01); *B01L 2300/041* (2013.01); *B01L 2300/047* (2013.01); *B01L 2300/048* (2013.01); *B01L 2300/06* (2013.01); *B01L 2300/0609* (2013.01); *B01L 2300/0819* (2013.01); *B01L 2300/0861* (2013.01); *B01L 2300/123* (2013.01); *B01L 2300/161* (2013.01); *B01L 2300/165* (2013.01); *B01L 2300/168* (2013.01); *B01L 2400/088* (2013.01); *G01N 2021/035* (2013.01)

(58) Field of Classification Search
CPC ....... B01L 2200/0684; B01L 2300/041; B01L 2300/047; B01L 2300/048; B01L 2300/06; B01L 2300/0609; B01L 2300/0819; B01L 2300/0861; B01L 2300/165; B01L 2400/088; C12M 23/16; C12M 23/26; C12M 41/00; C12Q 1/18; G01N 2021/035
See application file for complete search history.

(56) References Cited

U.S. PATENT DOCUMENTS

| | | |
|---|---|---|
| 2002/0098114 A1 | 7/2002 | Harding et al. |
| 2003/0031593 A1 | 2/2003 | Okubo et al. |
| 2004/0067166 A1 | 4/2004 | Karinka et al. |
| 2005/0084422 A1 | 4/2005 | Kido et al. |
| 2005/0271560 A1 | 12/2005 | Rodgers et al. |
| 2006/0078873 A1 | 4/2006 | Ogawa et al. |
| 2006/0288762 A1 | 12/2006 | Harding et al. |
| 2008/0176272 A1* | 7/2008 | Bergman .......... B01L 3/502761 435/283.1 |
| 2008/0257754 A1 | 10/2008 | Pugia et al. |
| 2009/0053106 A1 | 2/2009 | Wu et al. |
| 2009/0092975 A1 | 4/2009 | Stratford |
| 2009/0148912 A1 | 6/2009 | Takagi |
| 2010/0178208 A1 | 7/2010 | Xiao et al. |
| 2011/0053785 A1 | 3/2011 | Bedingham et al. |
| 2012/0040470 A1 | 2/2012 | Dorn et al. |
| 2013/0309679 A1 | 11/2013 | Ismagilov et al. |
| 2014/0079563 A1 | 3/2014 | Yang et al. |
| 2014/0141438 A1* | 5/2014 | Song ................. B01L 3/502784 435/6.12 |
| 2015/0031587 A1 | 1/2015 | Takagi |
| 2015/0093838 A1 | 4/2015 | Landers et al. |
| 2015/0204785 A1 | 7/2015 | Kim et al. |
| 2016/0016166 A1 | 1/2016 | Rolland et al. |
| 2019/0331906 A1* | 10/2019 | Jarvius ............... G01N 21/6452 |

FOREIGN PATENT DOCUMENTS

| | | |
|---|---|---|
| CN | 101598727 | 12/2009 |
| CN | 102387863 | 3/2012 |
| CN | 104144748 | 11/2014 |
| CN | 104428651 | 3/2015 |
| CN | 104620113 | 5/2015 |
| CN | 204710358 | 10/2015 |
| EP | 1 707 267 | 10/2006 |
| EP | 1 977 829 | 10/2008 |
| KR | 10-2018-0005090 | 1/2018 |
| WO | 95/06508 | 3/1995 |
| WO | 03/052428 | 6/2003 |
| WO | 2007/025558 | 3/2007 |
| WO | 2014/108185 | 7/2014 |
| WO | 2014/111928 | 7/2014 |
| WO | 2017/216310 | 12/2017 |
| WO | 2017/216312 | 12/2017 |
| WO | 2017/216314 | 12/2017 |
| WO | 2018/150414 | 8/2018 |

OTHER PUBLICATIONS

UK Search Report, dated Jul. 23, 2018 in corresponding GB patent application No. GB1801019.9.
UK Search Report, dated Jul. 17, 2018 in corresponding GB patent application No. GB1801019.9.
UK Search Report, dated Jul. 24, 2018 in corresponding GB patent application No. GB1801019.9.
International Search Report and Written Opinon of the Searching Authority dated Apr. 1, 2019 in International (PCT) Application No. PCT/EP2019/051527.
Notice of Allowance dated Jul. 6, 2022 in Chinese Application No. 201980009744.0 with English translation.
Notice of Allowance dated Jul. 6, 2022 in Chinese Application No. 201980009748.9 with English translation.
Yue, Rui-feng et al., "Study on Dispenser of Liquid Droplets Based on Electrowetting-on-Dielectric", Chinese Journal of Electron Devices, Feb. 2007, vol. 30, No. 1, pp. 41-45 (with English absuact).
Wu, Jian-gang et al., "Fabrication of Super-Hydrophobic Surfaces for Microfluidic Chips", Microfabrication Technology, Jun. 2006, No. 3, pp. 36-39 (with English abstract).

* cited by examiner

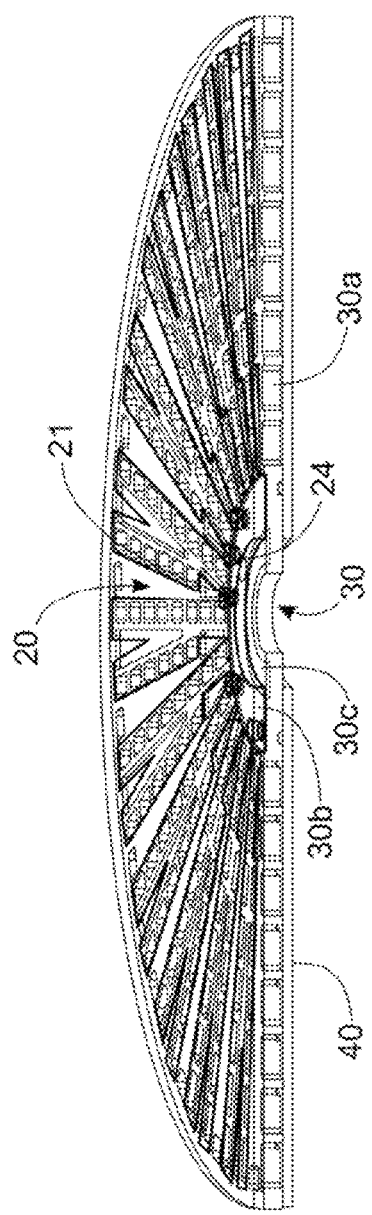
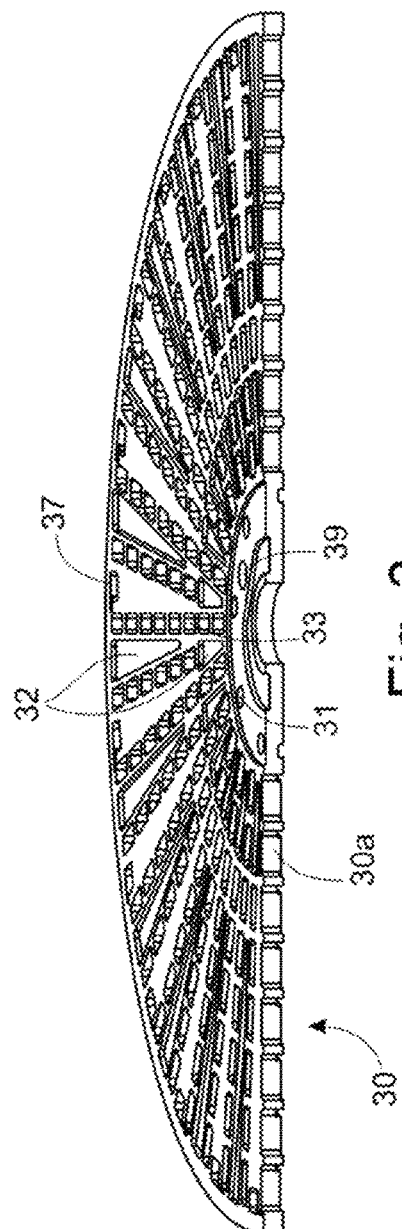
Fig. 2
Fig. 3

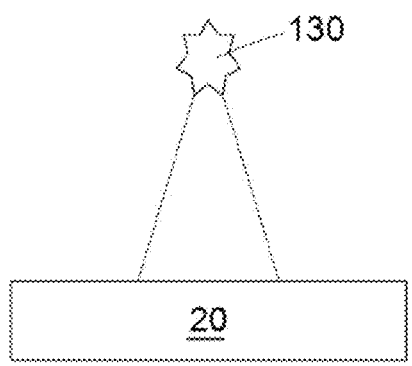
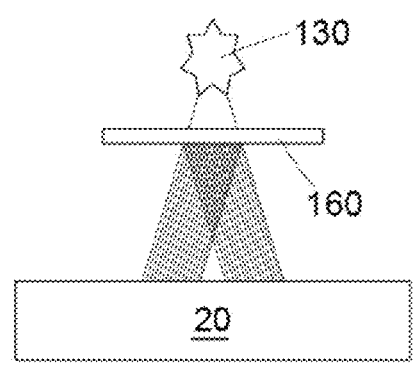
Fig. 26A  Fig. 26B
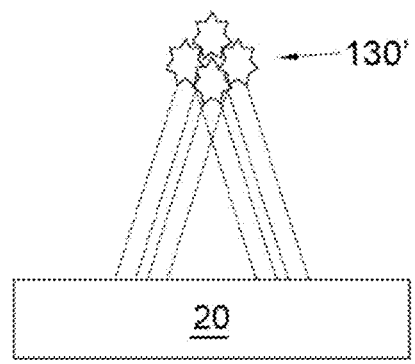
Fig. 26C

SAMPLE HOLDER

The present invention relates to sample holders for use in analysis of samples. In some examples the analysis of samples involves the detection of the presence, amount, and/or absence of microscopic objects in the sample, such as microscopic biological objects.

It is important in various fields to be able to analyse samples quickly and efficiently and in particular to be able to detect and/or count small objects such as bioparticles, molecules, cells and so on. However, there remains a need to further improve on the capabilities of sample holders for use in this field.

According to a first aspect, the invention provides a sample holder comprising:
an upper layer;
a lower layer;
a middle layer between the upper and lower layers; and
a sample chamber formed by a through-hole in the middle layer, covered at its upper extent by a portion of the bottom surface of the upper layer, and at its lower extent by a portion of the top surface of the lower layer,
wherein at least part of the bottom surface of the upper layer overlapping a portion of a top periphery of the sample chamber comprises a hydrophobic surface,
and wherein a contact angle of a water droplet on the hydrophobic surface exceeds 110°.

Thus, references to the "hydrophobic surface" herein refer to a hydrophobic surface for which the contact angle of a water droplet on the surface exceeds 110°. Optionally, the contact angle exceeds 120°. The contact angle may lie between 120° and 140°, or may exceed 140°, or may exceed 150° (in which case the surface is superhydrophobic).

The hydrophobic surface may be amphiphobic, meaning that as well as being hydrophobic, the surface is oleophobic. In such a case, the contact angle of an oil droplet on the amphiphobic surface may exceed 110°. Optionally, the contact angle exceeds 120°. The contact angle may lie between 120° and 140°, or may exceed 140°, or may exceed 150°.

In cases where the contact angle of a water droplet on the surface exceeds 150°, and the contact angle of an oil droplet on the surface exceeds 150°, the surface is deemed superamphiphobic.

In the following discussion, references to a "hydrophobic surface" should be understood as covering "amphiphobic surfaces" (except in the case that surfaces which are hydrophobic but not amphiphobic are explicitly discussed), since an amphiphobic surface is a special case of a hydrophobic surface. An amphiphobic surface is by definition also hydrophobic, but a hydrophobic surface is not necessarily amphiphobic.

Accordingly, the sample chamber is bounded at least in part at its upper periphery by a hydrophobic surface. The term "top periphery", herein refers to the edges which bound the top surface of the sample chamber. The hydrophobic surface may extend around the entire top periphery of the sample chamber, or around just part of this periphery. In terms of its extent within the periphery of the sample chamber (and implying no limitation on the extent of the hydrophobic surface outwardly of the periphery of the sample chamber) the hydrophobic surface may extend only around the periphery (or part thereof), or may extend also across part or a whole of the entire upper surface of the sample chamber. The hydrophobic surface may extend outwardly of the periphery of the sample chamber.

Due to the hydrophobic nature of the surface overlying at least part of the top periphery of the sample chamber, that surface cannot be wetted when a sample liquid is introduced into the sample chambers. As a result, the hydrophobic surface acts to seal the sample in the sample chamber.

The sample chamber may comprise an opening, optionally at its bottom periphery, allowing a liquid sample to be supplied into the sample chamber.

The sample chamber may be sealed with respect to outward liquid flow at its top and bottom peripheries, where the middle layer meets the upper layer and lower layer, respectively.

At the bottom periphery, the sample chamber is optionally sealed to liquid egress by a bonding pattern which joins the middle layer to the lower layer.

At the top periphery, the sample chamber is optionally sealed to liquid egress by the hydrophobic surface, or partially by the hydrophobic surface and partially by a bonding pattern which joins the middle layer to the upper layer. Where "a bonding pattern which joins the middle layer to the upper layer" is referred to, it will be appreciated that the bonds may exist only outside of any structures which form a hole which is open at the top surface of the middle layer.

In some embodiments, the hydrophobic surface overlaps with only one top edge (or part thereof) of the sample chamber. In that case, the sample chamber may be sealed at the remaining top edges using a bonding pattern to avoid leakage of liquid along those edges. A continuous bond around a sample chamber between the upper layer and middle layer may not be necessary in the regions where the upper layer comprises a hydrophobic surface.

The sample chamber may be a blind hole to the sample liquid, that is, though there may be an opening for the sample liquid into the sample chamber, there may be no outlet for the sample liquid.

Optionally, the sample holder comprises a plurality of sample chambers, as described above.

Optionally, the entire bottom surface of the upper layer comprises a hydrophobic surface.

Optionally, the hydrophobic surface is formed from a microstructure array. Herein, a microstructure array comprises a plurality of microstructures formed in or on the surface. The microstructures may be distributed in a regular arrangement, for example with even spaces between neighbouring microstructures.

Optionally, a plurality of discrete (i.e. at least partially spatially separated) microstructure arrays may be provided. Each microstructure array may extend over a plurality of sample chambers. Each microstructure array may have a width slightly wider than the width of the sample chambers.

For example, in embodiments where the sample holder comprises a plurality of sample chambers located along radial lines of the sample holder, a plurality of radially-extending microstructure arrays may be provided, each broadly aligned with a radial line of sample chambers (for example, the sample chambers within one fluidic network, as discussed below). In a further alternative, a plurality of microstructure arrays may be provided, each being formed as a concentric circle overlying a plurality of sample chambers arranged in a concentric circle (wherein the sample chambers may belong to different fluidic networks, for example).

Rather than a plurality of discrete microstructure arrays, a single continuous microstructure array may be provided. For example, the single, continuous microstructure array may cover essentially the entire bottom surface of the upper layer. Alternatively, in embodiments where the sample holder comprises a plurality of sample chambers located along radial lines of the sample holder, a microstructure array comprising a plurality of radially-extending microstructure "lobes" may be provided, each lobe broadly aligned with a radial line of sample chambers.

Other configurations of microstructure arrays are of course possible.

The microstructure arrays may have a shape facilitating alignment with the sample chambers below, during manufacture of the sample holder. For example, one or more of the microstructure arrays may comprise a narrowed portion (optionally a plurality of narrowed portions) at which the width of the microstructure array is narrowed to be only slightly wider than the width of a sample chamber. The narrowed portion may be provided at a position radially along the microstructure array to align with an outermost sample chamber, for example. All the microstructure arrays, or only one, or some number in between (for example, half of the microstructure arrays, with the narrowed portions provided on alternate microstructure arrays) may have the narrowed portion. The narrowed portions may then visually be rotationally aligned with the outermost sample chambers, for example, prior to bonding.

Where a bond is present between an area of the microstructure array (on the upper layer) and the middle layer, optionally only the tips of the microstructures forming the microstructure array are bonded to the middle layer, to maintain the spacing between the microstructures.

The microstructures may have a height of 25 to 150 µm (for example, approximately 50 µm, or 100 µm).

The microstructures may have a width of 50 to 150 µm.

In some embodiments, the microstructures may be extended structures having a length that is longer than their width. In such embodiments, the microstructures have a rib-like structure (microribs). The microstructures may alternatively be described as ridge-like (microridges). For example, the microstructure array may comprise rectangular microstructures having a height of 25 to 150 µm, a width of 50 to 150 µm and a length of 50 to 20000 µm.

In embodiments where such microribs/microridges are provided, the lengths of the microribs/microridges are optionally orientated at an angle (for example, broadly perpendicular, and not parallel) to the top edge of the sample chamber which they overlie, such that the spaces between adjacent microribs/microridges open into the sample chamber.

In other embodiments, the microstructures may comprise pillar-like formations, having a length comparable to their width, for example. Thus, the microstructure array may comprise micropillars, forming a micropillar array.

The micropillars may have a height of 25 to 150 µm, a width of 50 to 150 µm and a length of 50 to 150 µm.

The micropillars may have a centre-to-centre distance between two adjacent micropillars of 50 to 150 µm (for example, approximately 100 µm).

Optionally, the ratio of the height of the micropillars to the centre-to-centre distance is approximately 1:1.

The micropillars may have a broadly frustoconical shape (i.e. having a circular cross-section and tapering diameter along the axis of the micropillars, with the diameter being a maximum at the upper end (i.e. at the base, furthest from the sample chamber), and a minimum at the lower end (i.e. at the tip, closest to the sample chamber, at the boundary between the upper layer and the middle layer). The tips of the micropillars optionally have a diameter of approximately 50 µm, and the bases of the micropillars optionally have a diameter of approximately 75 µm. The micropillars optionally have a height of approximately 50 µm. The centre-to-centre distance is optionally approximately 100 µm, and so at the base there is therefore a 25 µm gap between the micropillars.

Optionally, the microstructures are tapered. That is, the microstructures may have a cross sectional area which is a maximum at the upper end (i.e. at the base, furthest from the sample chamber), and a minimum at the lower end (i.e. at the tip, closest to the sample chamber, at the boundary between the upper layer and the middle layer). Such tapered microstructures are easier to form by injection moulding, compared to untapered microstructures (i.e. microstructures having an unvarying cross-section).

The tips of the microstructures (i.e. the ends which abut the middle layer) may be flat, and parallel to the plane of the upper surface of the middle layer. This aids a good interface between the microstructure array and middle layer.

Optionally, the height of the microstructures is similar to, or less than the minimum diameter or width of the microstructures.

Optionally, the distance between adjacent microstructures at their base is 10 µm to 50 µm, for example 25 µm.

Optionally, the gas volume in the microstructure array is 20% to 60% (optionally 30 to 50%) of the total volume of the area covered by microstructures.

The lower limits on the size of the microstructures and the separation distance may be set by the limits for injection moulding. The upper limits on the size of the microstructures and the separation distance may be set based on the requirement that the surface has the property of being hydrophobic. In particular, the microstructures may have characteristics which are chosen so as to prevent the liquid that bridges the tips of the microstructures from touching the base of the microstructures. This is dependent on several parameters, for example, the surface area of the microstructure tip, the separation distance of the microstructures, the height of the microstructures and the contact angle of liquid with the material from which the microstructures are formed, etc.

The size and separation distance of the microstructures is not particularly limited, as long as the hydrophobic property is achieved.

The shape of the cross-section of the microstructures is not particularly limited, as long as the hydrophobic property is achieved. The microstructures may for example have a circular, oval, elliptical, triangular, square, rectangular, pentagonal or hexagonal cross-section, or any other regular or irregular polygonal shape.

The microstructures may have the shape of a truncated pyramid, for example having triangular, square, rectangular, pentagonal or hexagonal base faces.

The microstructure array may be formed by injection moulding, etching or stamping, for example.

Optionally, the microstructure array is formed from a hydrophobic material.

The foregoing discussion is generally applicable for forming a hydrophobic surface, but the formed surface may not also be oleophobic (i.e. the surface may not be amphiphobic).

Where an amphiphobic surface is provided, this is may be formed from a microstructure array similar to that discussed above, modified (for example, mechanically or chemically) to make the microstructure array amphiphobic.

In order to make an amphiphobic surface, in one embodiment a microstructure array similar to that set out above is mechanically modified to provide "overhanging" microstructures. This may be done by producing microstructures (for example, micropillars) as described above, and then compressing the microstructures (micropillars). This may be achieved by simultaneously heating and compressing the microstructures (micropillars).

The distance between the uncompressed microstructures (micropillars) can be chosen in consideration of the size of the overhang that should be obtained.

The microstructure has a width W, and the overhang projects over this width by an overhang width w. The value of w may be from 0.25 to 1.5 times the width W of the microstructure. The total width W' of the compressed microstructures (W+2 w) may then be in the range of 1.5 W to 4 W.

For example, if W is 50 μm, w may be from 12.5 μm to 75 μm, giving W' as being from 75 μm to 200 μm.

The tips of the compressed overhanging microstructures optionally do not contact each other.

As an alternative to using mechanical means to modify the microstructure array, the surface chemistry of the microstructure array may be modified to provide an amphiphobic surface. Such methods of chemical modification are known in the art, and are not discussed in further detail here.

The form of the amphiphobic surface and the method used to produce it is not limited by the foregoing discussion; any form of microstructure array which provides the amphiphobic property may be provided, and any method known in the art may be used to produce the amphiphobic microstructure array.

In advantageous embodiments, the microstructure array and upper layer form a unitary structure. In alternative embodiments, the microstructure array and upper layer are non-unitary, such that the microstructure array and a main body of the upper layer are formed separately and joined together.

The microstructure array may act to form a gas film above the sample chamber(s), whereby gas is able to flow laterally out of (and into) the sample chamber(s). Gas may flow laterally through the sample holder through the spaces between the microstructures. The microstructure array therefore provides a means for evacuating gas (for example, air) from the sample chamber(s), as the, or each, sample chamber is filled with a sample liquid.

The sample holder may comprise a gas reservoir. The gas reservoir may be primarily defined in the middle layer. That is, the shape and lateral extent of the gas reservoir may be defined within the middle layer. The upper surface of the gas reservoir may be bounded by the upper layer. The bottom surface of the gas reservoir may be bounded by the lower layer (in embodiments where the gas reservoir is a through-hole through the middle layer), or may be bounded by the middle layer (in embodiments where the gas reservoir is a blind hole in the middle layer, meaning that the gas reservoir is not a through-hole through the middle-layer).

The gas film formed in the microstructure array may provide a connection between the sample chamber(s) and the gas reservoir, and thus, the gas film advantageously provides a means for gas exchange between gas in the sample chamber, and gas in the gas reservoir.

The microstructure array may overlie the top periphery of the sample chamber at a first position, and may overlie at least a portion of a top periphery of the gas reservoir at a second position, and may extend between the first position and the second position, such that a gas path is formed by the microstructure array.

Alternatively, a gas path extending from the microstructure array to at least a portion of a top periphery of the gas reservoir may comprise a groove in the upper layer (for example, in the bottom surface of the upper layer) or middle layer (for example, in the top surface of the middle layer), which is not provided with microstructures.

The microstructure array may connect to, overlie or partly overlie one, or a plurality of, gas channels. The gas channels(s) may be formed in the upper surface of the middle layer (in which case, the microstructure array overlies or partly overlies the gas channel(s). Alternatively, the gas channels may comprise a groove in the upper layer (in which case, the microstructure array connects to the gas channel(s).

The gas channel(s) may run to a position where the gas channel(s) is/are open to the atmosphere. For example, the gas channel(s) may open into a gap which is open to the atmosphere. This gap may be provided between an inner periphery of the upper layer and an outer periphery of a raised section of the middle layer (described in detail below). The microstructure array may thereby be vented; gas (for example, air) can move from the microstructure array into the gas channels(s), along the gas channel(s) and into the gap, which is open to the atmosphere.

The gap may have a width of between 0.1 and 1 mm. The gap may have a width of, for example 0.15 to 0.5 mm, and optionally may have a width of 0.2 to 0.35 mm.

Where the microstructure array has a lobed shape, each lobe may overlie one, two, or more gas channels. Alternatively, only a sub-set (for example, every other neighbouring lobe) may overlie one, two or more gas channels.

Where a plurality of separate microstructure arrays are provided, each may overlap with a single gas channel, or a plurality thereof.

Each sample chamber may be connected via the gas film to one or more gas reservoirs.

The sample holder may comprise a gas vent (optionally formed as a through-hole in the upper layer). The sample holder may comprise a plurality of such vents. The, or each, vent may open directly into a gas reservoir, or may open into an area provided with a hydrophobic surface (for example, provided by a microstructure array), which is not above a gas reservoir. Gas may be able to flow from a gas reservoir and out of the gas vent via a portion of the microstructure array provided between the gas reservoir and the gas vent. Gas may be able to flow from a sample chamber and out of the gas vent via a portion of the microstructure array provided between the sample chamber and the gas vent.

Accordingly, the gas vent(s) may be provided through the upper layer in an area in which a hydrophobic surface (for example, provided by a microstructure array) is provided on the bottom surface of the upper layer. Accordingly, liquid cannot flow out of the gas vent(s), but gas may do so. The gas vent(s) may therefore not need to be sealed, but may simply be plain holes.

Optionally, the gas vent(s) is/are provided at an inner position on the sample holder (for example, at a radially inner position). This is advantageous in embodiments where sample inlet port(s) is/are also located at an inner position. Then, all the openings in the sample holder (inlets to and outlets from the sample holder) are located at an inner position. This allows the sample holder to be sealed, if necessary, for example by placing a sealing layer on top of all the openings.

In some embodiments, the/each gas vent may be covered with a gas-permeable membrane. In still further embodiments, the gas vent may comprise a valve. Where a valve is provided, this may be a one-way valve which allows for gas flow out of the sample holder, but not into the sample holder.

Optionally, the valve opens only under slight over pressure (as might be provided when filling the sample holder, for example).

The gas reservoir may contain air. The upper layer of the sample holder may comprise a gas vent, and the gas reservoir may be connected to the atmosphere (optionally via a portion of the microstructure array between the gas vent and the gas reservoir) via the gas vent.

In some embodiments, gas vents are not provided. In such a case, gas from the sample chamber(s) is evacuated to the gas reservoir as the sample chamber(s) is/are filled with liquid, causing an increase in the pressure in the gas reservoir. Gas is then not vented to the atmosphere from the sample holder.

The gas reservoir may comprise a specific gas or gas mixture, different from air, which may be selected so as to provide a particular analysis condition in one or more sample chambers. For example, the gas or gas mixture may not include oxygen, so as to provide anaerobic conditions within some or all of the sample chambers.

Optionally the sample holder comprises a plurality of gas reservoirs. The plurality of gas reservoirs may contain the same or different gases. Some or all of the gas reservoirs may contain air and may be connected to the atmosphere (for example, via a gas vent). Some or all of the gas reservoirs may contain a specific gas or gas mixture to provide a particular analysis condition in some or all of the sample chambers. For example, the gas or gas mixture may not include oxygen, so as to provide anaerobic conditions within some or all of the sample chambers. Such gas reservoirs may comprise a one-way valve which allows for gas flow out of the gas reservoir (for example, when the sample is supplied into the sample holder), but not into the gas reservoir. Alternatively, the gas reservoirs may not have a one-way valve (or any form of gas vent) allowing venting to the atmosphere; rather, pressure in the gas reservoir may simply increase as gas from the sample chamber(s) is evacuated to the gas reservoir as the sample chamber(s) is/are filled with liquid.

The sample holder may comprise a fluidic network comprising an inlet, a fluid filling channel, and a sample chamber connected to the fluid filling channel, wherein the fluid filling channel has a first end and a second end, the first end of the fluid filling channel being connected to the inlet.

The fluidic network may comprise a waste reservoir, and the second end of the fluid filling channel may be connected to the waste reservoir.

In some embodiments, the waste reservoir is a dedicated waste reservoir. Alternatively, the waste reservoir may be a gas reservoir. In use, only a partial volume of the gas reservoir may be filled with waste.

In some embodiments, there is no waste reservoir present in the fluidic network.

The sample holder may comprise a fluidic network comprising an inlet, a plurality of fluid filling channels, and a plurality of sample chambers connected to one (or optionally, more than one) of the plurality of fluid filling channels, wherein the plurality of fluid filling channels each have a first end and a second end, the first end of each of the plurality of fluid filling channels being connected to the inlet.

Optionally, each sample chamber is connected to only one or only two fluid filling channels.

The fluidic network may comprise a plurality of waste reservoirs, and the second end of each of the plurality of fluid filling channels may be connected to one of the plurality of waste reservoirs.

In some embodiments, the waste reservoirs are dedicated waste reservoirs. Alternatively, the waste reservoirs may be gas reservoirs. In use, only a partial volume of the gas reservoirs may be filled with waste.

The microstructure array optionally covers at least a portion of the top periphery of each sample chamber in the fluidic network, and may extend outwardly therefrom to an area over a gas reservoir, and/or to an area over a gas path connected to a gas reservoir, and/or an area beneath a gas vent, and/or an area over a waste reservoir, and/or an area over a venting channel connected to a waste reservoir. Gas exchange between all areas covered by the microstructure array is possible.

The sample holder may comprise a plurality of fluidic networks, in which case a corresponding plurality of separate microstructure arrays may be provided, and one microstructure array may serve one fluidic network. Alternatively, where a plurality of fluid filling channels are present within the fluidic network, there may be a plurality of separate microstructure arrays corresponding to the number of fluid filling channels, and each one of the plurality of microstructure arrays may serve one of the plurality of fluid filling channels.

In a further alternative, each microstructure array may serve a corresponding sample chamber from each fluidic network or fluid filling channel. For example, in embodiments where the sample holder comprises a plurality of sample chambers located along radial lines of the sample holder, a plurality of concentric circle microstructure arrays may be provided, each overlying (at least partially) a plurality of sample chambers arranged in a concentric circle.

The sample chambers arranged in a concentric circle may belong to different fluidic networks, and/or may be connected to different fluid filling channels, for example.

Several fluidic networks may have one or more gas reservoirs in common. Or, each fluidic network may have one or a plurality of dedicated gas reservoirs. Or, one or more fluidic networks may not have a corresponding gas reservoir.

A restriction to fluid flow may be provided at the second end of the fluid filling channel, for each of the plurality of fluid filling channels. Optionally, the restriction is a geometric restriction. Such a restriction may provide a geometric capillary burst valve. The restriction may be hydrophobic. This may be the case because the material in which the fluidic network is provided is hydrophobic, and the restriction may also be treated to make it more hydrophobic. If the material in which the fluidic network is provided is not hydrophobic, the restriction may be treated to make it hydrophobic.

The, or each, sample chamber is connected to at least one fluid filling channel, and optionally the opening into the sample chamber from the fluid filling channel lies at the bottom periphery of the sample chamber. Fluid entering the sample chamber therefore fills the sample chamber from the bottom up. This is particularly advantageous in embodiments in which the sample chamber(s) is/are provided with a substance (for example, a reagent) which has been deposited (for example, by lyophilisation) on the bottom of the sample chamber. On filling sample chamber, the sample fluid reconstitutes the deposited substance, and the sample fluid and substance mix together. Filling from the bottom allows the substance to be reconstituted and mix with the sample effectively.

Optionally, a branch channel branches off from each fluid filling channel, to connect the fluid filling channel to the, or a, respective, sample chamber.

Optionally, a plurality of branch channels branch off from each fluid filling channel, to connect the fluid filling channel to a respective plurality of sample chambers.

In some embodiments, such branch channels can be used to store a small amount of sample (once the sample has been introduced into the sample holder) which can be used to maintain the level of fluid in the sample chamber, in the event that some of the sample in the sample chamber evaporates during the analysis. Thus, the, or each, branch channel may be used as a sample top-up reservoir.

Each fluid filling channel may have an extra volume provided in the middle layer to allow for different fill volumes of the sample and to allow for some liquid evaporation without loss of liquid from the sample chambers. For example, if too much sample is supplied, excess sample may be contained by the extra volume. The extra volume may be a through-hole or blind hole (i.e. not a through-hole) in the middle layer. The extra volume may be located between the inlet and the point where the sample chamber nearest the inlet connects to the fluid filling channel.

Each fluid filling channel may be shaped so as to have the effect of partially separating the plurality of sample chambers connected to the fluid filling channel into sub-groups. For example, six sample chambers may be connected to one fluid filling channel, and these may be separated into two sub-groups of three. Eight sample chambers may be connected to one fluid filling channel, and these may be separated into two sub-groups of four. Seven sample chambers may be connected to one fluid filling channel, and these may be separated into two sub-groups, one of four and one of three. This may be useful, for example, in AST testing. For example, a first sub-group of the two may have a first antimicrobial agent deposited in each of the sample chambers in the first sub-group (at different concentrations in each sample chamber), and a second sub-group of the two may have a second antimicrobial agent (different from the first antimicrobial agent) deposited in each of the sample chambers in the second sub-group (at different concentrations in each sample chamber).

The sample chambers of the two sub-groups may all align along a radius of the sample holder.

Two or more sub-groups may be provided.

The fluid filling channel may separate the sub-groups by providing a long separation distance between the sub-groups, such that there is very low crosstalk between the two sub-groups.

One possible way of providing this separation is by providing a fluid filling channel which doubles back on itself. Such a fluid filling channel may have a hook shape. A first of the sub-groups may be connected (via respective branch channels) to an upstream part of the fluid filling channel, i.e. a part of the fluid filling channel running from the inlet to roughly mid-way along the extent of the middle layer along its radius. After the first sub group, the fluid filling channel may run (with no sample chamber connecting to it) towards the outer edge of the middle layer. Near the outer edge of the middle layer, the fluid filling channel may turn back on itself, and run back towards the centre of the middle layer, stopping slightly outwardly of the point at which it continued on from the first sub-group. The second sub-group may be distributed along this downstream return section, i.e. from the outer edge of the middle layer to the end of the fluid filling channel.

In use, a sample liquid may be supplied into the fluidic network via the inlet. Air present in the fluid filling channel(s), branch channel(s), and sample chamber(s) may be evacuated through the microstructure array (for example, into a gas reservoir and/or out of a gas vent to the atmosphere).

From the inlet, the sample may flow into the fluid filling channel(s), into the branch channel(s) and into the sample chamber(s).

When the sample front reaches the microstructure surface in a sample chamber it stops, as the hydrophobic surface constitutes a barrier to the sample liquid. Propagation of the sample liquid may instead continue in other parts of the fluidic network (for example, other sample chambers connected to the fluid filling channel may fill up). Where a geometric restriction is provided, the degree of the restriction to flow presented by the geometric restriction may be chosen to ensure that the liquid front stops at this position, as long as any sample chambers upstream of the geometric restriction remain to be filled. When all sample chambers upstream of the geometric restriction are full, excess sample may pass through the restriction and into the waste reservoir.

Where a geometric restriction is not provided, the degree of the restriction to flow presented by the fluid filling channel may be chosen to ensure that the liquid front does not pass into the waste reservoir, as long as any sample chambers in the fluidic network remain to be filled.

Following filling of the sample liquid into the sample holder, excess sample liquid in the fluid filling channels may be evacuated. That is, any sample liquid in the fluid filling channels may be displaced by an unreactive fluid (for example, air or oil, such as mineral oil). This may be achieved by docking a pipette filled with the unreactive fluid to the inlet and actuating the plunger, for example. The sample liquid in the fluid filling channels may then be pushed (for example, through the restriction) into the waste reservoir. As a result, each sample chamber (and associated branch channel) is isolated. Advantageously, the possibility of cross-contamination between sample chambers is greatly reduced.

The sample holder optionally comprises a plurality of fluidic networks, as described above. That is, there may be a plurality of inlets, wherein one or a plurality of fluid filling channels (and associated plurality of sample chambers) run between each of the plurality of inlets and corresponding waste reservoirs. Here, the, or each, fluid filling channel is connected to only one of the plurality of inlets. Such an embodiment is particularly suitable for filling by pipette, where a single pipette sequentially dispenses sample into each inlet, or multiple pipettes simultaneously dispense sample into the plurality of inlets.

In a modification to the foregoing embodiment, there is only one inlet, and all the fluid filling channels are connected to that inlet.

In some embodiments, a central inlet reservoir (optionally formed in the middle layer) is provided, and may be configured to receive sample via a single inlet. The sample holder may then be spun to fill the sample into the fluid filling channel(s), sample chamber(s) and waste reservoir(s) (where these are present) using centrifugal force. Unreactive fluid may be introduced into the fluid filling channels in the same way, to displace any sample liquid in the fluid filling channels (as discussed above).

The fluidic filling network(s) may be primarily defined in the middle layer. That is, the shapes and lateral extents of the structures forming the fluidic filling network(s) may be defined within the middle layer. Upper and/or lower surfaces of the structures may be bounded by the upper and/or lower layers, respectively, of the sample holder, or by the middle layer.

The waste reservoir(s) (where present) may be formed as a through-hole(s) in the middle layer. The fluid filling channels may be formed as grooves in the bottom surface of the middle layer. The branch channels may be formed as grooves in the bottom surface of the middle layer.

In addition to the structures described above, the sample holder may comprise other structures, for example, additional reservoirs. Such reservoirs may for example be for holding a substance (for example, a reagent, in dried, liquid or lyophilised form) for use in an analysis, for receiving a sample for carrying out a concentration determination analysis, or for forming glue traps (such glue traps being provided to receive excess glue in embodiments in which the layers are glued together). Such additional reservoirs may be primarily defined in the middle layer (for example as a through-hole in the middle layer).

The additional reservoirs may be separate from (i.e. they may have no fluidic connection to) the fluidic networks.

Each additional reservoir, for example those for receiving a sample for carrying out a concentration determination analysis, may be connected to a liquid waste channel (or a plurality thereof). The liquid waste channel may receive excess liquid filled into the additional reservoir, to allow for variability in the amount of liquid introduced into the additional reservoir.

The liquid waste channel may be connected to a sub-reservoir, in order to handle a larger amount of excess liquid.

The sub-reservoir may comprise a connection to a gas channel, to allow gas to be vented as liquid is introduced into the additional reservoir.

An exit from the additional reservoir into the liquid waste channel may be provided opposite to an entrance into the additional reservoir from an inlet channel.

The roof of the additional reservoir may slope from the side of the additional reservoir on which the entrance is provided, up towards the side of the additional reservoir on which the exit is provided. This helps prevent air being trapped in the additional reservoir.

In the sub-reservoir, the connections to the liquid waste channel and gas channel may be provided at opposite ends of the sub-reservoir.

The liquid waste channel and/or gas channel may be formed as open channels in the middle layer, any may be covered with a label to contain the fluids. The liquid waste channel and/or gas channel may be formed in a raised section of the middle layer, as described below.

The gas channel may be in communication with the atmosphere. The gas channel may run to a gap which is open to the atmosphere. The gap may be between the middle layer and the upper layer (i.e. a gap between the inner periphery of the upper layer, and the outer periphery of the raised section of the middle layer, described below).

The middle layer may comprise a central raised section. The inlets to the fluidic network(s) (and additional reservoirs, where these are provided) may be formed in this raised section.

The upper layer may comprise a hole which fits around (is received over) the raised section. A plurality of nodes may project outwardly from the outer periphery of the raised section. The hole in the upper layer may be sized to engage the nodes around the raised section of the middle layer, such that the upper layer and middle layer may be press-fit together and frictionally engaged. Once engaged in this way, the top surface of the upper layer and the top surface of the raised section of the middle layer may be co-planar. Except at the positions of the nodes, there may be a gap (open to the atmosphere) between the inner periphery of the upper layer (i.e. the periphery of the hole in the upper layer) and the outer periphery of the raised section. This gap has a venting function, as discussed above.

The raised section may be an annulus extending outward from a central hole in the middle layer. The hole in the upper layer may be a circular hole having a radius slightly larger (for example, 0.1 to 0.5 mm larger, optionally 0.1 to 0.2 mm larger) than the outer radius of the annulus. The gap is then an annular gap.

As well as the middle layer discussed above, the sample holder may comprise one or more additional layers between the upper layer and lower layer.

In particular, the sample holder may comprise a flexible membrane layer, and/or a magnetic metal layer. These layers may be located between the middle layer and the upper layer. The layers optionally do not extend over the entirety of the middle layer, but optionally only cover an inner portion (towards a radially inner area) of the middle layer. Optionally, the flexible membrane layer, and/or a magnetic metal layer do not extend over any sample chambers.

The magnetic layer may allow the sample holder to be moved or held in place using a magnet.

The metal layer may be the same thickness as the middle layer, and the top and bottom surfaces of the metal layer may be co-planar with the top and bottom surfaces of the middle layer, respectively. Alternatively, the metal layer may be thicker than the middle layer, such that it extends past the bottom surface of the middle layer (whilst remaining co-planar with the top-surface), to allow for easy alignment. Alternatively, the metal layer may have a thickness that is less than that of the middle layer, such that the metal layer in inset from the bottom surface of the middle layer, whilst remaining co-planar with the top surface.

The metal layer may be overmoulded with the middle layer.

The flexible membrane layer may comprise a hole(s) (for example a pinhole(s)) or slit(s) located in register with the sample inlet port(s) and inlet(s) below, to provide a self-closing seal for the sample inlet port(s)/inlet(s), as discussed above.

One flexible membrane layer may be provided to cover all of the sample inlet port(s) and inlet(s). Alternatively, a plurality of flexible membranes may be provided, each covering one sample inlet port/inlet (or covering a sub-set of the sample inlet port(s)/inlet(s)).

Where both the magnetic layer and flexible membrane layer are provided, optionally the two layers are concentric, with the flexible membrane layer covering an outer annular area, and the magnetic layer covering an inner annular area, which optionally does not overlap with the outer annular area, or only overlaps partially (so that the magnetic layer does not obstruct the inlet(s)).

The magnetic layer and/or flexible membrane layer may be located within a recessed portion (of conforming shape to the magnetic layer and/or flexible membrane layer) on the upper surface of a main body of the middle layer.

The upper layer may include a through-hole to provide a sample inlet port, allowing a sample to be provided to the inlet (in the middle layer). One or a plurality of such sample inlet ports may be provided (corresponding to the one or plurality of inlets). The, or each, sample inlet port may comprise a self-closing seal which may be openable to allow sample to be dispensed through the sample inlet port into the inlet (for example using a pipette). The self-closing seal may be configured to self-close once the means for introducing the sample (for example, the pipette) has been withdrawn from the sample inlet port, to prevent evaporation from the inlet. The self-closing seal may comprise a flexible membrane made of silicone or rubber or the like, which has a slit or slits cut into it. Alternatively, the self-closing seal may comprise a flexible membrane made of silicone or rubber or the like, which has a small hole (optionally a round hole) in it, or a plurality of such seals. The self-closing seal is optionally provided at the bottom of the sample inlet port (in the upper layer) above the inlet (in the middle layer).

The, or each, sample inlet port may comprise a docking guide. Particularly in the case that a sample is manually introduced into the sample holder by a human operator, it may be difficult to exactly locate the pipette (or other means to dispense the sample) in the sample inlet port. Provision of a docking guide may obviate this difficulty.

The docking guide may take the form that the sample inlet port has a funnel shape, such that the sample inlet port optionally widens at its upper end (i.e. the end at the upper surface of the upper layer), to provide a larger hole in the upper layer for the operator to aim at. The sample inlet port optionally tapers down to a minimum at its lower end (i.e. the end at the bottom surface of the upper layer).

Alternatively, or additionally, the docking guide may for example comprise a projection (for example, a funnel-shaped projection) extending upwards from the sample inlet port. The docking guide optionally widens at its upper end (i.e. the end furthest from the sample inlet port), to provide a larger target for the operator to aim at.

The middle layer may comprise an opaque material, optionally a dark-coloured (for example, black) opaque material. Advantageously, this feature provides optical isolation for each sample chamber. This ensures that, when an optical reading is taken from a sample chamber (for example, when the sample chamber is imaged), the reading is not affected by spurious signals from neighbouring sample chambers, or other structures in the middle layer.

The upper layer may be at least semi-transparent. Advantageously, this allows for the sample chambers to be illuminated from above. This may be particularly important in analyses which depend on imaging the samples in the sample holder.

The lower layer may be optically transparent to a wavelength(s) of light which is/are measured in the analysis which makes use of the sample holder. The lower layer may function as an optical window for analysis (for example, by imaging) of the sample in sample chambers.

The lower layer may have a thickness of 0.5 to 1.5 mm, and optionally has a thickness of approximately 1 mm.

The middle layer may have a thickness of 0.1 to 5 mm. In some embodiments, the middle layer may have a thickness of 0.1 to 0.5 mm, for example 0.2 to 0.4 mm. In other embodiments, the middle layer may have a thickness of 1 to 5 mm, for example, approximately 2 mm. In further embodiments, the middle layer may have a thickness of between 0.5 and 1 mm. The upper layer may have a thickness of 0.2 to 2 mm, and optionally has a thickness of approximately 1 mm.

The sample holder may comprise a computer-readable code (for example a barcode or QR code). Alternatively or additionally, the sample holder may comprise human-readable information. The computer-readable code and human-readable information may be provided together on a label, or each may be provided on a separate label. Alternatively, the computer-readable code and human-readable information may be printed, engraved, or otherwise affixed/made readable directly onto the sample holder.

Optionally, a label may cover all inlets into the sample holder (for example, inlets of fluidic ne until it is pierced by the pipette for sample introduction.

The sample holder may comprise polystyrene. In particular, the sample holder may comprise an upper, middle and lower layer each formed of polystyrene.

The sample holder may comprise a cyclo-olefin polymer such as Zeonor®. In particular, the sample holder may comprise an upper, middle and lower layer each formed of a cyclo-olefin polymer such as Zeonor®.

The layers may be formed by injection moulding each layer separately.

The middle layer may be joined to the upper layer in such a way as to control gas exchange within the sample holder (for example, to allow gas exchange with the atmosphere, or only with gases provided in certain gas reservoirs, for a selected number of sample chambers). This may allow different conditions to be applied in sample chambers in different portions of the sample holder. In particular, the two layers may be joined with a bonding pattern which isolates a portion or portions of the sample holder from other parts of the sample holder and/or from the atmosphere. For example, the bonding pattern may be used to isolate a certain portion of the sample holder from the atmosphere, so that gas exchange between sample chambers in the certain portion is only possible with gas reservoir(s) which is/are also isolated from the atmosphere. For example, a fluidic network and an associated gas reservoir may be isolated from the atmosphere. Using the bonding pattern in this way is a cheap and reproducible way of achieving controlled (i.e. selective) gas exchange within the sample holder.

The middle layer may be joined to the upper layer using a welding process (for example, laser welding, RF welding, ultrasonic welding), glue or solvent bonding, for example. The lower layer may be joined to the middle layer using the same process. Optionally, layers may be joined using laser welding. Optionally, layers may be joined by ultrasonic welding.

Any of the surfaces of the sample holder which come into contact with sample or any other fluid may be coated or otherwise treated to modify the surface properties. For example, the restriction(s) may be coated to provide a more hydrophobic section. The fluid filling channel(s) and/or branch channel(s) and/or sample chamber(s) may be coated to provide hydrophilic surfaces.

In the foregoing description, optional features of the first aspect have been described. It is noted that each optional feature may be combined with each other optional feature, except in cases where the features are mutually exclusive alternatives.

Moreover, each aspect set out herein may be combined with any other aspect.

According to a second aspect, the invention provides a sample holder comprising: a sample chamber, a gas reservoir, and a upper layer covering over the sample chamber and gas reservoir, wherein a bottom surface of the upper layer comprises a microstructure array which overlies at least a portion of a top periphery of the sample chamber, and wherein the microstructure array is in communication with a gas path which extends to the gas reservoir, to allow gas exchange between the sample chamber and gas reservoir.

The second aspect of the invention may comprise any of the optional features of the first aspect of the invention, and these may provide similar functions and/or advantages. Optional features may be combined with each other optional feature, except in cases where the features are mutually exclusive alternatives.

The microstructure array may extend around the entire top periphery of the sample chamber, or around just part of this periphery. In terms of its extent within the periphery of the sample chamber (and implying no limitation on the extent of the microstructure array outwardly of the periphery of the sample chamber) the microstructure array may extend only around the periphery (or part thereof), or may extend also across part or a whole of the entire upper surface of the sample chamber. The microstructure array may extend outwardly of the periphery of the sample chamber, for example to allow a gas connection between the sample chamber and a gas reservoir or a gas vent.

The microstructure array may overlie the top periphery of the sample chamber at a first position, and may overlie at least a portion of a top periphery of the gas reservoir at a second position, and may extend between the first position and the second position, such that the gas path is formed by the microstructure array.

Alternatively, the gas path may comprise a groove in the upper layer or middle layer, which is not provided with microstructures, extending from the microstructure array to at least a portion of a top periphery of the gas reservoir.

As described above in relation to the first aspect, the microstructure array may connect to, overlie or partly overlie one, or a plurality of, gas channels. The gas channels(s) may be formed in the top surface of the middle layer (in which case, the microstructure array overlies or partly overlies the gas channel(s). Alternatively, the gas channels may comprise a groove in the upper layer (in which case, the microstructure array connects to the gas channel(s).

The gas channel(s) may run to a position where the gas channel(s) is/are open to the atmosphere. For example, the gas channel(s) may open into a gap which is open to the atmosphere. This gap may be provided between an inner periphery of the upper layer and an outer periphery of a raised section of the middle layer (described in detail above). The microstructure array may thereby be vented; gas (for example, air) can move from the microstructure array into the gas channels(s), along the gas channel(s) and into the gap, which is open to the atmosphere.

The gap may have a width of between 0.1 and 1 mm. The gap may have a width of, for example 0.15 to 0.5 mm, and optionally may have a width of 0.2 to 0.35 mm.

The properties of the microstructure array may be as discussed above in reference to the optional features of the first aspect of the invention.

The sample holder may comprise a plurality of sample chambers, and/or a plurality of gas reservoirs.

Optionally, the microstructure array forms a hydrophobic surface, such that it is not possible for liquid in the sample chamber to escape via the gas path.

The composition of the sample liquid may affect the wetting properties of the sample liquid, and may further determine whether liquid permeates between the microstructures of the microstructure array.

In a sample liquid comprising predominantly water (where the influence of any oily or detergent-like molecules on the wetting properties of the sample liquid is negligible), the sample liquid may be in the Cassie state below the microstructure array. That is, the sample liquid lies beneath microstructure array with a layer of gas permeating between the microstructures of the microstructure array. Gas exchange may then be possible across the entire surface of the sample liquid, except that in contact with the microstructures of the microstructure array.

In some cases, the sample liquid may not have the same wetting properties as water. For example, the sample may include proteins which may affect the sample liquid much the same as if a detergent or oil were present. In such a case, and where the microstructure array forms a hydrophobic surface but not an amphiphobic surface, the sample liquid may transition from the Cassie state to the Wenzel state. In such a state, the sample liquid permeates upwards between the microstructures of the microstructure array, thereby reducing the volume occupied by gas, and reducing the capacity for gas exchange in the sample chamber. Then, gas exchange may be solely round the upper periphery of the sample chamber. Notwithstanding this effect, the hydrophobic (but not amphiphobic) microstructure array may nevertheless be sufficient to prevent the sample liquid from permeating outside the upper periphery of the sample chamber.

In many cases, gas exchange only around the periphery of the sample chamber is sufficient. However, there may be other cases (discussed in more depth below) where it is desirable to allow gas exchange to take place across the entire upper surface of the sample chamber.

Where it is desirable to maintain a large volume of gas above the sample liquid in the sample chamber (between the microstructures of the microstructure array), in the case that the sample liquid may not have the same wetting properties as water (for example, because it contains oily or detergent-like molecules), then it may be advantageous to provide a microstructure array that forms an amphiphobic surface. The sample liquid would then be less likely to transition from the Cassie to the Wenzel state (compared to the case where a hydrophobic but not amphiphobic microstructure array is used), such that the sample liquid does not permeate between the microstructures of the microstructure array. The amphiphobic microstructure array may then be provided across the whole of the entire upper surface of the sample chamber, in order to provide a layer of gas over the entire surface of the sample liquid, except that in contact with the microstructures of the microstructure array, to maximise gas exchange.

Where it is not important to maintain a large volume of gas above the sample liquid in the sample chamber (between the microstructures of the microstructure array), and in the case that the sample liquid may not have the same wetting properties as water (for example, because it contains oily or detergent-like molecules), then a hydrophobic (but not amphiphobic) microstructure array may still be used, on the understanding that the sample liquid may well be in the Wenzel state. That being the case, the hydrophobic (but not amphiphobic) microstructure array may then be provided only around the periphery of the upper surface of the sample chamber, as provision of the hydrophobic (but not amphiphobic) microstructure array across the entire surface of the sample chamber may be of little benefit.

The foregoing considerations are applicable also to the relevant discussions described above or below in respect of the other aspects of the invention.

Optionally, a through-hole in the upper layer in an area provided with the microstructure array forms a gas vent, allowing gas exchange between the sample chamber, gas reservoir and the atmosphere. A plurality of such vents may be provided. In some embodiments, gas vents are not provided. In such a case, gas from the sample chamber(s) is evacuated to the gas reservoir as the sample chamber is/are filled with liquid, causing an increase in the pressure in the gas reservoir. Gas is then not vented to the atmosphere from the sample holder.

Optionally, the sample chamber is formed as a through-hole in a middle layer. Optionally the gas reservoir is formed as a blind hole in the middle layer (open to the top surface of the middle layer, but not open to the bottom surface of the middle layer).

The middle layer may be bonded to the upper layer. At the top periphery, the sample chamber(s) may be sealed to liquid egress by the hydrophobic microstructure array, or partially by the hydrophobic microstructure array and partially by a bonding pattern which joins the middle layer to the upper layer. In some embodiments, the hydrophobic microstructure array overlaps with only one top edge (or part thereof) of the/each sample chamber. In that case, the/each sample chamber may be sealed at the remaining top edges using a bonding pattern to avoid leakage of liquid along those edges. A continuous bond around a sample chamber between the upper layer and middle layer may not be necessary in the regions where the upper layer comprises a hydrophobic surface.

Where a bond is present between an area of the microstructure array (on the upper layer) and the middle layer, optionally only the tips of the microstructures forming the microstructure array are bonded to the middle layer, to maintain the spacing between the microstructures.

Optionally, a lower layer is bonded to the middle layer. At the bottom periphery, the sample chamber(s) may be sealed to liquid egress by a bonding pattern which joins the middle layer to the lower layer.

The gas reservoir may comprise a specific gas or gas mixture, different from air, which may be selected so as to provide a particular analysis condition in one or more sample chambers. For example, the gas or gas mixture may not include oxygen, so as to provide anaerobic conditions within some or all of the sample chambers.

Optionally, the sample holder comprises a waste reservoir, wherein the microstructure array overlies at least a portion of a top periphery of the waste reservoir, or overlies a waste reservoir venting channel extending from the waste reservoir. Optionally, the waste reservoir is formed as a through-hole in a middle layer. Optionally the waste reservoir venting channel is formed as a groove in the top surface of the middle layer (but may alternatively be formed as a groove in the bottom surface of the upper layer).

The sample chamber may form part of a fluidic network (comprising a sample inlet, one or more fluid filling channels connected to the inlet at one end and optionally a waste reservoir at the other, a plurality of branch channels branching off one of the one or more fluid filling channels, a plurality of sample chambers each connected to one of the plurality of branch channels, and optionally, a geometric restriction between each fluid filling channel and an optional waste reservoir. Each of these features may be as described above in reference to the optional features of the first aspect of the invention. Thus, the sample holder may comprise such a fluidic network, with any of the optional features disclosed above.

The sample holder may comprise a plurality of fluidic networks, in which case a corresponding plurality of separate microstructure arrays may be provided, and one microstructure array may serve one fluidic network.

The upper, middle and lower layers discussed herein may have features corresponding to those described in above respect of the upper, middle and lower layers in reference to the optional features of the first aspect of the invention.

The middle layer may be joined to the upper layer in such a way as to control gas exchange within the sample holder (for example, to allow gas exchange with the atmosphere, or only with gases provided in certain gas reservoirs, for a selected number of sample chambers). This may allow different conditions to be applied in sample chambers in different portions of the sample holder. In particular, the two layers may be joined with a bonding pattern which isolates a portion or portions of the sample holder from other parts of the sample holder and/or from the atmosphere. For example, the bonding pattern may be used to isolate a certain portion of the sample holder from the atmosphere, so that gas exchange between sample chambers in the certain portion is only possible with gas reservoir(s) which is/are also isolated from the atmosphere. For example, a fluidic network and an associated gas reservoir may be isolated from the atmosphere. Using the bonding pattern in this way is a cheap and reproducible way of achieving controlled (i.e. selective) gas exchange within the sample holder.

The middle layer may be joined to the upper layer using a welding process (for example, laser welding, RF welding, ultrasonic welding), glue or solvent bonding, for example. The lower layer may be joined to the middle layer using the same process. In one embodiment, layers may be joined using laser welding. Alternatively, layers may be joined by ultrasonic welding The sample holder may comprise a sample inlet port (which may include a docking guide), as described above in reference to optional features of the first aspect.

The sample holder may comprise a flexible membrane layer and/or a magnetic metal layer as discussed above in reference to the optional features of the first aspect of the invention.

The sample holder may comprise additional reservoirs (and optionally associated features, such as liquid waste channels, sub-reservoirs, gas channels, etc.) as discussed above in reference to the optional features of the first aspect of the invention.

The sample holder layers may have the properties discussed above in reference to the first aspect of the invention.

The sample holder may be filled with sample (and the fluid filling channels subsequently evacuated of sample) as described above in respect of the discussion of the first aspect.

According to a third aspect, the invention provides a sample holder comprising a fluidic network comprising an inlet, and a fluid filling channel, wherein the fluid filling channel has a first end and a second end, the first end being connected to the inlet, wherein the fluidic network further comprises a plurality of sample chambers, each connected to the fluid filling channel via a respective branch channel branching off from the fluid filling channel.

The fluidic network may comprise a waste reservoir, and the second end of the fluid filling channel may be connected to the waste reservoir. A restriction to fluid flow may be provided at the second end of the fluid filling channel, or the fluid filling channel may itself act as a restriction to fluid flow into the waste reservoir The waste reservoir may be a dedicated waste reservoir, or it may be a gas reservoir also utilised as a waste reservoir. In use, only a partial volume of the gas reservoir may be filled with waste.

In some embodiments, there is no waste reservoir present in the fluidic network.

The third aspect of the invention may comprise any of the optional features of the first or second aspects of the invention, and these may provide similar functions and/or advantages. Optional features may be combined with each other optional feature, except in cases where the features are mutually exclusive alternatives.

Optionally, the fluidic network comprises a plurality of fluid filling channels, and optionally a plurality of waste reservoirs, each of the fluid filling channels being connected at their first end to the inlet and optionally at their second end to a respective one of the optional plurality of waste reservoirs. Each fluid filling channel optionally may have a plurality of branch channels branching off to a corresponding plurality of sample chambers. Each fluid filling channel may have a restriction to fluid flow provided at its second end.

There may be no waste reservoir present in the fluidic network.

The restriction may have the same features and advantages discussed above in reference to the optional features of the first aspect.

Optionally the (or each) branch channel opens into the (respective) sample chamber at the lower periphery of the sample chamber. Fluid entering the sample chamber therefore fills the sample chamber from the bottom up.

The branch channels may be used to store a small amount of sample liquid (once the sample liquid has been introduced into the sample holder) which can be used to maintain the level of fluid in the sample chamber, in the event that some of the sample in the sample chamber evaporates during the analysis. The, or each, branch channel may therefore be used as a sample liquid top-up reservoir.

As described in relation to the first aspect, the fluidic network may comprise an extra volume provided in the middle layer to allow for different fill volumes of the sample and to allow for some liquid evaporation without loss of liquid from the sample chambers.

As described in relation to the first aspect, the fluidic network may comprise a fluid filling channel shaped so as to have the effect of partially separating the plurality of sample chambers connected to the fluid filling channel into subgroups.

The sample holder optionally comprises a plurality of fluidic networks, as described above in reference to the optional features of the first aspect.

As described above in reference to the optional features of the first aspect, there may be only one inlet, with all the fluid filling channels connected to that inlet. In that case, a central inlet reservoir may be provided, and is configured to receive sample via the inlet.

The sample holder optionally comprises three layers: an upper layer, a lower layer, and a middle layer sandwiched between the upper and middle layer.

As described in reference to optional features of the first aspect, the fluidic filling network(s) may be primarily defined in the middle layer.

The sample holder may comprise a sample inlet port, as described above in reference to optional features of the first aspect.

The sample holder may comprise a gas reservoir in communication with a sample chamber via a gas film, wherein the gas film may be provided at an interface between the middle layer and upper layer.

The gas film is optionally provided by an array of microstructures formed on at least a portion of the bottom surface of the upper layer (i.e. the surface which faces onto the middle layer).

The microstructure array may extend around the entire top periphery of the sample chamber, or around just part of this periphery. In terms of its extent within the periphery of the sample chamber (and implying no limitation on the extent of the microstructure array outwardly of the periphery of the sample chamber) the microstructure array may extend only around the periphery (or part thereof), or may extend also across part or a whole of the entire upper surface of the sample chamber. The microstructure array may extend outwardly of the periphery of the sample chamber, for example to allow a gas connection between the sample chamber and a gas reservoir or a gas vent.

The microstructure array may overlie the top periphery of the sample chamber at a first position, and may overlie at least a portion of a top periphery of a gas reservoir at a second position, and may extend between the first position and the second position, such that a gas path between the sample chamber and gas reservoir is formed by the microstructure array.

Alternatively, a gas path extending from the microstructure array to at least a portion of a top periphery of the gas reservoir may comprise a groove in the upper layer or middle layer, which is not provided with microstructures.

The microstructure array may connect to, overlie or partly overlie one, or a plurality of, gas channels. The gas channels(s) may be formed in the top surface of the middle layer (in which case, the microstructure array overlies or partly overlies the gas channel(s). Alternatively, the gas channels may comprise a groove in the upper layer (in which case, the microstructure array connects to the gas channel(s).

The gas channel(s) may run to a position where the gas channel(s) is/are open to the atmosphere. For example, the gas channel(s) may open into a gap which is open to the atmosphere. This gap may be provided between an inner periphery of the upper layer and an outer periphery of a raised section of the middle layer (described in detail above). The microstructure array may thereby be vented; gas (for example, air) can move from the microstructure array into the gas channels(s), along the gas channel(s) and into the gap, which is open to the atmosphere.

The gap may have a width of between 0.1 and 1 mm. The gap may have a width of, for example 0.15 to 0.5 mm, and optionally may have a width of 0.2 to 0.35 mm.

The microstructure array optionally forms a hydrophobic surface which overlies at least part of the top periphery of the, or each, sample chamber and prevents liquid from escaping the, or each, sample chamber via the gas film. As a result, gas can move in and out of the sample holder, but liquid cannot. As noted above, the term "hydrophobic surface" is intended also to cover an amphiphobic surface.

The properties of the microstructure array are as discussed above in reference to the relevant optional features of the first aspect of the invention.

The sample chamber(s) may be sealed with respect to outward liquid flow at their upper and lower peripheries, as discussed above in reference to the optional features of the first aspect of the invention.

The sample holder may comprise a gas vent, or a plurality thereof, as described above in reference to the optional features of the first aspect of the invention. In some embodiments, gas vents are not provided. In such a case, gas from the sample chamber(s) is evacuated to the gas reservoir as the sample chamber is/are filled with liquid, causing an increase in the pressure in the gas reservoir. Gas is then not vented to the atmosphere from the sample holder.

As described above in reference to the optional features of the first aspect of the invention, the gas reservoir(s) may contain air or a specific gas or gas mixture, different from air, which may be selected so as to provide a particular analysis condition in some or all of the sample chambers.

The sample holder may comprise a flexible membrane layer and/or a magnetic metal layer as discussed above in reference to the optional features of the first aspect of the invention.

The sample holder may comprise additional reservoirs (and optionally associated features, such as liquid waste channels, sub-reservoirs, gas channels, etc.) as discussed above in reference to the optional features of the first aspect of the invention.

The sample holder layers (and the bonding between the layers) may have the properties discussed above in reference to the first aspect of the invention.

The sample holder may be filled with sample (and the fluid filling channels subsequently evacuated of sample) as described above in respect of the discussion of the first aspect.

The following optional features may be combined with either of the first, second, or third aspects above (and of course with any of the optional features of those aspects described above).

The sample holder may include the samples. The samples may include microscopic objects contained in a sample fluid, such as the microscopic objects discussed above. The fluid may be a liquid with the microscopic objects in suspension or present on the surfaces of the sample chamber the sample is contained within. The sample fluid may include clinical samples or material derived from clinical samples, wherein the clinical samples include, but are not limited to, blood, serum, plasma, blood fractions, joint fluid, urine, semen, saliva, faeces, cerebrospinal fluid, gastric contents, vaginal secretions, mucus, a tissue biopsy sample, tissue homogenates, bone marrow aspirates, bone homogenates, sputum, aspirates, wound exudate, swabs and swab rinsates e.g. a nasopharyngeal swab, other bodily fluids and the like. The sample fluid may include a culture medium and could be a mixture of clinical samples or material derived from clinical samples with culture medium.

The microscopic objects may include particles (particularly bio-particles), cells (for example mammalian cells such as human cells), micro-organisms such as bacteria, other pathogens such as viruses and fungal pathogens and/or molecules including macromolecules.

The microscopic objects may include pathogens (for example, bacteria, viruses or fungal pathogens), and the sample holder may be used for antibiotic susceptibility testing (AST). In such a case, the pathogens may be present in a sample fluid such as a microbiological growth medium (for example, cation-adjusted Mueller-Hinton broth (CAMHB)), for performing a broth microdilution assay. The sample chambers may comprise a plurality of antimicrobial agents at a plurality of concentrations.

During AST, the tested pathogen is cultured in the sample chambers. This process typically goes on for several hours. For some pathogens it is critical to ensure sufficient oxygen supply during culturing. The microstructure arrays ensure sufficient oxygen supply during culturing, since the microstructure array provides a gas film in which gases can diffuse laterally, enabling (in conjunction with a gas path and/or gas vent) gas exchange with the gas reservoirs and/or the atmosphere.

In some embodiments, the sample holder is a consumable single-use product that can be disposed of after use. This avoids the need for cleaning of the sample holder, and minimises the risk of contamination of samples.

The sample holder may be configured to test one single sample. In other embodiments, the sample holder may comprise a plurality of identical sections (for example, identical with respect to the selection of antimicrobial agents provided in each section), wherein each section is configured to receive and test a different sample (i.e. a sample derived from a different patient).

Optionally, the sample holder is broadly the same shape (i.e. circular) and size as a standard compact disk (CD). The sample holder may be manufactured using standard techniques to make a CD. Whilst in some embodiments the sample holder is circular, in other embodiments, the sample holder may be square, rectangular, or otherwise polygonal.

The sample holder may comprise a central hole, allowing for placement of the sample holder into an analysis device. In other embodiments, there is no such central hole.

In one exemplary sample holder, the sample holder comprises between 1 and 600 sample chambers, for example, 50 to 500 sample chambers, and more optionally 80 to 400 sample chambers, for example 96 chambers, 336 chambers or 384 chambers.

In some embodiments, the sample holder comprises a plurality of sample chambers located along radial lines of the sample holder, wherein a single sample chamber is located along each radial line, or a plurality of sample chambers are located along each radial line.

In other embodiments, the sample holder comprises a plurality of sample chambers located along a plurality of concentric circles having different radii on the sample holder, wherein a single sample chamber is located along each coaxial circle, or a plurality of sample chambers are located along each coaxial circle.

In still further embodiments, the sample holder comprises a plurality of sample chambers located along a plurality of parallel lines, wherein a single sample chamber is located along each parallel line, or a plurality of sample chambers are located along each parallel line.

In some embodiments, the sample chambers along a respective radial line, concentric circle or parallel line are all aligned, so that the respective radial line, concentric circle or parallel line passes through the centre of each sample chamber. In some embodiments, the sample chambers generally follow the radial line, concentric circle or parallel line, but are not all aligned with each other. The sample chambers may for example be shifted relative to one another, for example in an alternating staggered configuration. For example, the centre of some or all of the sample chambers may be offset from the radial line, concentric circle or parallel line along which they are distributed. For example, a first sample chamber on the radial line, concentric circle or parallel line may be shifted to one side of the radial line, concentric circle or parallel line, and a neighbouring, second, sample chamber on the radial line, concentric circle or parallel line may be shifted to the opposite side of the radial line, concentric circle or parallel line. The next sample chamber may then be aligned with the first, and the next may be aligned with the second, etc.

In examples having sample chambers following radial lines, there may be 12 radial lines of sample chambers, with 8 sample chambers along each radial line, or 16 radial lines of sample holders, with 6 sample chambers along each radial line, or 24 radial lines of sample holders, with 4 sample chambers along each radial line. Each of the foregoing examples comprises 96 sample chambers, but there may be more or fewer sample chambers. In other examples, there may be 48 radial lines of sample chambers, with 8 sample chambers along each radial line, or 64 radial lines of sample holders, with 6 sample chambers along each radial line, or 94 radial lines of sample holders, with 4 sample chambers along each radial line. Each of the foregoing examples comprises 384 sample chambers.

In other configurations, the number of sample chambers along each radial line may not be the same for all radial lines of the sample chamber. For example, radial lines of 6 sample chambers and 8 sample chambers may alternate. In one example, there may be 48 radial lines of sample chambers, with alternating lines of 8 sample chambers and 6 sample chambers.

In examples having sample chambers following coaxial circles (each circle lying at a different radius), there may be the same number of sample chambers on each coaxial circle (for example, there may be 8 coaxial circles with 12 sample chambers on each line), but more likely, there will be a different number of sample chambers on each coaxial circle (for example, an inner coaxial circle may have 4 sample chambers, the next may have 8, the next may have 12, the next may have 16, the next may have 24 and the outermost may have 32).

In examples having sample chambers following parallel lines, there are for example 32 parallel lines each having 12 sample chambers, or 16 parallel lines each having 24 sample chambers. There may be the same number of sample chambers on each parallel line, or there may be a different number of sample chambers on each parallel line.

Optionally, the sample chambers are broadly rectangular or square in cross-section, where the section line is taken in the horizontal plane, parallel to the main (upper and lower) surfaces of the sample holder. Put another way, the bottom surface of the sample chamber is broadly square or rectangular.

Each sample chamber has a "length" in the direction along the respective radial line, parallel line or coaxial circle, and a "width" in the direction perpendicular to that line. Here, "length" and "width" are labels only; no limitation is implied on the relative sizes of these dimensions. Thus, the width may be greater than, equal to, or smaller than the "length". In some embodiments, the sample chambers all have the same size, shape and aspect ratio (length/width). In other embodiments, one or more of these features may differ between different sample chambers.

Where a single sample chamber is provided, the sample chamber may be substantially the same size as the sample holder.

The length of the sample chamber(s) is optionally less than 70 mm, 60 mm, 50 mm, 30 mm, 20 mm, 10 mm, 5 mm or 3 mm. The width of the sample chamber(s) is optionally less than 100 mm, 50 mm, 20 mm, 10 mm, 5 mm, 4 mm or 2 mm. In some examples, the lengths and widths of the sample chambers may for example be 1-5 mm, optionally 1 to 3.5 mm, for example 1.5-3 mm. In other examples the width may be within those ranges with the length being larger than the width, for example 2-10 mm, optionally 2 to 7 mm, for example 3-6 mm. One example embodiment uses a width of about 2.2 mm and a length of about 4.5 mm.

The sample chambers may have a depth of less than 15 mm, less than 10 mm, or less than 5 mm.

Focus-verification structures (for example, pyramid-shaped or groove-shaped indentations), may be provided in the sample holder (for example, in the lower layer of the sample holder). Such structures are described in Q-Linea AB's application PCT/EP2017/064715 (WO 2017/216314). For example, the focus-verification structures may be provided in the bottom of each sample chamber, adjacent each sample chamber (i.e. spaced inwardly of the outer width of the sample chambers) or may be provided between adjacent sample chambers, spaced inwardly of the outer width of the sample chambers.

Alternatively, the focus-verification structures may be provided as a plurality of concentric circles. In an optional arrangement in which the sample chambers are also arranged in concentric circles, the concentric circle focus-verification structures may be arranged so that a portion of each concentric circle is visible in the same relative position of each sample chamber.

The sample holder may comprise an alignment marker (or a plurality thereof), for example, a contrasting mark, an indentation, or a protrusion, which is present on the sample holder at a distance from the centre of the sample holder where no other structures are present. This alignment structure can be used to determine the rotational alignment of the sample holder, for example when the sample holder is being processed (for example, during sample filling, and/or during sample analysis) in an analysis device. Alternatively, or additionally, the alignment structure may be used to rotationally align two or more of the upper layer, middle layer and lower layer during production of the sample holder. In one embodiment, the alignment marker comprises a through-hole through the middle layer, similar to the through-holes which form the sample chambers, but smaller in size. Alternatively or additionally, an alignment marker may be provided as a notch in the outer edge of the sample holder. In particular, the notch may be provided in the outer edge of the middle layer of the sample holder. In some embodiments, the notch is provided only in the middle layer of the sample holder, with no corresponding notch in the upper layer and lower layer.

Alignment markers may also be provided in the lower layer (for example, on the top surface of the lower layer) for alignment with markers in other layers. The lower layer may for example comprise markings produced by "frosting" (a very shallow checkerboard pattern produced during injection moulding of the lower layer). The alignment markings may include a marking at the outer edge of the lower layer, for alignment with a corresponding marking (for example the notch) in the middle layer. Two further markings may be provided, at different circumferential positions, such that the three markings are unevenly spaced around the lower layer, to produce an asymmetry in the marking, eliminating the possibility of mounting the lower layer to the middle layer upside down.

Indexing lines may also be included (one or more lines, extending partially along a radius of the sample holder) allowing alignment of the sample holder in a specific rotation when it is being processed. The indexing line(s) may be arranged along a radial line, rotationally positioned so that it does not intersect any sample chamber.

In one embodiment, during production the middle layer is aligned with the lower layer by aligning a marking at the outer edge of the lower layer with a notch in the middle layer. The upper layer is aligned with the middle layer by aligning narrowed portions of the microstructure arrays (described above) on the upper layer with the sample chambers in the middle layer.

According to a further aspect, the invention provides a method of manufacturing a sample holder according to the foregoing aspects (including any or all of the optional features thereof), comprising: injection moulding an upper layer, middle layer, and lower layer; joining the top surface of the lower layer to the bottom surface of the middle layer; and joining the bottom surface of the upper layer to the top surface of the middle layer.

Injection moulding the layers is advantageous as using such a process leads to low production costs. The tools (i.e. the moulds) are relatively costly; however they last for many production cycles, leading to a low cost per produced sample holder.

The step of joining the top surface of the lower layer to the bottom surface of the middle layer may include producing a pattern of bonding such that a portion of the sample holder is isolated from the atmosphere.

The steps of joining the top surface of the lower layer to the bottom surface of the middle layer and joining the bottom surface of the upper layer to the top surface of the middle layer may include joining the layers using a welding process (for example, laser welding, RF welding, ultrasonic welding), or by using glue or solvent bonding. Laser welding may be used, as this is a precise and reliable process. Alternatively, ultrasound welding may be used, as this may be advantageous on processing speed grounds. Optionally, the layers are pressed together during welding, to achieve a good bond.

The method may include the steps of treating parts of the sample holder (for example, a restriction in a fluidic network) to make the restriction more hydrophobic (compared to its properties without the treatment). In general, methods of applying such hydrophobic treatments are known in the art and are not discussed further herein.

The method may include the steps of treating parts of the sample holder (for example, the fluid filling channel(s) and/or branch channel(s) and/or sample chamber(s)) to make them more hydrophilic (compared to their properties without the treatment). In general, methods of applying such hydrophilic treatments are known in the art and are not discussed further herein.

The method may include the step of depositing a substance/substances (for example, reagent/reagents) into some or all of the sample chambers, optionally after the step of joining the top surface of the lower layer to the bottom surface of the middle layer, and prior to the step of joining the bottom surface of the upper layer to the top surface of the middle layer. The substance(s) may be dried in the sample chambers. The substance(s) may for example be deposited in different amounts in a plurality of chambers, so that when the sample chambers are filled with a sample, the substance(s) is/are present in different concentrations in the plurality of chambers. The substance may be an antimicrobial agent. The substances may be a plurality of different antimicrobial agents. In that case, the sample holder may be suitable for use in an AST analysis.

The method may include the step of providing any of the features described in the foregoing description of the first, second and third aspects, and the optional features thereof.

The invention also extends to a system for microscopy-based imaging of samples comprising a sample holder as described above (i.e. as described in the first or second aspects of the invention, and optionally including any or all of the optional features of the preceding aspects), and an imaging device for microscopy-based imaging of samples, as described in Q-Linea AB's applications GB 1721430.5 and PCT/EP2018/085692. Thus, the invention extends to: a sample holder as described above and an imaging device for microscopy-based imaging of samples, the imaging device comprising:

a line camera;

a support, configured to receive a sample holder;

an objective lens received by a lens holder, wherein the lens holder is operable to move the objective along an optical axis; and an autofocus system, wherein the support is configured to move the sample holder in a first direction relative to an imaging line of the line camera to capture an image of a first strip of the sample holder, wherein the autofocus system is configured to determine (for example, monitor) a focal plane, and is configured to output a signal which causes the lens holder to translate the objective lens in order to adjust the focal plane (if necessary), during movement of the sample holder in the first direction by the support, and wherein the support is configured to move the sample holder in a second direction to align the imaging line of the line camera with a position on a second strip of the sample holder.

The imaging device may comprise an illumination source, wherein the illumination source may be monochromatic, or a narrow-band source.

The illumination source may comprise a plurality of light sources, and/or a diffuser may be positioned between the illumination source and the sample holder, optionally between a/the condenser and the sample holder. Such embodiments are particularly advantageous (but not essential) for use with certain embodiments of the sample holder as described herein, because the microstructure array may be optically active and may have the effect of causing non-uniformity in the light incident onto the sample chambers. The microstructures may have the effect of refracting or block light so that the illumination intensity as perceived over the imaged areas in the focal plane is not even, but shows variations dependent on the shape of the microstructures. Such variations may be detrimental to the image and subsequent image processing. In such a case, the diffuser or plurality of light sources may act to provide a more even illumination to the sample chambers. Where a plurality of light sources is provided, these may be positioned to provide different path lengths for illumination of the sample chambers. Where a diffuser is provided, the diffuser may be an optical diffuser which diffuses the light evenly, or it may be an engineered diffuser comprising an engineered surface having structures designed to cancel out the light intensity variations caused by the microstructures.

In embodiments where the microstructure array is provided around only the top periphery of the sample chambers, the microstructure array may not affect the uniformity in the light incident onto the sample chambers, and so there may be no advantage to providing a diffuser and/or plurality of light sources in that case.

Advantageously, when the sample holder is used with an autofocus system as described above, it is advantageous that the lower layer of the sample holder has a thickness of greater than 0.5 mm. This is advantageous as it allows the autofocus system to readily set the focal plane at the bottom surface of the sample chambers in the sample holder (i.e. the top surface of the lower layer). For a thinner lower layer, the autofocus system may instead erroneously set the focal plane at the bottom surface of the lower layer.

As noted above, focus-verification structures may be provided in the sample holder. These may be spaced to appear in every 10th line, every 50th line, every 100th line, or more, captured by the line camera. The focus-verification structures may each have a width covering one or more lines, such as three or more lines. The width of the focus-verification structure may be 1-10 µm, for example.

The invention further extends to a method for performing microscopy-based imaging of samples using a system for microscopy-based imaging of samples comprising the sample holder as described above, and an imaging device (also as described above). The method comprises:

loading a sample holder onto a support configured to receive the sample holder;

moving the sample holder in a first direction, from a starting position on a first strip of the sample holder, to move the sample holder relative to an imaging line of a line camera, to capture an image of the first strip of the sample holder;

determining (for example, monitoring) a focal plane using the autofocus system as the sample holder is moved in the first direction;

in response to a signal from the autofocus system, moving an objective lens along the optical axis to adjust the focal plane (if necessary); and moving the sample holder in a second direction, to align the imaging line of the line camera with a position on a second strip of the sample holder.

When the sample holder is loaded, the autofocus system may set an initial focal plane, before the sample holder is moved.

As the sample holder is moved (for example, to be imaged) the autofocus system may monitor the focal plane, and may adjust the focal plane as necessary. Thus, "determining (for example, monitoring) a focal plane using an autofocus system as the sample holder is moved in the first direction; in response to a signal from the autofocus system, moving an objective lens along an optical axis to adjust the focal plane (if necessary)" refers to this monitoring of the focal plane, and adjustment of the focal plane if necessary.

The autofocus system may set the initial focal plane at a surface of the sample holder, and as the sample holder is moved (for example, to be imaged) the autofocus system may monitor the location of the surface of the sample holder, and may compensate for any deviations in that surface by adjusting the focal plane. If the surface of the sample holder were completely optically flat (and perfectly perpendicular to the optical axis), no adjustment of the focal plane would be required.

The sample holder may comprise one or a plurality of sample chambers, and the autofocus system may set the initial focal plane at the bottom surface of the sample chamber(s) in the sample holder. As the sample holder is moved (for example, to be imaged) the autofocus system may monitor the location of the bottom surface of the sample chamber(s) in the sample holder, and may compensate for any deviations in that surface by adjusting the focal plane. If the bottom surface of the sample chamber(s) in the sample holder were completely optically flat (and perfectly perpendicular to the optical axis), no adjustment of the focal plane would be required.

Thus, the autofocus system advantageously may be a tracking autofocus system, such that the autofocus system adjusts the focal plane as the sample holder moves, optionally with a response time sufficiently fast to account for any unevenness in a surface of the sample holder, and in particular for any unevenness in the bottom surface of the sample chamber(s) in the sample holder.

The focal plane of the line camera may be set at the same plane as the focal plane determined by the autofocus system. Alternatively, the line camera may be mounted with a slight offset in the direction of the optical axis in order to place the focal plane of the line camera at a slightly different level than the focal plane for the autofocus system.

The method may comprise loading the sample into the sample holder using positive pressure (for example, by pipetting the sample into the sample holder and relying on the pressure provided by the pipette to move the sample into the sample chambers) or using centrifugal force (for example by depositing the sample into a central reservoir in the sample holder, and spinning the sample holder to move the sample outwardly and into the sample chambers).

The method may comprise evacuating excess sample liquid in the fluid filling channels following loading the sample into the sample holder. Optionally, any sample liquid in the fluid filling channels may be displaced by an unreactive fluid (for example, air or oil, such as mineral oil). This may be achieved by docking a pipette filled with the unreactive fluid to the inlet and actuating the plunger, for example. Alternatively, this may be achieved by filling the unreactive fluid into a central reservoir in the sample holder, and spinning the sample holder to move the unreactive fluid through the fluid filling channels. The sample liquid in the fluid filling channels may then be pushed (for example, through the restriction) into the waste reservoir. As a result, each sample chamber (and associated branch channel) may be isolated. Advantageously, the possibility of cross-contamination between sample chambers is greatly reduced.

The sample holder optionally includes a plurality of antimicrobial agents, each at a plurality of concentrations, for performing an AST analysis. The samples may include pathogens present in a microbiological growth medium for performing a broth microdilution assay.

The method may comprise imaging the sample holder at a plurality of time points. The method may comprise checking whether the images are in focus by checking whether an associated focus-verification structure is in focus (as described for example in Q-Linea AB's application PCT/EP2017/064711 (WO 2017/216310)). The images acquired by the device may be analysed using an image analysis algorithm, for example as described in Q-Linea AB's application PCT/EP2017/064713 (WO 2017/216312). The invention is of course not limited to such an image analysis; any suitable image analysis method may be used.

The method may comprise determining the presence or absence, and/or amount of growth of pathogens in the sample chamber(s) at each time point (in order to perform an AST analysis).

Whilst the invention has been described in the foregoing as being particularly advantageous when used in an AST analysis, the invention is of course much more generally applicable, for example to drug screening or cell culture analyses.

Certain exemplary embodiments will now be described by way of example only with reference to the accompanying drawings in which:

FIG. 2 shows a cut-away perspective view of the sample holder of FIG. 1;

FIG. 3 shows a cut-away perspective view of a middle layer of the sample holder of FIG. 1;

Figure 6A:
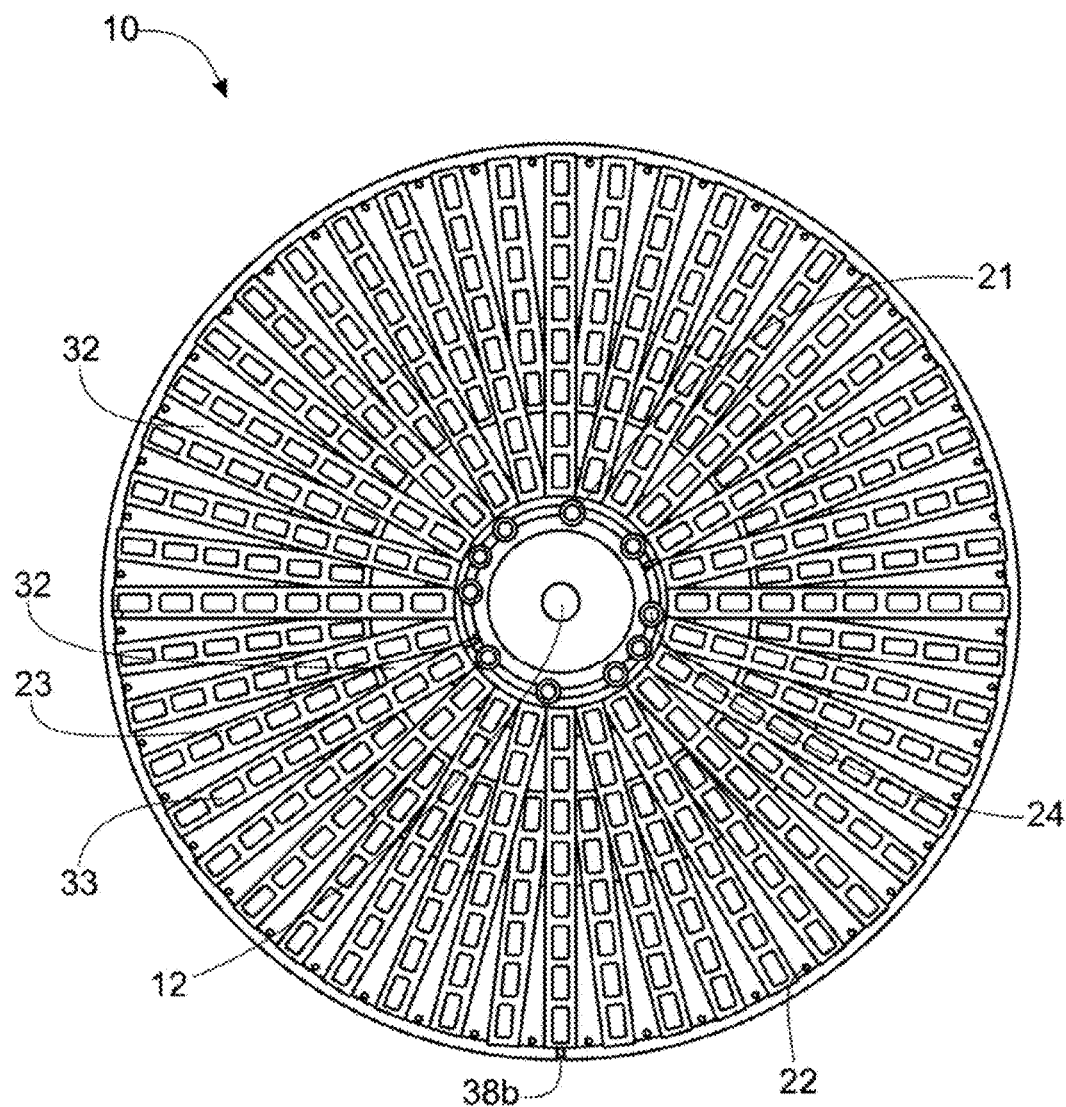
FIG. 6A shows a second sample holder in accordance with a further embodiment of the present invention.
Figure 9A:
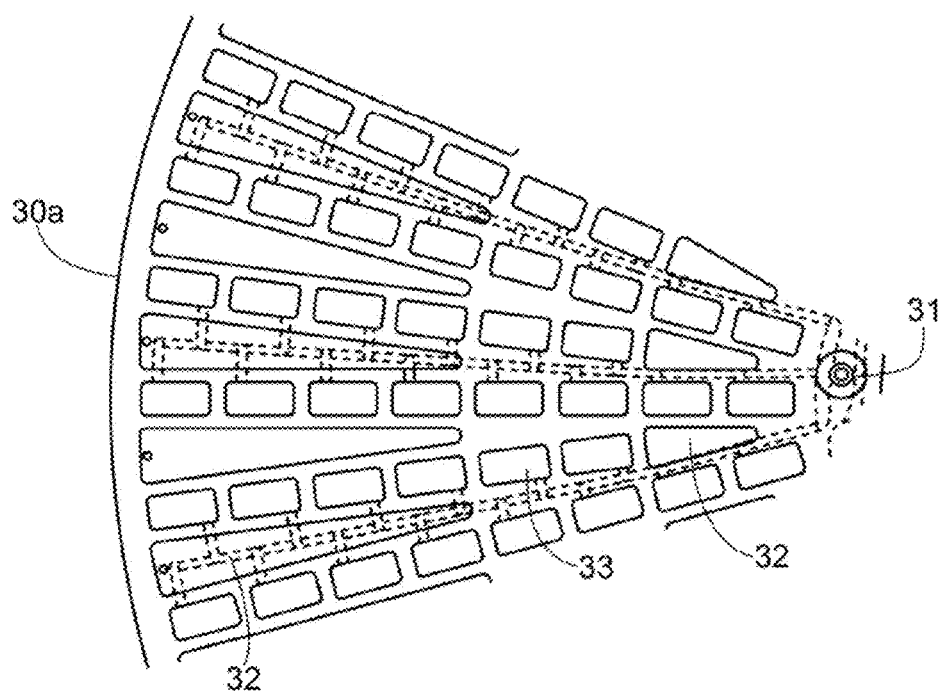
Figure 9B:
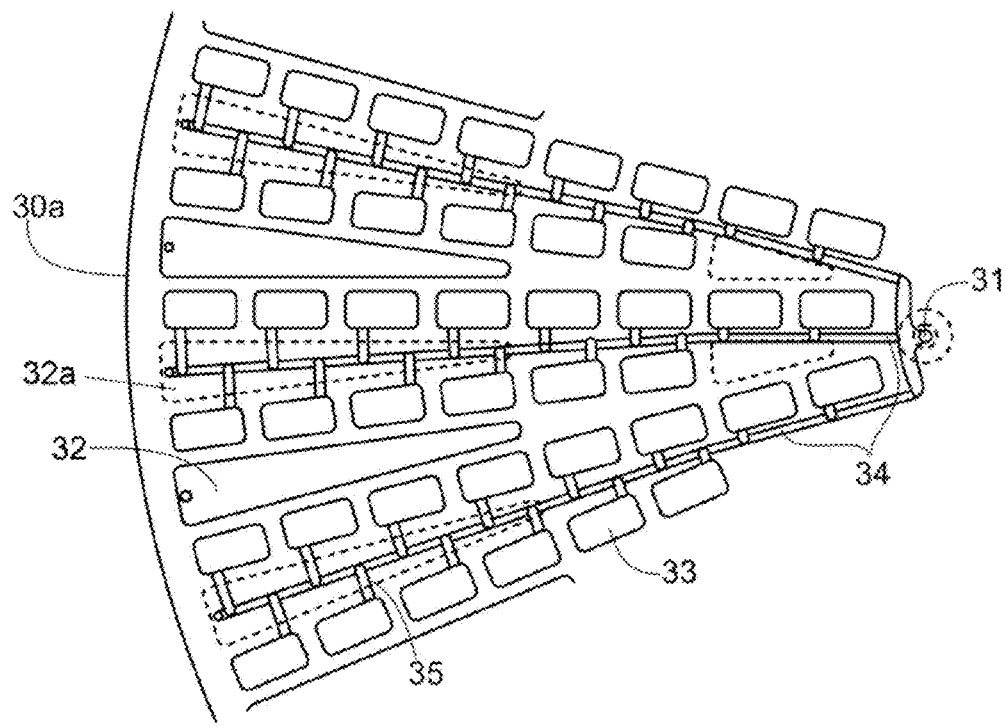
Figures 9C, 9D:
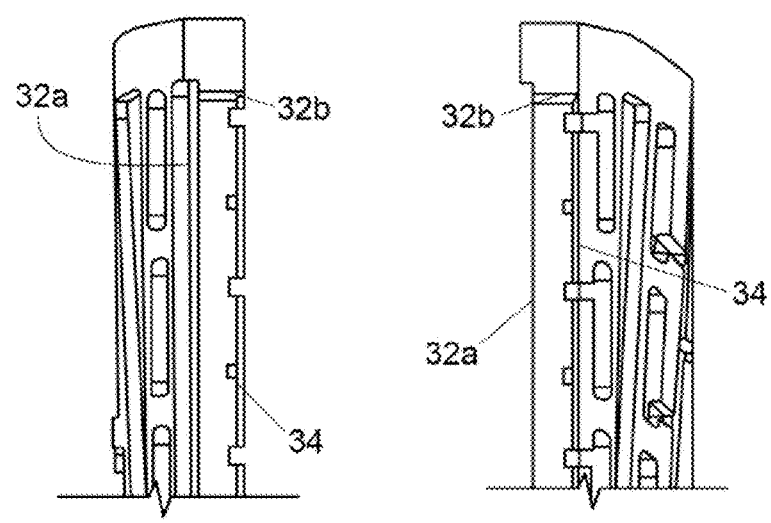
Figure 10A:
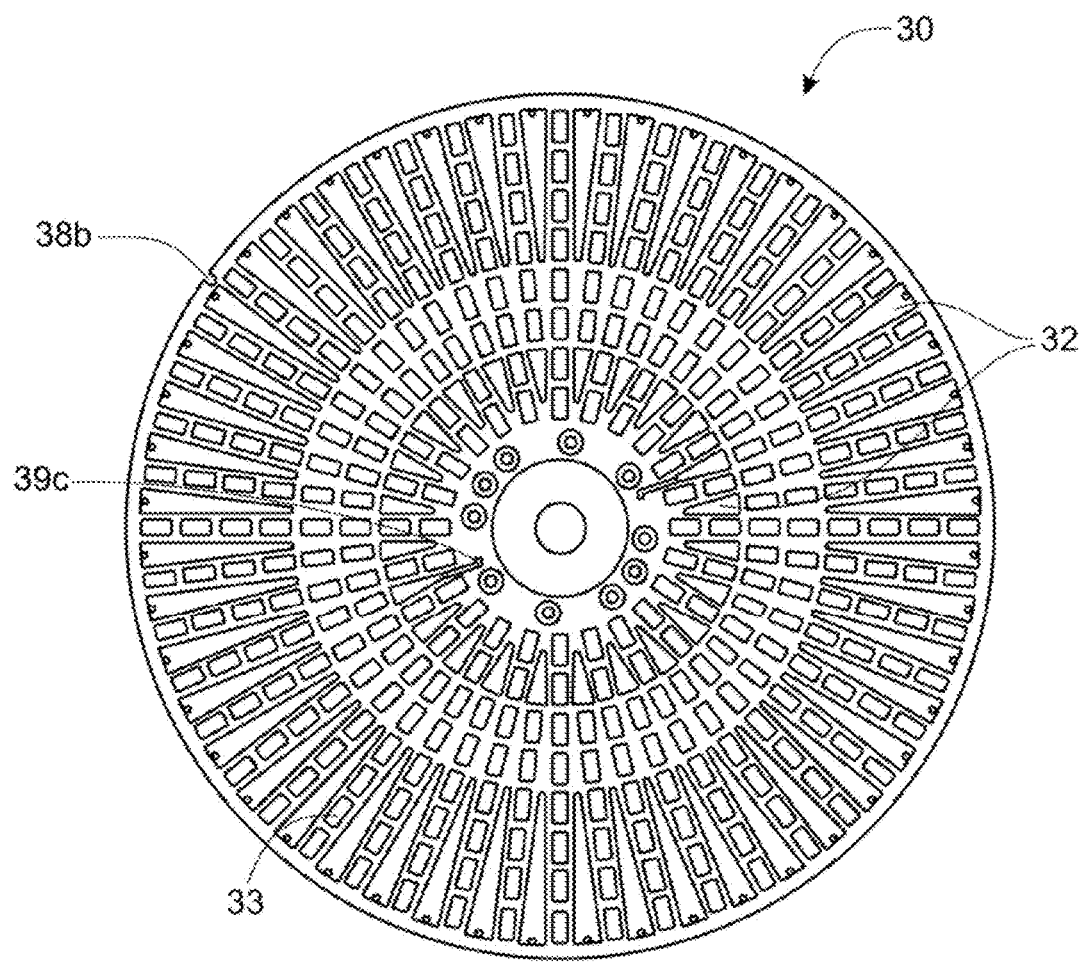
Figure 10B:
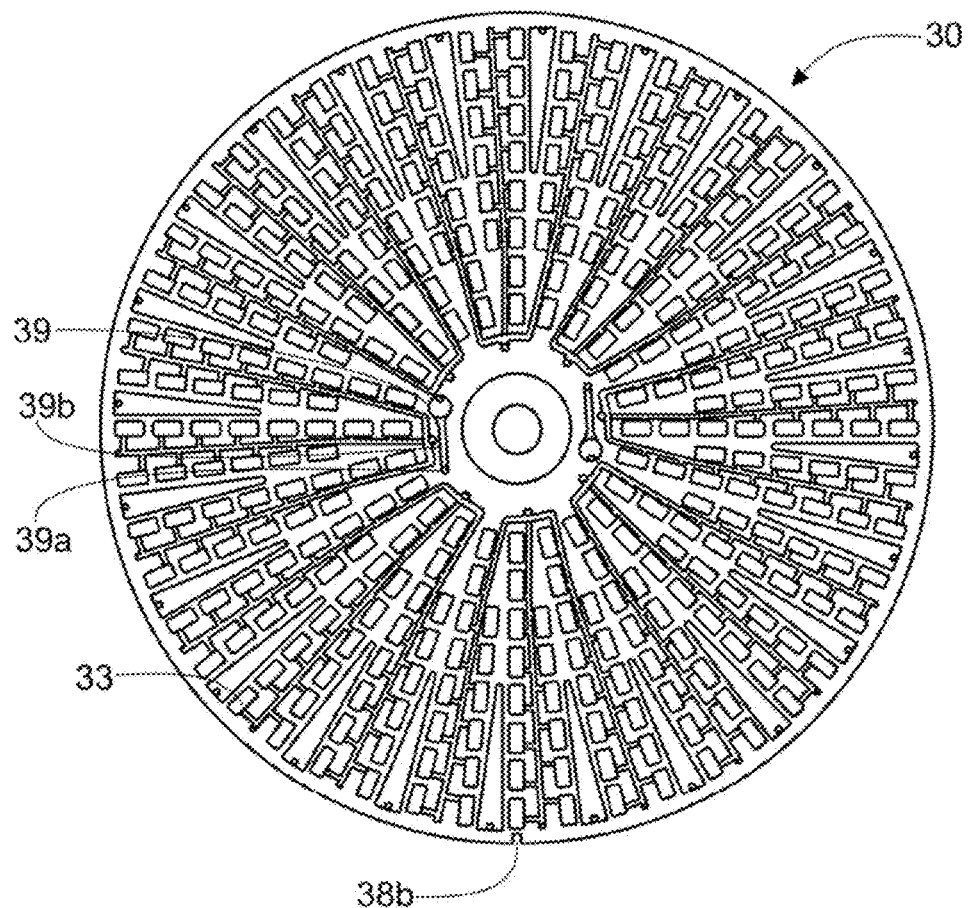
Figure 10C:
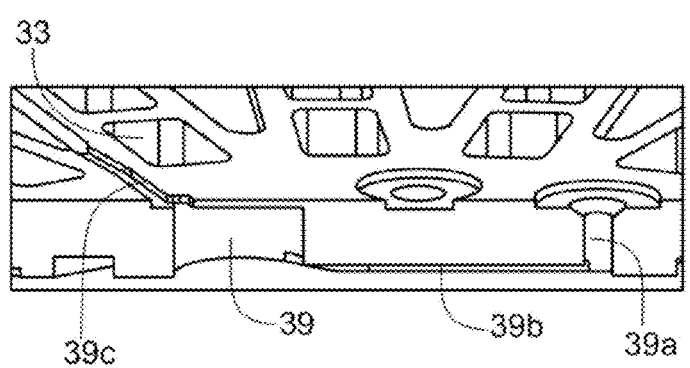
Figure 11:
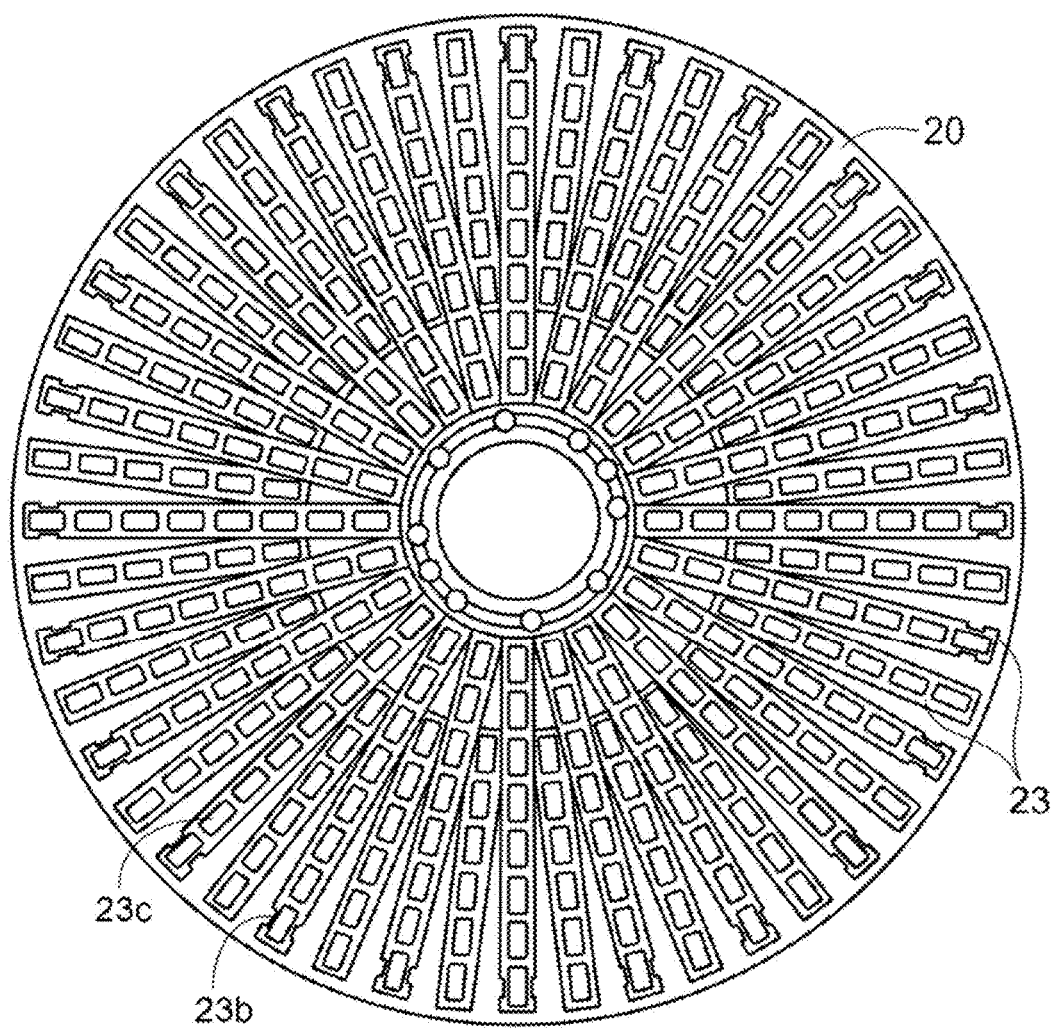
Figure 12:
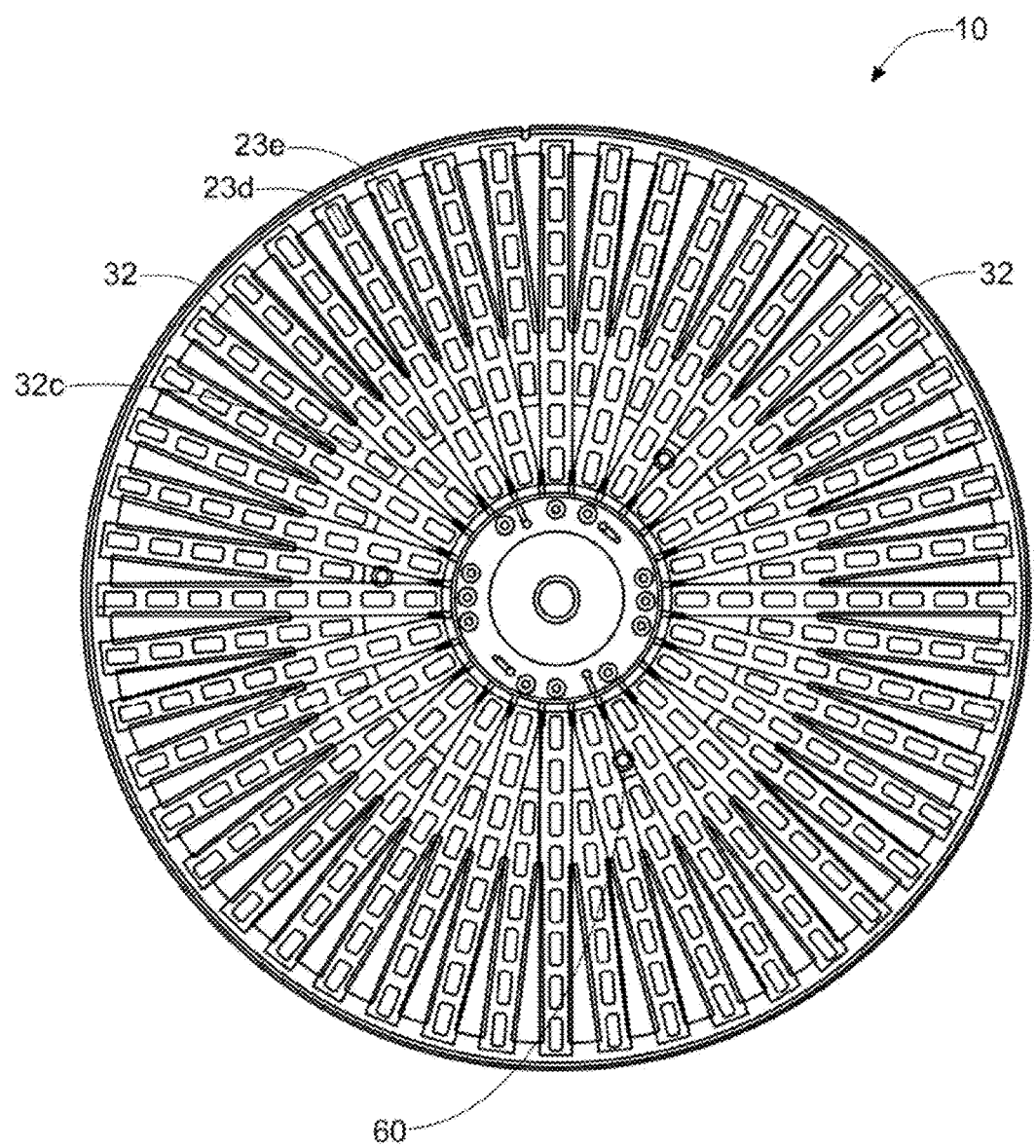
Figure 13:
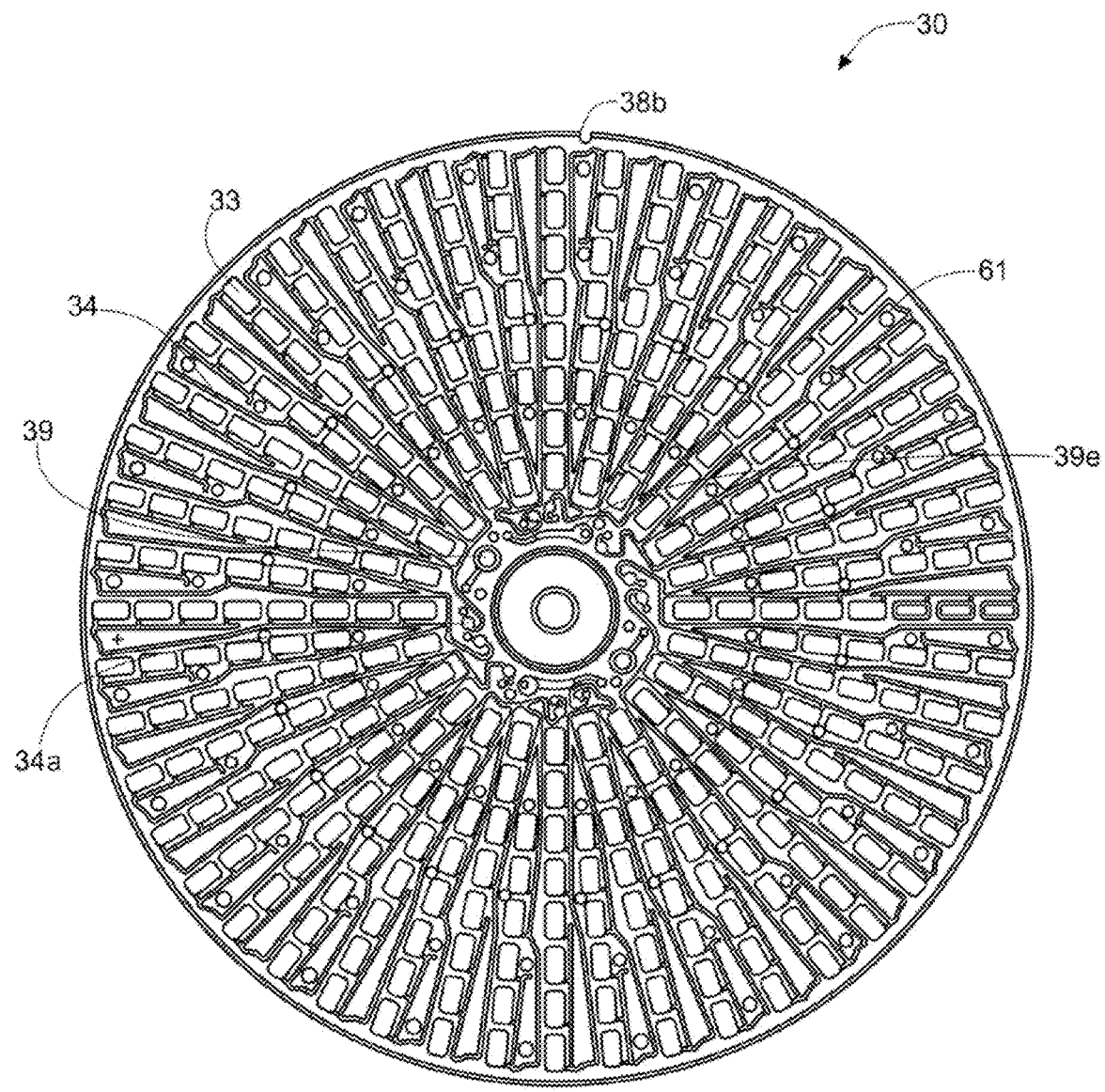
Figure 14:
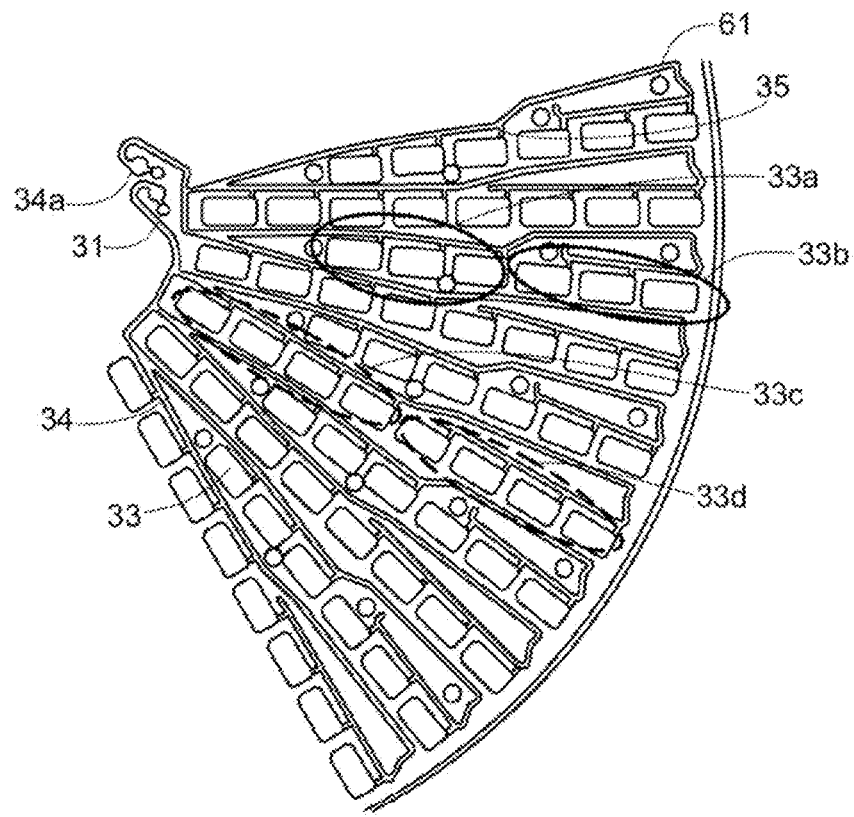
Figure 15:
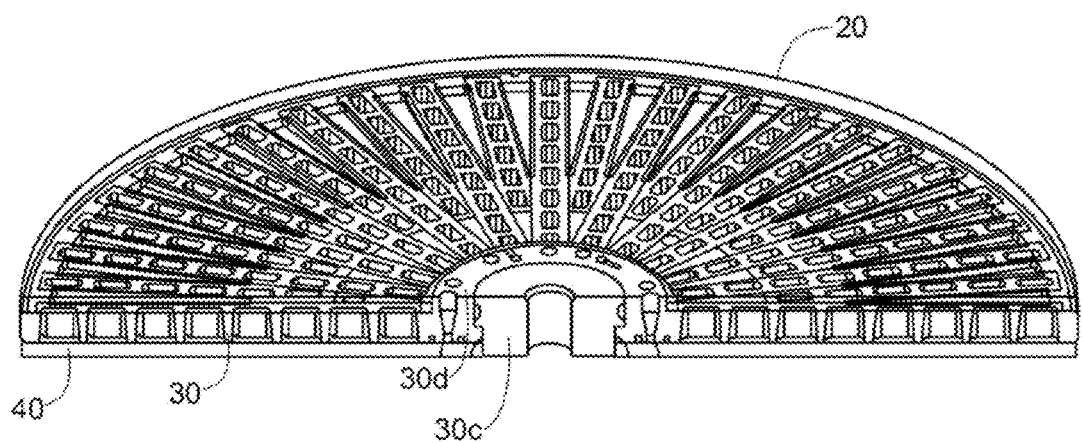
Figure 16A:
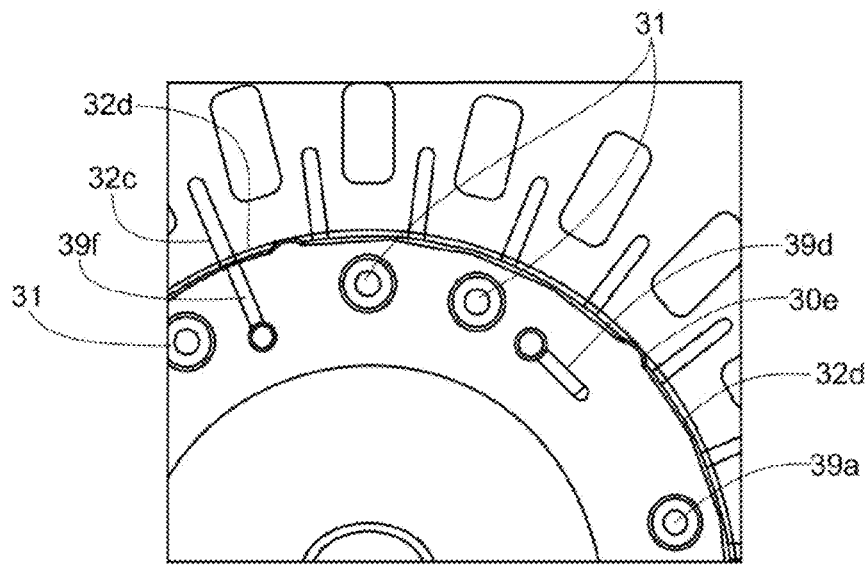
Figure 17:
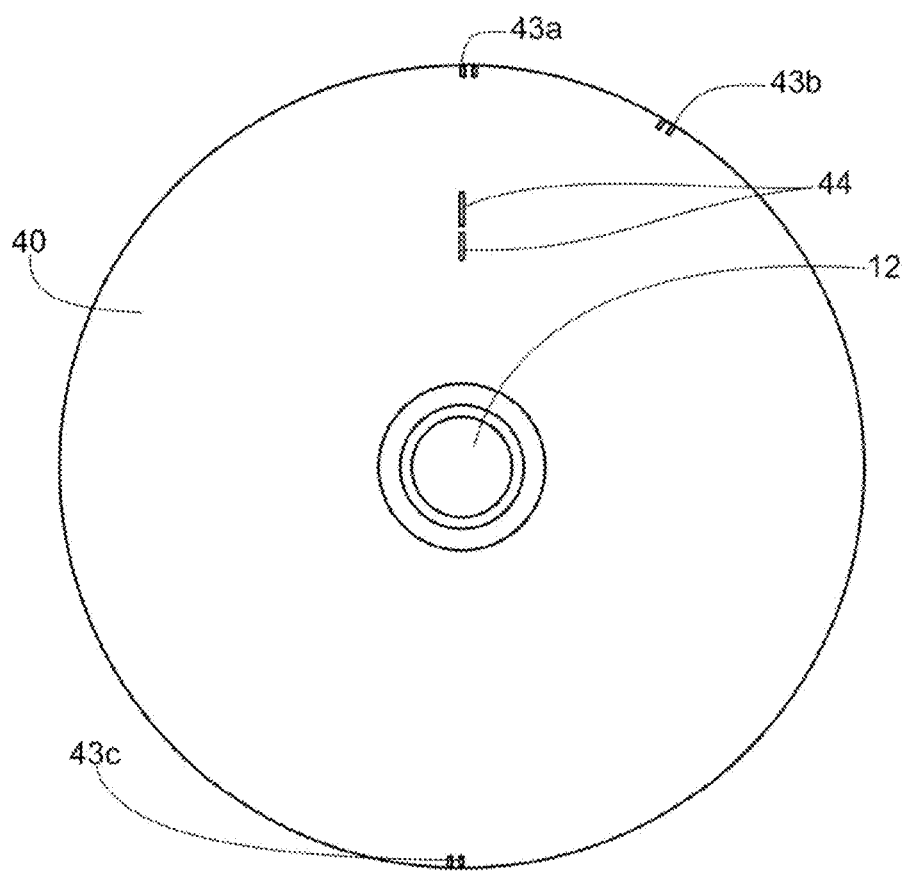
Figure 18:
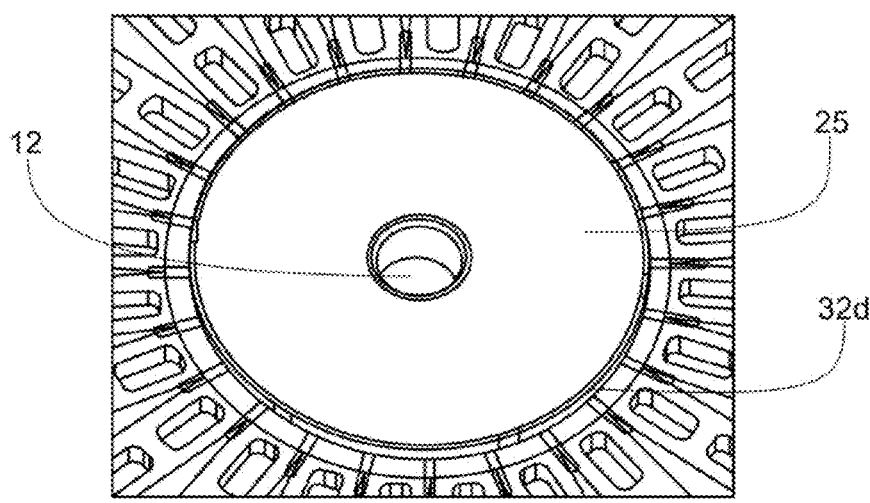
Figure 20:
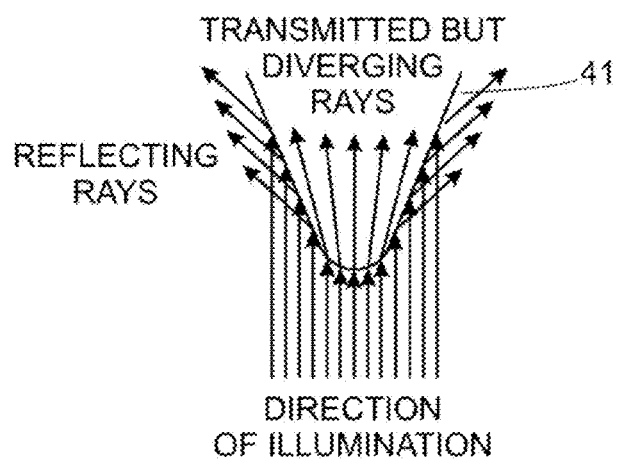
Figure 21A:
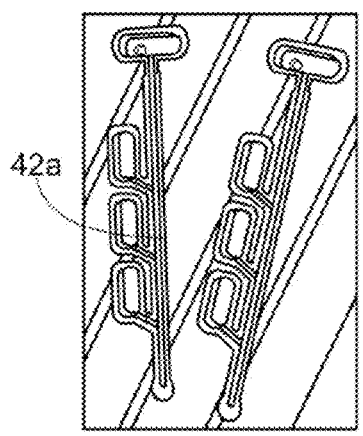
Figure 21B:
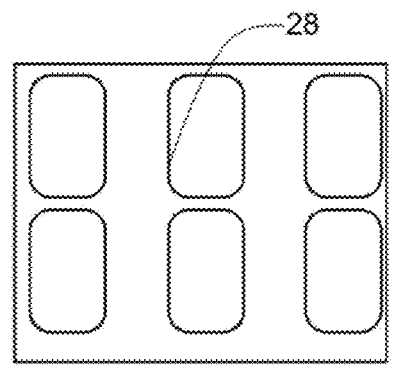
Figure 21C:
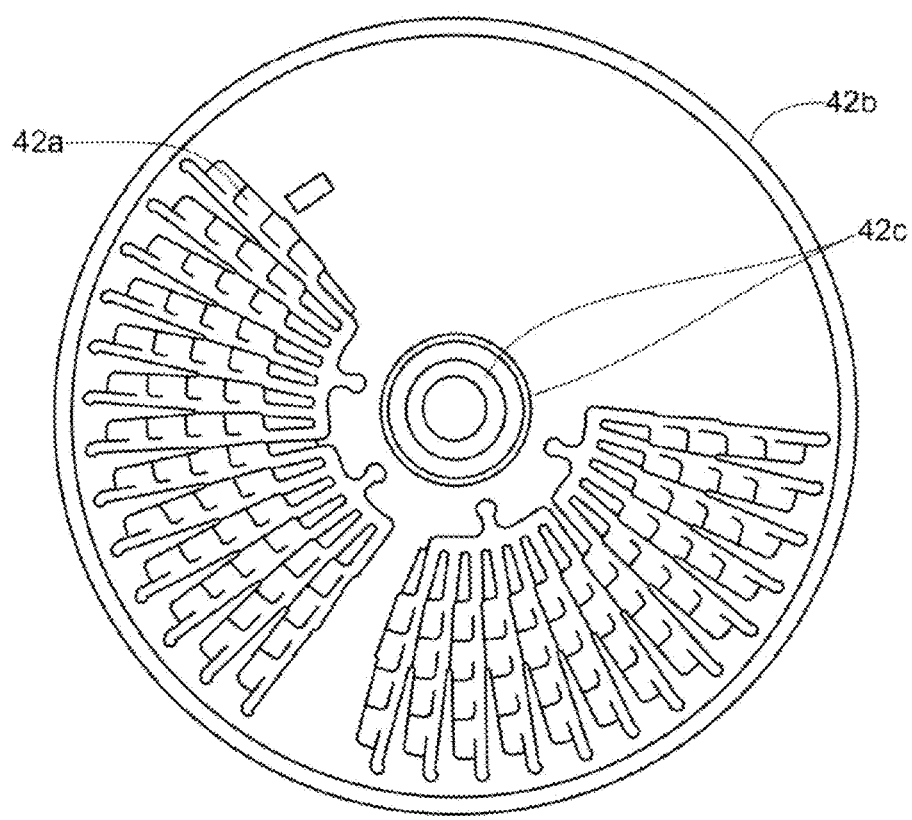
Figure 22:
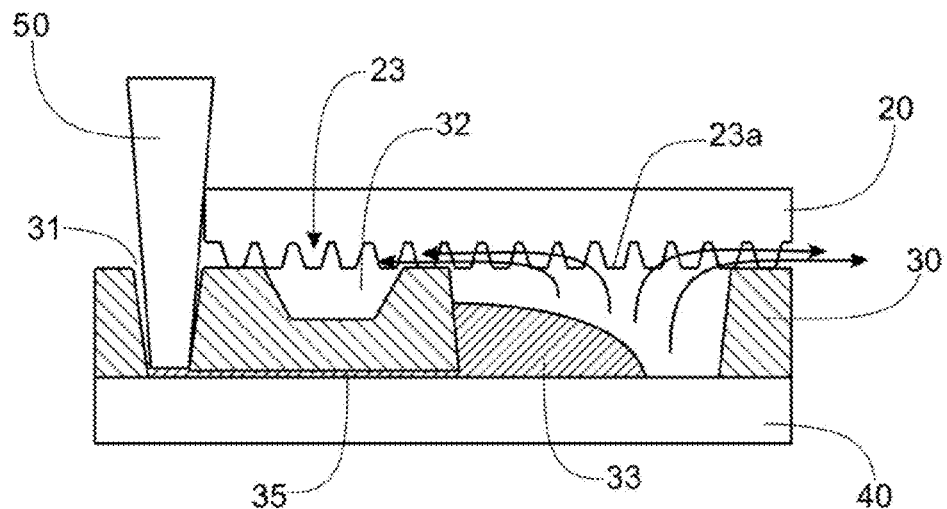
Figure 23:
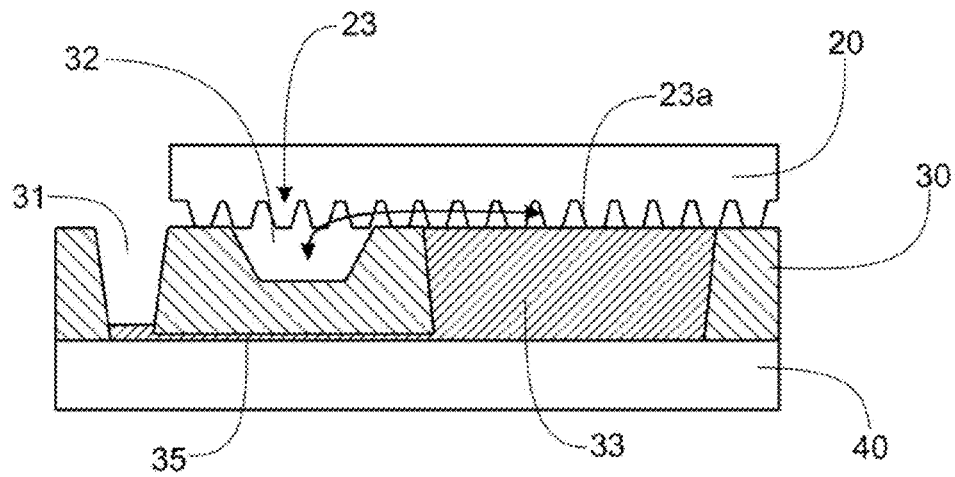
Figure 24A:
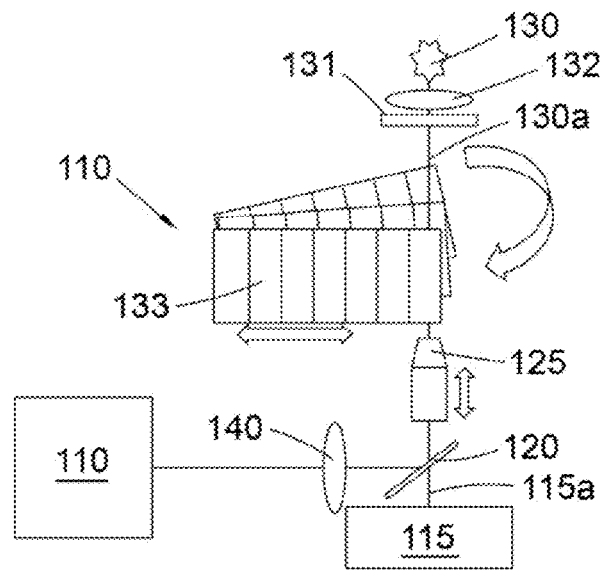
Figure 24B:
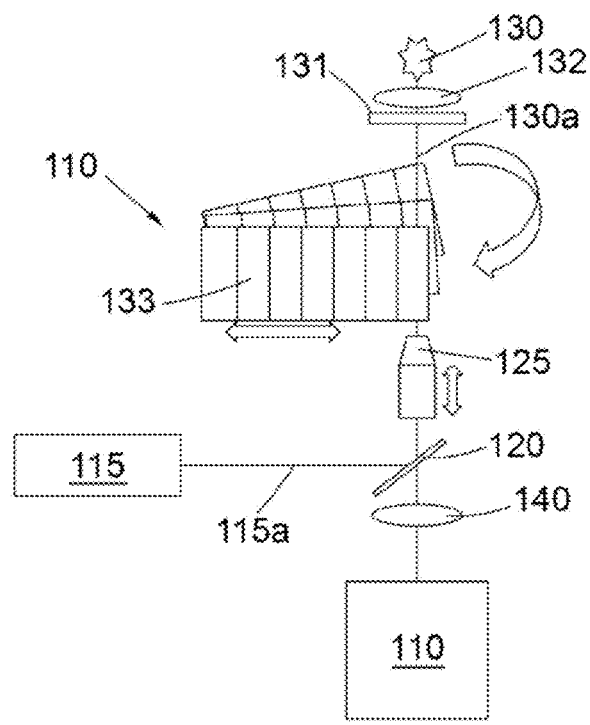
Figure 25:
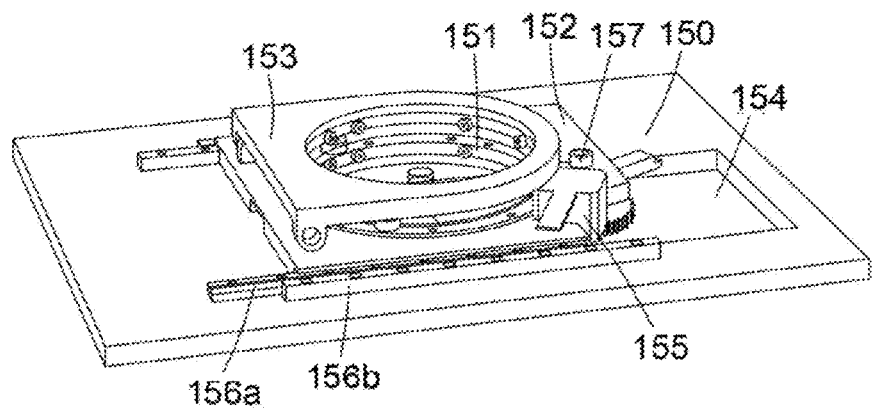

FIGS. 9A to 9D show a fluidic network in the sample holder of FIG. 6 (FIG. 9A shows a top view of part of the middle layer of the sample holder, FIG. 9B shows a bottom view of part of the middle layer of the sample holder, FIGS. 9C and 9D show respectively a close-up view of the top and bottom of the middle layer, showing a connection between the fluidic network and a gas reservoir also used as a waste reservoir;

FIG. 10A shows a top view of the middle layer of the sample holder of FIG. 6;

FIG. 10B shows a bottom view of the middle layer of the sample holder of FIG. 6;

FIG. 10C shows a partial cutaway perspective view of the middle layer of the sample holder of FIG. 6;

FIG. 11 shows an upper layer of the sample holder of FIG. 6;

FIG. 12 shows a third sample holder in accordance with a further embodiment of the present invention;

FIG. 13 shows a bottom surface of the middle layer of the sample holder of FIG. 12;

FIG. 14 shows an enlarged view of part of FIG. 13;

FIG. 15 shows a partial cutaway perspective view of the sample holder of FIG. 12;

FIG. 16A shows an enlarged view of part of the centre of the sample holder of FIG. 12, and FIGS. 16B to 16D show the flow of fluid introduced into an additional reservoir in this area;

FIG. 17 shows a lower layer of the sample holder of FIG. 12;

FIG. 18 shows a central part of the sample holder of FIG. 12, covered by a label;

FIGS. 19A to 19D show photographs of water droplets on each of a flat polystyrene surface, a polystyrene micropillar array, a flat Zeonor® surface, and a Zeonor® micropillar array;

FIG. 20 illustrates a light beam directed at a focus-verification structure on an exemplary sample holder and the resultant reflection and refraction of light rays;

FIGS. 21A to 21C illustrates exemplary bonds between the lower layer and the middle layer (FIGS. 21A and 21C) and the upper layer and the middle layer (FIG. 21B);

FIG. 22 shows sample liquid being introduced into a sample chamber of a sample holder;

FIG. 23 shows the sample liquid filled into the sample chamber of FIG. 22, and gas exchange from a gas reservoir;

FIGS. 24A and 24B show systems for microscopy-based analysis of samples;

FIG. 25 shows a support for a sample holder which forms part of the system of FIGS. 24A and 24B; and FIG. 26A shows the light source of the system of FIGS. 24A and 24B incident on an optically active layer in a sample holder, and FIGS. 26B and 26C show modifications to the light source to counteract the effect of such an optically active layer.

Figure 1:
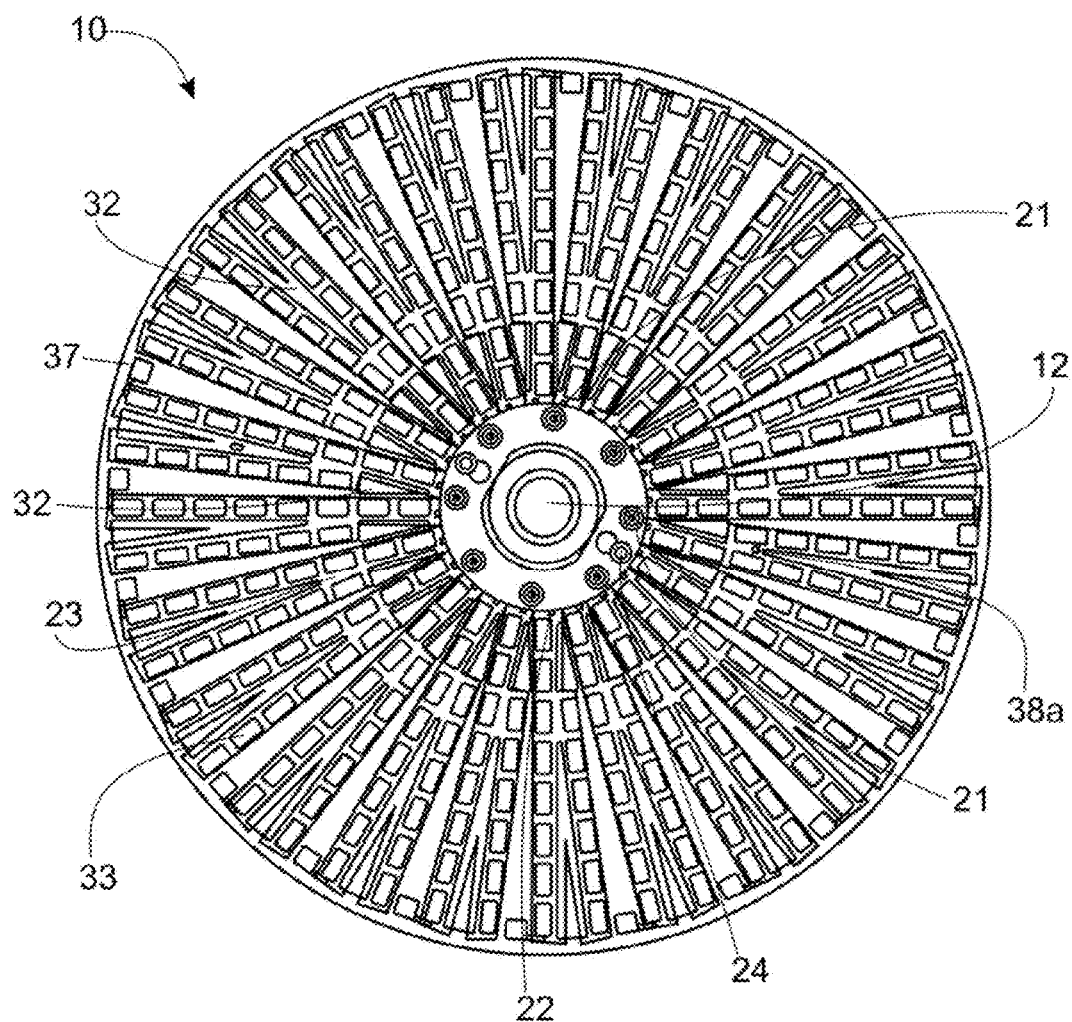
FIG. 1 shows a sample holder in accordance with an embodiment of the present invention.

As shown in FIG. 1, the sample holder 10 has a circular disc shape, and in this case, comprises 336 sample chambers. The sample holder 10 comprises three layers (see FIGS. 2, 9 and 10): an upper layer 20, a middle layer 30 and a lower layer 40, wherein the middle layer 30 is sandwiched between the upper layer 20 and lower layer 40.

As shown in FIG. 2, the middle layer comprises a main body 30a. As well as the main body 30a of the middle layer 30, a flexible membrane layer 30b and a magnetic metal layer 30c are provided between the upper layer 20 and lower layer 40 (on top of the main body 30a).

The flexible membrane layer 30b provides a sealing function to close off sample inlets to the sample holder 10, and comprises small holes (for example, pin holes) which can be opened under slight pressure, to allow sample to pass through the small holes.

The magnetic layer 30c allows the sample holder 10 to be moved or held in place using a magnet.

As shown in FIG. 2, the flexible membrane layer 30b and magnetic layer 30c only extend over an inner portion of the sample holder 10 (towards a radially inner area). The two layers are concentric, with the flexible membrane layer covering an outer annular area, and the magnetic layer covering an inner annular area, which overlaps slightly with the outer annular area.

The sample holder 10 in this example comprises a central hole 12. This central hole 12 may allow for placement of the sample holder 10 into an analysis device. In other embodiments, there is no central hole 12.

The main body 30a of the middle layer 30 (best shown in FIG. 3) defines the main operational structures of the sample holder 10. The main operational structures comprise: a plurality of sample inlets 31, a plurality of gas reservoirs 32, a plurality of sample chambers 33, a plurality of fluid filling channels 34, a plurality of branch channels 35, and a plurality of waste reservoirs 37. Also shown in FIG. 3 is a plurality of additional reservoirs 39. In this case, the additional reservoirs 39 are for receiving a sample for carrying out a concentration determination analysis. Instead, the additional reservoirs 39 may be used to hold a substance (for example, a reagent, in dried, liquid or lyophilised form) for use in an analysis, or for forming glue traps (such glue traps being provided to receive excess glue in embodiments in which the layers are glued together). As shown in FIGS. 1 and 2, additional inlets 24 to the additional reservoirs 39 may be provided in the upper layer 20.

Figure 4A:
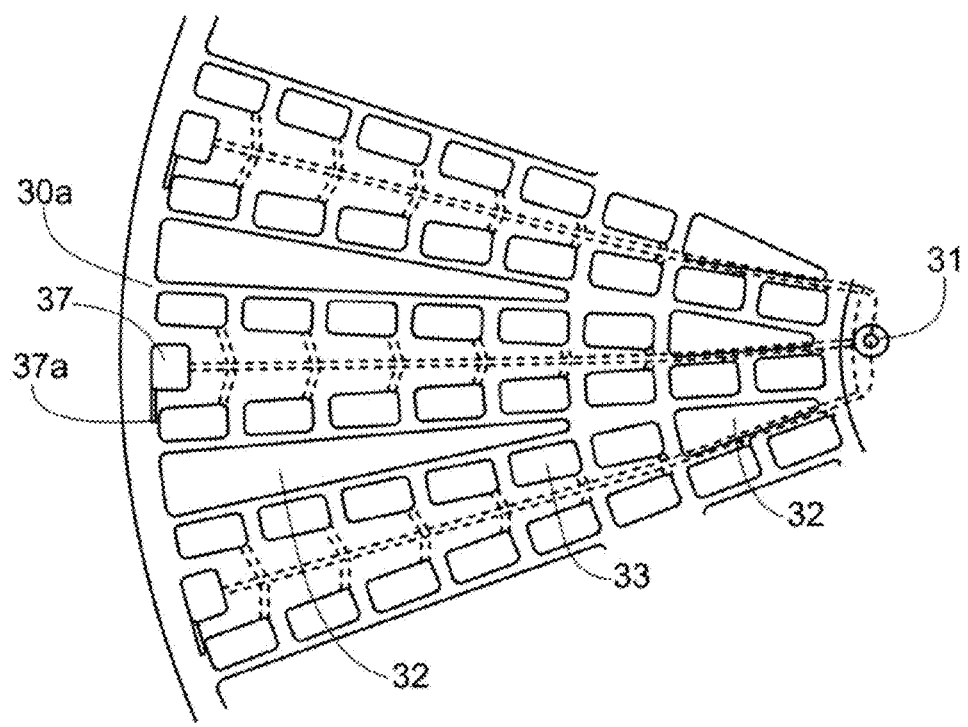
FIGS. 4A to 4C shows a fluidic network in the sample holder of FIG. 1 (FIG. 4A shows a top view of part of the sample holder, FIG. 4B shows a bottom view of part of the sample holder, and FIG. 4C shows a close up of a waste reservoir and the geometric restriction in the fluid filling channel leading into the waste reservoir)
Figure 4B:
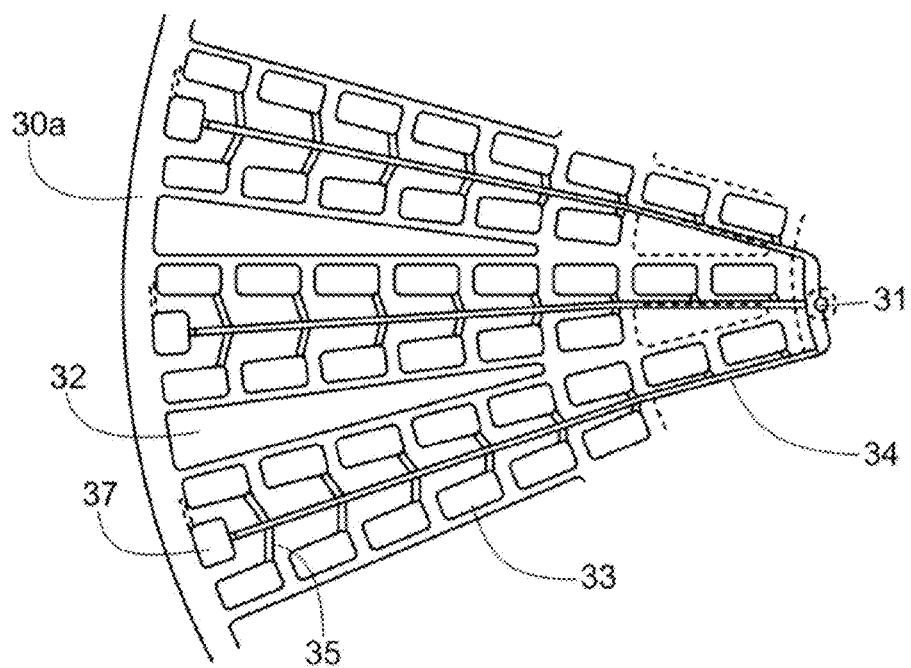

The locations of the gas reservoirs 32 are best shown in FIG. 4A, along with a plurality of sample chambers 33, a plurality of waste reservoirs 37 and an inlet 21. FIG. 4B shows the locations of the plurality of sample chambers 33, plurality of fluid filling channels 34, and plurality of branch channels 35, along with a sample inlet 31 and a plurality of waste reservoirs 37.

The sample inlets 31, sample chambers 33 and waste reservoirs 37 are formed from through-holes extending all the way through the main body 30a of the middle layer 30. The plurality of gas reservoirs 32 comprise blind holes extending downwardly from the top surface of the main body 30a of the middle layer 30 (i.e. the surface adjoining the upper layer 20). The plurality of fluid filling channels 34 and the plurality of branch channels 35 are formed as grooves in the bottom surface of the main body 30a of the middle layer 30 (i.e. the surface adjoining the lower layer 40). Thus, each fluid filling channel 34 and branch channel 35 is defined partially by the main body 30a of the middle layer 30 and partially by the top surface of the lower layer 40.

As best shown in FIG. 4B, each fluid filling channel 34 extends from a sample inlet 31 to a waste reservoir 37. Each sample inlet 31 may be connected to a plurality of fluid filling channels 34; in FIG. 4B, three fluid filling channels 34 are connected to a sample inlet 31, i.e. each sample inlet 31 supplies sample to three fluid filling channels 34. Similarly, each waste reservoir 37 may be connected to a plurality of fluid filling channels 34, or may be connected to only one fluid filling channels 34; in FIG. 4B, just one fluid filling channel 34 is connected to a waste reservoir, i.e. each waste reservoir 37 receives waste from just one of the plurality of fluid filling channels 34.

As further shown in FIG. 4A, there is a venting channel 37a (formed in a top surface of the middle layer 30) which extends from the top of each waste reservoir 37 into an area where a micropillar array 23 is provided (as discussed in more detail below). This allows gas in the waste reservoir 37 to be vented to the atmosphere (via the micropillar array 23) as the waste reservoir 37 is filled with liquid.

Figure 4C:
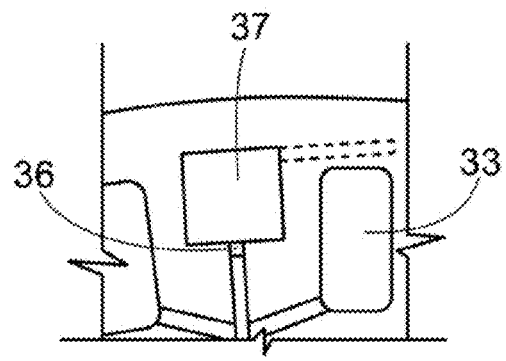

At the end of each fluid filling channel 34 where the fluid filling channel 34 connects to the waste reservoir 37, there is a geometric restriction 36 (see FIG. 4C) in the channel, i.e. the fluid filling channel 34 narrows at the point where it connects to the waste reservoir 37. The restriction 36 is mildly hydrophobic (which in this case is due to the intrinsic properties of the plastic used to manufacture the sample holder 10) and therefore the wetting resistance at this restriction 36 acts to stop the sample liquid from entering the waste reservoir 37 until the upstream fluid filling channel 34, sample chambers 33 and branch channels 35 are all filled with sample liquid.

The fluid filling channels 34 extend from the sample inlet 31 to the waste reservoir in a broadly radial direction. The sample inlet 31 is located at a radially inner position, and the waste reservoir 37 is located at a radially outer position.

A plurality of branch channels 35 extend from each fluid filling channel 34, and each branch channel 35 connects a single sample chamber 33 to the fluid filling channel 34. That is, multiple sample chambers 33 are connected to one fluid filling channel 34.

Each sample chamber 33 is effectively a blind chamber in respect of the sample liquid, i.e. it has a liquid inlet (via branch channel 35) but no liquid outlet. That is, each sample chamber 33 is isolated from the others. This minimises the risk of diffusion of the sample and/or any substances from one sample chamber 33 to another.

As noted above, each fluid filling channel 34 and branch channel 35 is defined partially by the main body 30a of the middle layer 30 and partially by the top surface of the lower layer 40. This means that the sample is introduced into the sample chambers 33 at the bottom of the sample chamber 33. This is advantageous in embodiments where a substance of some form is deposited on the lower surface of the sample chamber 33, as even mixing between the sample liquid and substance is then promoted. Moreover, filling from the bottom of the sample chamber 33 prevents the substance from being flushed out of the sample chamber 33.

The main body 30a of the middle layer 30 comprises an opaque material (in this case, polystyrene). In the embodiments shown herein, the main body 30a of the middle layer 30 is black. This ensures that, when a sample chamber 33 is optically read, the reading is not affected by spurious signals from neighbouring sample chambers 33, or other structures in the middle layer 30. That is, the black opaque material of the main body 30a of the middle layer 30 provides optical isolation for each sample chamber 33 and reduces optical cross-talk between neighbouring sample chambers 33.

The lower layer 40 comprises a flat planar disc. The lower layer 40 functions as an optical window for imaging of the sample chambers 33, and so has the property of being optically transparent to the wavelength(s) of light which are measured in the analysis.

The refractive index of the lower layer 40 is different from the refractive index of the contents of the sample chambers 33. In applications where the contents of the sample chambers 33 are imaged, such a feature allows the use of an autofocus system which detects the surface at which there is an interface between the lower layer 40 and the contents of the sample chambers 33, i.e. it detects the difference in refractive index of the lower layer 40 and the contents of the sample chambers 33. The lower layer 40 has a minimum thickness of 0.5 mm, as otherwise the autofocus unit may detect instead the surface at which there is an interface between the lower layer 40 and the air below, by detecting the difference in refractive index of the lower layer 40 and air.

To allow for rapid imaging with continuous focus, the lower layer 40 should be flat (i.e. the top and bottom surfaces of the lower layer 40 should be flat and parallel to one another). The surfaces of the lower layer 40 should be parallel within each sample chamber 33 to allow tracking autofocus, with a maximum deviation of the order of ±10 μm/cm. Any deviation from flatness across larger distances (for example, over a few centimetres) is less troublesome, as an autofocus system has more time to compensate for such defects. This goes for the flatness in the direction of travel during imaging. In the direction perpendicular to this, i.e. parallel to the width of the sample chambers, the flatness should be over the width of the imaged line, which in this example is 2 to 2.2 mm.

Figure 5:
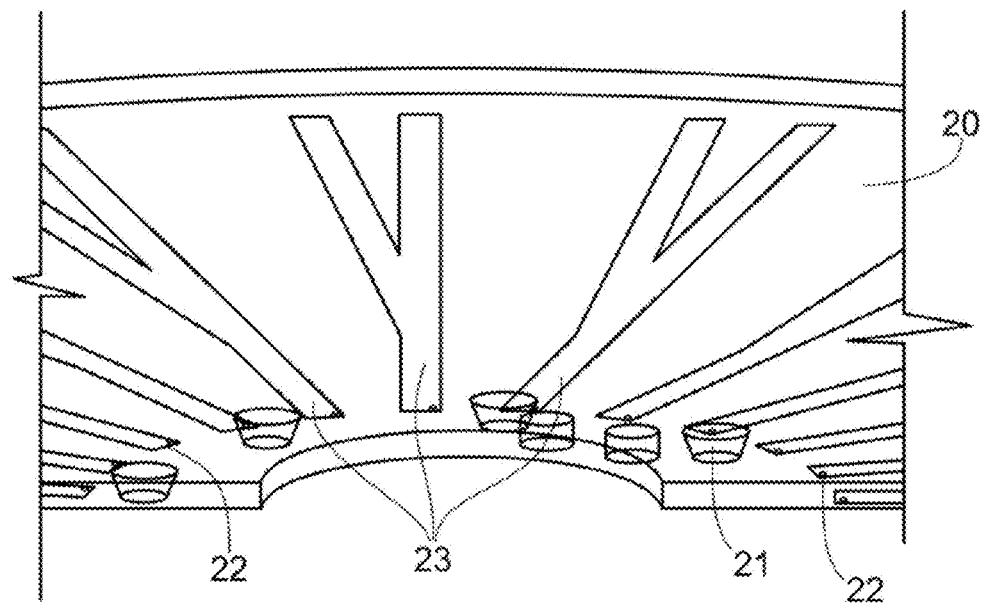
FIG. 5 shows an upper layer of the sample holder of FIG. 1.

The upper layer 20 covers the middle layer 30, and so acts as a lid which caps each of the sample chambers 33. Sample inlets 21 and gas vents 22 are provided in the upper layer 20, formed by through-holes extending all the way through the upper layer 20. These are best shown in FIG. 5. As further shown in this figure, the sample inlets 21 have a funnel shape (widest at the top surface of the upper layer, tapering to a minimum at the bottom surface of the upper layer) to provide a docking guide for an operator to dock a pipette to the sample inlet 21.

As shown in FIGS. 1 and 2, additional inlets 24 may be provided in the upper layer 20, to allow fluid to be introduced to the additional reservoirs 39 (shown in FIG. 3).

The bottom surface of the upper layer 20 (i.e. the surface of the upper layer 20 which faces the middle layer 30) comprises a micropillar array 23. The shape and positioning of the micropillar arrays are shown in FIGS. 1 and 5. From FIG. 1, it will be noted that the micropillar arrays 23 extend over the top of all of the sample chambers 33, over at least part of the periphery of the gas reservoirs 32, beneath a gas vent 22 and beneath a venting channel 37a extending from the waste reservoir 37. Gas exchange is possible between all of these locations, via the micropillar array.

From FIGS. 1 and 5 it will be appreciated that there are a plurality of micropillar arrays 23, each extending over a plurality of sample chambers 33. Each micropillar array 23 has a width slightly wider than the width of the sample chambers 33. The plurality of micropillar arrays 23 each extend in a broadly radial direction, following the radial lines of sample chambers.

In the embodiment of FIG. 5, the presence of the micropillars array 23 results in the bottom surface of the upper layer 20 covering the sample chambers 33 becoming hydrophobic. As a result, the bottom surface of the upper layer 20 covering the sample chambers 33 cannot be wetted by the sample in the sample chambers 33, and so the micropillar array acts to seal the sample in the sample chambers 33.

A second embodiment of the sample holder 10 is shown in FIGS. 6 to 11. The main differences between this embodiment and the previous embodiment are outlined below. For brevity, explanations of features which are identical to those in the preceding embodiment are not repeated here.

Figure 6B:
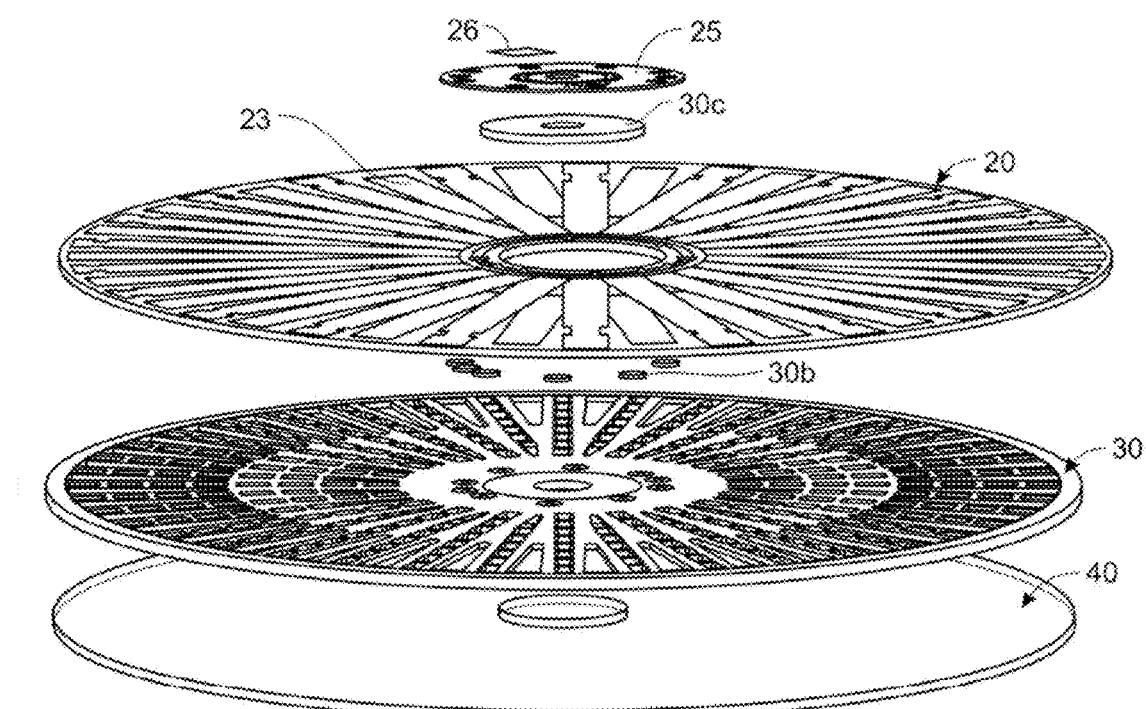
FIG. 6B shows the sample holder of FIG. 6A, in expanded view.
Figure 7:
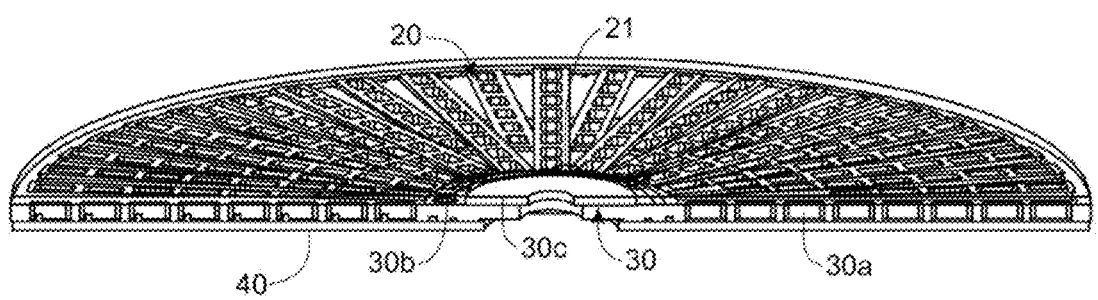
FIG. 7 shows a cut-away perspective view of the sample holder of FIG. 6.
Figure 8:
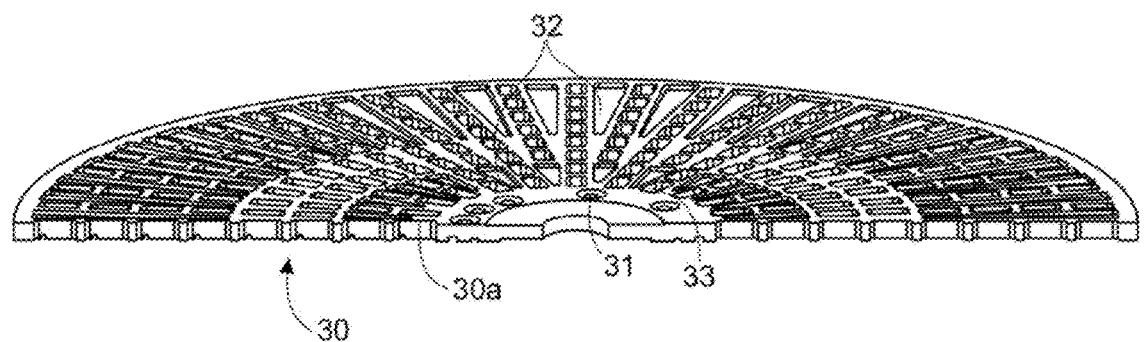
FIG. 8 shows a cut-away perspective view of a middle layer of the sample holder of FIG. 9.

FIG. 6B shows that the sample holder 10 may comprise (affixed to the upper layer 20) a label 25 and/or QR code 26. The label 25 and QR code may be provided as one single label.

In the configuration shown in FIG. 6B, the flexible membrane layer 30b comprises a plurality of smaller membranes, for example, one for each sample inlet to the sample holder 10. In contrast, in the preceding embodiment, one membrane 30b is provided, covering all of the sample inlets.

As will be appreciated from FIGS. 6 to 11, the fluidic networks in this embodiment do not comprise dedicated waste reservoirs 37, as were present in the previous embodiment. This is especially clear from FIGS. 9A to 9D, which show a fluidic network. In particular, FIG. 9A shows a top view of part of the middle layer of the sample holder, FIG. 9B shows a bottom view of part of the middle layer of the sample holder, and FIGS. 9C and 9D show respectively a close-up view of the top and bottom of the middle layer. In this embodiment every other gas reservoir 32a also serves as waste reservoir. Only a small portion of the volume of the gas reservoir 32a is used for waste. These gas reservoirs 32a are isolated from the sample chambers 33 by the micropillars array 23, and so waste in the gas reservoir 32a cannot contaminate the sample chambers 33. FIGS. 9C and 9D shown that the gas reservoir 32a is connected to the end of the fluid filling channel 34 via a through-hole 32b.

In contrast to the preceding embodiment, in this embodiment, there is no geometric restriction 36 between the end of the fluid filling channel 34 and the gas reservoir 32a. Instead, the fluid filling channel 34 itself acts as a flow restriction. The flow resistance within each sample chamber 33 is lower than the resistance in the fluid filling channel 34, therefore the sample chambers 33 will be filled first, before waste flows into the gas reservoir 32a.

FIG. 10C shows a partial cutaway perspective view of the middle layer of the sample holder of FIG. 6. This figure particularly shows that the additional reservoirs 39 are filled through corresponding inlets 39a, and inlet channels 39b (also shown in FIGS. 10A and 10B). They are vented via vent channel 39c. The same structure may also apply to the embodiment of FIG. 1.

FIG. 11 shows an upper layer of the sample holder of FIG. 6. Of note here is that some of the micropillar arrays 23 shown in FIG. 11 have a shape facilitating alignment with the sample chambers below, during manufacture of the sample holder. In this embodiment, every other micropillar array 23 (i.e. alternate micropillar arrays) comprises a narrowed portion 23b where the width of the micropillar array 23 narrows to be only slightly wider than the width of a sample chamber 33. This narrowed portion 23b is provided at a position radially along the micropillar array 23 to align with the radially outermost sample chamber 33. The narrowed portions 23b may then visually be rotationally aligned with the radially outermost sample chamber 33 prior to bonding.

Of further note is that FIG. 11 shows micropillar arrays 23 which extend only around the upper periphery of each sample chamber 33, not over the entire upper surface of the sample chamber 33. Parts 23c are not provided with micropillars. The micropillars arrays 23 nevertheless act to seal the sample in the sample chambers 33.

A third embodiment of the sample holder 10 is shown in FIGS. 12 to 18. The main differences between this embodiment and the previous embodiments are outlined below. For brevity, explanations of features which are identical to those in the preceding embodiment are not repeated here.

FIG. 12 shows that in this embodiment, the upper layer 20 in this case comprises a single, continuous micropillar array 23. The micropillar array 23 has a lobed shape, wherein each lobe covers one radial line of sample chambers 33. In this case, there are two different lengths of lobes, a longer lobe 23d and a shorter lobe 23e. The shorter lobes 23e do not extend radially inward as far as the longer lobes 23d. The shorter lobes 23e in this case cover a radial line of six sample chambers 33, whereas the longer lobes 23d cover a radial line of eight sample chambers. The lobes 23d, 23e overlap at their radially inward ends to form a continuously connected array.

The longer lobes 23d each overlie at their radially inward end two gas channels 32c. The gas channels 32c are channels formed in the top surface of the main body 30a of the middle layer 30. They run from underneath the lobes 23d to a gap 32d (discussed in more detail below) between an inner periphery of the upper layer 20 (i.e. the hole in the upper layer 20) and an outer periphery of the raised section 30d of the middle layer 30 (see FIG. 16A). The micropillar array 23 may thereby be vented; gas (for example, air) can move from the lobes 23d, 23e into the gas channels 32c, along the gas channel 32c and into the gap 32d, which is open to the atmosphere.

The main body 30a of the middle layer 30 may include features necessitated by the production method employed. When the main body 30a of the middle layer 30 is injection moulded, the main body 30a of the middle layer 30 may comprise one or more pockets for mould gates 60, where the material to be moulded (i.e. molten plastic, such as polystyrene or a cyclo-olefin polymer, for example Zeonor®) enters the form. In one example, three pockets for mould gates 60 are present in the middle layer. Similarly, the main body 30a of the middle layer 30 may comprise a plurality of ejector pin pockets 61 where ejector pins contacted the main body 30a of the middle layer to push it out of the moulding form. The pockets for mould gates 60 are shown in FIG. 12, and the ejector pin pockets 61 are shown in FIG. 13 (which shows a bottom surface of the middle layer of the sample holder of FIG. 12).

As shown in FIG. 13, this embodiment also differs from previous embodiments by virtue of differences in the fluidic filling channels. This is best seen in FIG. 14.

Firstly, each fluid filling channel 34 comprises an extra volume 34a provided in the middle layer to allow for different fill volumes of the sample and to allow for some liquid evaporation, without liquid evaporation from sample chambers 33. For example, if too much sample is supplied, excess sample may be contained by the extra volume 34a. The extra volume 34a is provided as a blind hole in the main body 30a of the middle layer 30, i.e. the main volume 34a is formed in the bottom surface of the middle layer 30, and does not reach all the way to the top surface of the middle layer. The extra volume 34a is located close to the inlet 31. For example, where the fluidic network comprises only one fluid filling channel, the extra volume 34a is located between the inlet 31 and the branch channel 35 closest to the inlet 31. Where the fluidic network comprises a plurality of fluid filling channels, the extra volume 34a is located between the inlet 31 and the point where the plurality of fluid filling channels split apart.

FIG. 14 shows two different configurations of fluidic network which alternate around the sample holder 10. Each fluidic network is connected to a separate inlet 31.

A first fluidic network connects to four radial lines of sample chambers 33. In this case, the radial lines have six or eight sample chambers, alternating (so from the top of FIG.

14, the uppermost radial line has six sample chambers 33, the neighbouring radial line has eight sample chambers 33, then the next has six sample chambers 33, and the final radial line connected to the fluidic network has eight sample chambers 33).

A second fluidic network connects to six radial lines of sample chambers 33. In this case, the radial lines have six or eight sample chambers, alternating (in a configuration with six sample chambers 33 in the first radial line, then eight in the next, then six, then eight, then six, then eight).

As is also clear from FIG. 14, each fluid filling channel 34 is shaped so as to have the effect of partially separating the plurality of sample chambers connected to the fluid filling channel into sub-groups. In a radial line of six sample chambers 33, the sample chambers are separated into two sub-groups 33a, 33b of three. In a radial line of eight sample chambers 33, the sample chambers are separated into two sub-groups 33c, 33d of four.

This may be useful, for example, in AST testing. For example, a first sub-group of the two may have a first antimicrobial agent deposited in each of the sample chambers in the first sub-group (at different concentrations in each sample chamber), and a second sub-group of the two may have a second antimicrobial agent (different from the first antimicrobial agent) deposited in each of the sample chambers in the second sub-group (at different concentrations in each sample chamber).

The fluid filling channel 34 separates the sub-groups by providing a long separation distance between the sub-groups, such that there is very low crosstalk between the two sub-groups.

One possible way of providing this separation is by providing a fluid filling channel 34 which doubles back on itself. Such a fluid filling channel has a hook shape, as is clear from FIG. 14.

Taking the two sub-groups 33a, 33b of three as an example, the radially inner sub-group 33a is connected (via respective branch channels 35) to an upstream part of the fluid filling channel 34, i.e. a part of the fluid filling channel running from the inlet 31 to roughly mid-way along the extent of the middle layer along its radius. After the first sub group 33a, the fluid filling channel 34 runs (with no sample chambers 33 connecting to it) towards the outer edge of the middle layer 30. Near the outer edge of the middle layer, the fluid filling channel turns back on itself, and run back towards the centre of the middle layer 30, stopping slightly outwardly of the point at which it continued on from the first sub-group 33a. The second sub-group 33b is distributed along this downstream return section, i.e. from the outer edge of the middle layer 30 to the end of the fluid filling channel 34.

As is also apparent from FIG. 14, this embodiment has no waste reservoirs (neither dedicated waste reservoirs nor gas reservoirs used as waste reservoirs) connected to the fluidic networks.

In this case, full filling of the sample chambers is ensured by first filling a calculated correct volume of liquid for the fluidic network, including at least most of the extra volume 34a. The liquid is followed by a small air volume to ensure full filling of the sample chambers 33. If the sample chambers 33 are fully filled before the entire air volume is dispensed, the post-liquid volume of air will compress, and then expand as the pipette tip is removed. This post-liquid "air cushion" should suffice to ensure filling of all sample chambers 33 without overfill/leakage.

There is also no "restriction" at the second end of the fluid filling channel; the second end is simply a closed end.

The inlets 31 shown in FIG. 14 may be covered with a label 25 (see FIG. 18). In use, the label may be pierced to allow sample to be introduced to the inlet 31.

The inlets 31 are provided in a raised section 30d (for example, an annular raised section) of the middle layer 30, described in more detail below.

FIG. 15 shows a different configuration of the magnetic metal layer 30c from the previous embodiments. The metal layer 30c in this case is slightly thicker than the main body 30a of the middle layer 30, such that it extends past the bottom surface of the main body 30a of the middle layer 30 (whilst remaining co-planar with the top surface of the main body 30a of the middle layer 30). The fact that the metal layer 30c extends past the bottom surface of the main body 30a of the middle layer 30 allows for easy alignment of the middle layer 30 and lower layer 40. The metal layer 30c may be overmoulded with the main body 30a of the middle layer 30.

The main body 30a of the middle layer 30 may comprise an annular raised section 30d extending outward from the central hole 12 in the middle layer 30. The inlets 31 to the fluidic networks and the inlets 39a to additional reservoirs 39 are formed in this raised portion.

A plurality of nodes 30e (visible in FIG. 16A)—for example, four nodes—project outwardly from the outer periphery of the annular raised section 30d. The upper layer 20 has a central hole sized to engage the nodes 30e around the annular raised section 30d, such that the upper layer 20 and middle layer 30 may be press-fit together and frictionally engaged. Once engaged in this way, the top surface of the upper layer 20 and the top surface of the annular raised section 30d are co-planar.

Except at the positions of the nodes 30e, there is a gap 32d (open to the atmosphere) between the inner periphery of the upper layer 20 (i.e. the hole in the upper layer 20) and the outer periphery of the annular raised section 30d. This gap 32d has a venting function, as discussed above in relation to venting of the micropillar array 23, and below in relation to venting of additional reservoirs 39.

Figures 16B, 16C:
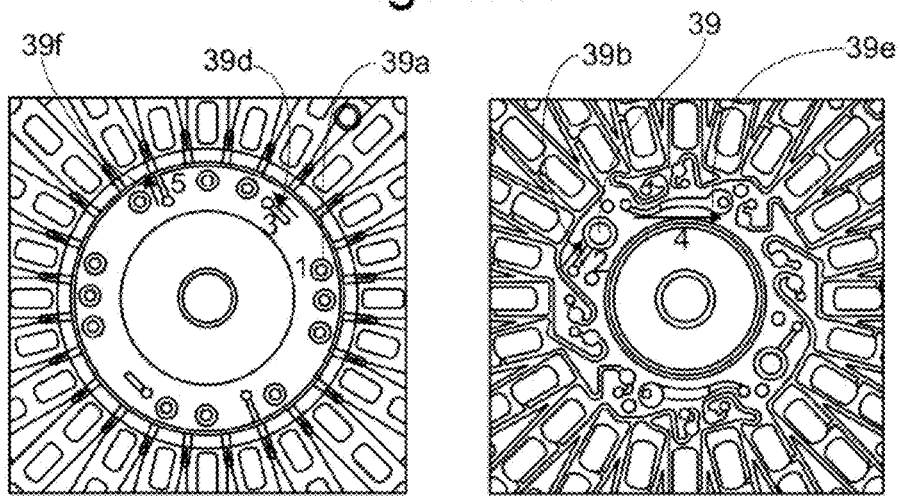
Figure 16D:
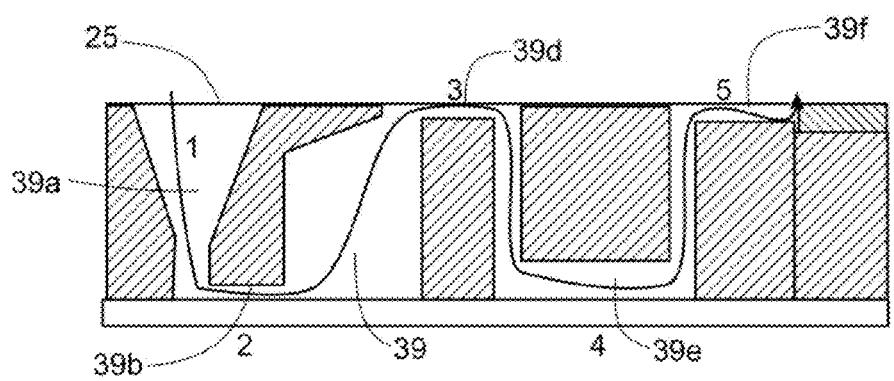

FIGS. 16A to 16B illustrate a different configuration of the additional reservoir 39 from that of previous embodiments. Each additional reservoir 39, for example those for receiving a sample for carrying out a concentration determination analysis, is connected to a liquid waste channel 39d. This liquid waste channel 39d receives excess liquid filled into the additional reservoir 39, to allow for variability in the amount of liquid introduced into the additional reservoir 39. The liquid waste channel 39d connects to a sub-reservoir 39e, in order to handle a larger amount of excess liquid. The sub-reservoir 39e comprises a connection to a gas channel 39f, to allow gas (air) to be vented as liquid is introduced into the additional reservoir 39. The gas channel 39f is connected to the gap 32d for venting to the atmosphere.

A more detailed explanation of the foregoing structure is as follows. The inlet 39a into the additional reservoir 39 is provided as a funnel-shaped through-hole—see point 1 on FIGS. 16B and 16D—which is wider at the top surface of the middle layer 30 and narrows towards the bottom surface of the middle layer 30. The bottom of the inlet 39a connects to an inlet channel 39b formed in the bottom surface of the middle layer 30—see point 2 on FIGS. 16C and 16D. The inlet channel 39b connects to the additional reservoir 39, and forms an entrance to the additional reservoir 39 on a first side (at the bottom) of the additional reservoir 39. The roof of the additional reservoir slopes upward from the first side to a second, opposite side, to help prevent air being trapped in the additional reservoir 39. On the second side, at the top of the additional reservoir 39 is an exit from the additional reservoir into a liquid waste channel 39*d*—see point 3 on FIGS. 16B and 16D. The liquid waste channel 39*d* is an open channel provided in the top surface of the middle layer 30. The liquid waste channel 39*d* runs across to a through-hole through the middle layer 30. The bottom of that through-hole opens into a first side of a sub-reservoir 39*e*—see point 4 on FIGS. 16C and 16D. The sub-reservoir 39*e* is provided as a broad channel in the bottom surface of the middle layer (not open to the top surface of the bottom layer). At the other end of the sub-reservoir 39*e*, opposite the first end, is another through-hole. This opens to a gas channel 39*f* (an open channel) on the top surface of the middle layer 30, which allows air to be vented—see point 5 on FIGS. 16B and 16D. The gas channel 39*f* runs to the gap 32*d* (see FIG. 16A) between the middle layer 30 and the upper layer 20 (i.e. the gap 32*d* between the inner periphery of the upper layer 20, and the outer periphery of the annular raised portion 30*d* of the middle layer), which is open to the atmosphere.

The inlet 39*a* and channels 39*d*, 39*f* are covered with a label 25 (see FIG. 18). In use, the label is pierced to allow sample to be introduced to the inlet.

The inlet 39*a* and channels 39*d*, 39*f* are provided in the annular raised section 30*d* of the middle layer 30, described above.

As shown in FIG. 17, the lower layer may comprise alignment and/or indexing markings. Here, alignment markings are used for alignment with markers in other layers, and indexing lines allow alignment of the sample holder in a specific rotation when it is being processed.

In this example, the markings are produced by "frosting" (a very shallow checkerboard pattern produced in the bottom surface of the lower layer during injection moulding of the lower layer). Other methods of producing the alignment and/or indexing markings may of course be used.

The alignment markings include a marking 43*a* at the outer edge of the lower layer, for alignment with a corresponding marking (for example a notch 38*b*, as shown in FIG. 10A) in the middle layer 30. Two further markings 43*b*, 43*c* may be provided, at different circumferential positions, such that the three markings 43*a*, 43*b*, 43*c* are unevenly spaced around the lower layer, to produce an asymmetry in the marking, eliminating the possibility of mounting the lower layer 40 to the middle layer 30 upside down.

Indexing lines are also provided, allowing alignment of the sample holder in a specific rotation when it is being processed. In this case, the indexing lines 44 are arranged along a radial line, rotationally positioned so that the does not intersect any sample chamber.

FIG. 18 shows a central part of the sample holder of FIG. 12, covered by a label 25. In this case, the label covers all inlets (for example, inlets 31 to fluid filling channels 34 and inlets 39*a* to additional reservoirs 39) into the sample holder until each inlet is pierced by the pipette 50 during sample introduction.

Features in the foregoing embodiments can freely be combined with other features from other embodiments, without restriction, except where the combination includes mutually exclusive features.

In the foregoing embodiments, the micropillars 23*a* forming the micropillar array 23 have a height of approximately 100 µm and a diameter of approximately 80 µm, in this example. The centre-centre distance (separation distance) between adjacent micropillars 23*a* is approximately 100 µm.

The micropillars 23*a* in this example have a frustoconical shape, as shown in FIGS. 22 and 23. Such a shape is advantageous as it is easily formed by injection moulding.

Figure 19A:
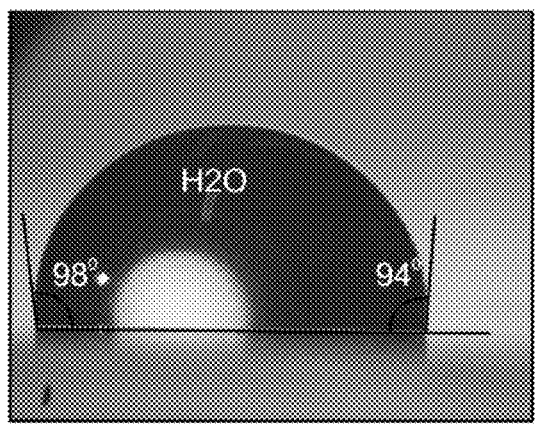
Figure 19B:
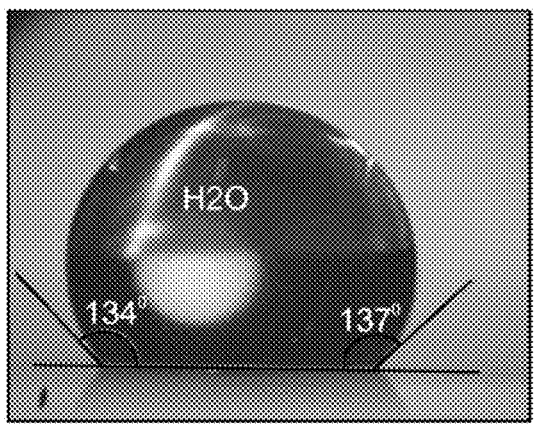
Figure 19C:
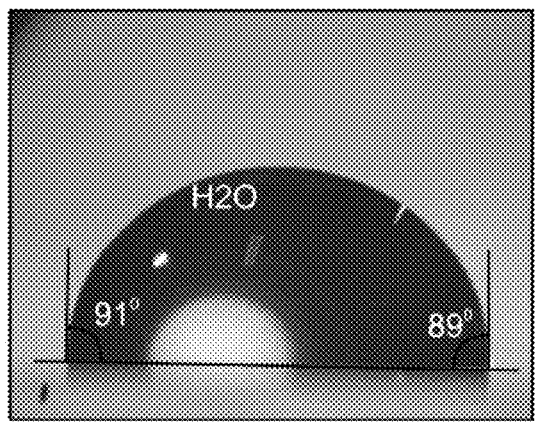
Figure 19D:
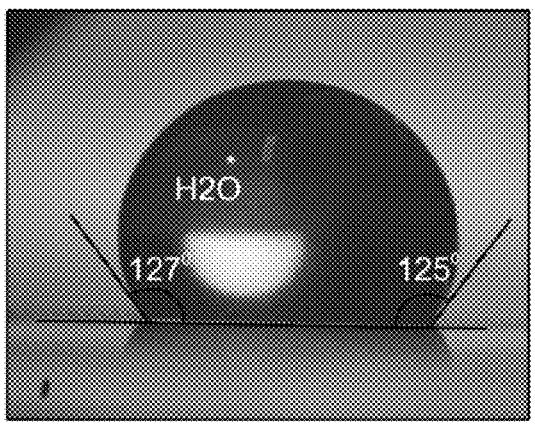

The effect of the micropillar array 23 in terms of the surface properties (i.e. hydrophobicity) of the bottom surface of the upper layer 20 is shown in FIGS. 19A to 19D. FIG. 19A shows a water droplet on a flat polystyrene surface (i.e. a polystyrene surface without a micropillar array). The contact angle of the water droplet with the surface is 94 to 98°. FIG. 19B shows a water droplet on the surface of a micropillar array formed of polystyrene. In this case, the contact angle of the water droplet with the surface is 125 to 127°. FIG. 19C shows a water droplet on a flat Zeonor® surface (i.e. a Zeonor® surface without a micropillar array). The contact angle of the water droplet with the surface is 89 to 91°. FIG. 19D shows a water droplet on the surface of a micropillar array formed of Zeonor®. In this case, the contact angle of the water droplet with the surface is 134 to 137°.

The upper layer 20 is at least semi-transparent in order to allow for the sample chambers 33 to be illuminated for imaging.

To manufacture the sample holder 10, the upper layer 20, main body 30*a* of the middle layer 30 and lower layer 40 are each produced by injection moulding polystyrene, to form the necessary structure of each layer. For example, the upper layer 20 may be moulded as a flat disc including through-holes for forming sample inlets 21 and gas vent 22. The main body 30*a* of the middle layer 30 may be moulded as a flat disc including through-holes for forming sample inlets 31, a plurality of sample chambers 33, and a plurality of waste reservoirs 37, blind holes for forming a plurality of gas reservoirs 32, and grooves for forming a plurality of fluid filling channels 34 and branch channels 35.

The lower layer 40 may be moulded as a flat disc including indentations forming focus-verification structures 41 (see FIG. 20). These may be aligned with one or more of the sample chambers 33, such that the focus-verification structures 41 are present in the base of one or more of the sample chambers 33. Alternatively, the focus-verification structures may be provided as a plurality of concentric circles, arranged so that a portion of each concentric circle is visible in the same relative position of each sample chamber.

The three layers 20, 30, 40 are joined together by laser welding to create a leak proof, irreversible bond along the welding pattern. FIGS. 21A to 21C show exemplary laser welds. FIGS. 21A and 21C show welds 42*a*, 42*b*, 42*c* between the lower layer 40 and middle layer 30, and FIG. 21B shows welds 28 between the upper layer 20 and middle layer 30.

FIG. 21C illustrates an exemplary bonding pattern used to bond the lower layer 40 to the middle layer 30. An outer seal weld 42*b* is provided round the outer edge of the sample holder 10. In this example, two inner seal welds 42*c* are provided round the inner edge of the sample holder 10. Then, a plurality of network welds 42*a* (also shown in FIG. 21A) are provided to prevent fluid leakage out of each fluidic network. Not all of the network welds are shown. Specifically, each network weld 42*a* is provided partially around the sample inlet 31, along the fluid filling channels 34 connected to the sample inlet 31, and partially around each sample chamber 33 in the fluidic network. The network welds 42*a* do not completely surround the sample chamber 33 to avoid welding closed the inlet to the sample chamber 33.

The inner and outer welds 42c, 42b are present for safety reasons, to decrease the risk of leakage out from the sample holder 10. These welds are therefore wider than the network welds 42a. Typically, the inner/outer welds 42c, 42b welds may have a width of the order of a few millimetres, for example 0.5 to 3 mm, optionally 1 to 2 mm. Additionally or alternatively, a plurality of welds may also be provided (for example, in FIG. 21D two inner welds 42c are provided).

The network welds 42a typically have a thickness of 0.1 to 0.6 mm, optionally 0.2 to 0.4 mm.

The positioning of the bonding may be used to control gas exchange within the sample holder 10 (for example, to allow gas exchange with the atmosphere, or only with gases provided in certain gas reservoirs), i.e. by isolating portions of the sample holder 10 from other portions, and/or from the atmosphere. This allows different conditions to be applied in different portions of the sample holder.

Where a bond is present between an area of the micropillar array 23 (on the upper layer 20) and the middle layer 30, only the micropillar tips are bonded to the middle layer 30, to maintain the spacing between the micropillars.

In use, the sample is supplied into the middle layer 30 via the sample inlet port 21 of the upper layer 20 and the inlet 31 of the middle layer, into the fluid filling channels 34. For example, the sample is supplied into the sample holder 10 via a pipette 50 (shown in FIG. 22). The pipette tip is docked to the sample inlets and pressurized by actuating the pipette plunger. Air present in the fluid filling channels 34, branch channels 35 and sample chambers 33 is evacuated through the micropillar array on the upper layer 20. When the liquid front reaches the micropillar surface in a sample chamber 33 it will stop, as the hydrophobic surface constitutes a barrier (see FIG. 23). Propagation of the sample liquid will instead continue in other parts of the fluid network (for example, other sample chambers 33 connected to the fluid filling channel 34 may fill up). When filling the sample holder of the first embodiment (shown in FIGS. 1 to 5), the geometric restriction 36 positioned at the end of each fluid filling channel 34, where the fluid filling channel 34 meets the waste reservoir 37, ensures that the liquid front stops at this position, as long as any sample chambers 33 remain to be filled (due to the hydrophobic nature of the restriction 36, which provides a wetting resistance). The restriction to the waste reservoir is greater than the inlet restriction to ensure all sample chambers 33 are filled.

When all sample chambers 33 connected to a given sample inlet 31 are full, the liquid front will pass through the geometric restriction 36.

When filling the sample holder of the second embodiment (shown in FIGS. 6 to 11), the restriction to fluid flow into the gas reservoirs 32a (which serve as waste reservoirs) is due to the restriction to flow imposed by the fluid filling channel 34 itself. There is no geometric restriction 36 in this embodiment. The flow resistance within each sample chamber 33 is lower than the resistance in the fluid filling channel 34, therefore the sample chambers 33 will be filled first, before waste flows into the gas reservoir 32a. When all sample chambers 33 connected to a given sample inlet 31 are full, the liquid front will pass through to the waste reservoir 32a.

The final step in the filling sequence is to evacuate the fluid filling channels 34. This is achieved by docking an air-filled pipette to the sample inlets 21, 31 and actuating the plunger. The liquid in the fluid filling channels 34 is then pushed through the geometric restriction 36 into the waste reservoir 37. This leaves the fluid filling channels 34 filled with air, and the branch channels 35 and sample chambers 33 filled with sample. Each sample chamber 33 (and associated branch channel 35) is therefore isolated from the other. Thus, there is no possibility of contamination between sample chambers 33.

As the branch channels 35 retain a small amount of sample (once the sample has been introduced into the sample holder 10), they can be used as a sample top-up reservoir to maintain the level of fluid in the sample chamber 33, in the event that some of the sample in the sample chamber 33 evaporates during the analysis.

The sample holder 10 is a single-use plastic device. One suitable use for the sample holder 10 is in antimicrobial susceptibility testing (AST). In such an analysis, a sample containing a pathogen is cultured in the presence of various antimicrobial substances at different concentrations. In this case, the antimicrobials are dispensed into the sample chambers and dried (for example, antimicrobials are provided in dried, liquid or lyophilised form), as part of the production process for manufacturing the sample holder 10. Each radial line of sample chambers 33 contains the same antimicrobial in different concentrations.

As mentioned above, focus-verification structures 41 (for example, pyramid-shaped indentations), may be provided in the lower layer 40—see FIG. 20. Such structures are described in Q-Linea AB's application PCT/EP2017/064715 (WO 2017/216314). The focus-verification structures may be provided in the bottom of each sample chamber 33, at the end of each channel 34, adjacent each sample chamber 33 or adjacent each fluid filling channel 34. In another arrangement, each channel 34 may have a plurality of associated focus-verification structures 41 spaced at set distances from the centre of the sample holder 10, such that the focus-verification structures 41 lie along concentric circles centred on the centre of the sample holder 10. The focus-verification structures 41 may be provided between adjacent sample chambers 33, spaced inwardly of the outer width of the sample chambers 33.

Alternatively, the focus-verification structures may be provided as a plurality of concentric circles, arranged so that a portion of each concentric circle is visible in the same relative position of each sample chamber.

As shown in FIG. 20, a collimated light beam perpendicular to the flat surface of the lower layer 40 in which the focus-verification structures are formed gives rise to total internal reflection on the sidewalls of the focus checking structure 41. In the case of a less than perfectly collimated beam, the reflection may not be total, but it is still sufficient for contrast detection as detailed below. As a result of the (total) internal reflection, when viewed from the top, the majority of the area of the focus-verification structure 41 appears dark. If focused exactly on the base of the focus-verification structure 41, where the sidewalls meet and form the point of the pyramid indentation, then a bright spot appears. The contrast between this bright spot and the darker area of the surrounding part of the indentation changes rapidly with changing focal plane.

FIGS. 24A and 24B show a system for microscopy-based analysis of samples. The sample holder 10 of the present invention may be used in such a system. Use of the sample holder 10 is not restricted to use in such a system, however.

The systems shown in FIGS. 24A and 24B comprise a device for microscopy-based analysis of samples comprising a line camera 110, a tracking autofocus system 115, a dichroic mirror 120, an objective lens 125, an illumination light source 130, a band-pass filter 131, a condenser 132, and a tube lens 140. The two systems in FIGS. 24A and 24B are very similar, that the difference being that the location of the line camera 110 (and tube lens 140) and autofocus system 115 are swapped.

In one example, the line camera 110 is a Linea LA-CM-16K05A (comprising a CMOS digital image sensor) manufactured by Teledyne DALSA, coupled with an XTIUM-CL MX4 frame grabber (not shown), also by Teledyne DALSA. The camera array size is 1×16,384 pixels, with each pixel being 3.5 µm×3.5 µm. The line width is therefore 3.5 µm, and its length is 57.7 mm. Only a portion of this length may be used, in practice. The autofocus system 115 comprises an ATF6 SYS system, from WDI WISE Device Inc., comprising the ATF6 SWIFT digital autofocus system (with laser wavelength of 785 nm) and an MCZ controller for controlling the position of the objective lens 125 in the z-direction. The objective lens 125 is a N10X-PF lens (10× magnification, NA 0.3), manufactured by Nikon. The dichroic mirror 120 is a 662 nm edge BrightLine single-edge imaging-flat dichroic beamsplitter manufactured by Semrock. The light source 130 comprises an LED light source Luxeon LXZ1-PX01 (with central wavelength of about 556-569 nm), a condenser 132, along with a 560/94 nm BrightLine® single-band bandpass filter 131, manufactured by Semrock. The tube lens 140 is an ITL200 tube lens, from Thorlabs, with a focal length of 200 mm. The condenser 132 produces an illuminated area in the plane of the bottom of the sample chamber 33 at the imaging location of approximately 8×8 mm, with the central 5×5 mm area having an intensity variation less than approximately ±10%. The tube lens 140 focuses the collimated beam coming out of the objective 125 onto the line camera 110. The tube lens 140 is matched to the objective 125 to achieve a magnification of 10×.

The system further comprises a sample holder 10, as described above. The sample holder 10 is received by a support 150 (shown in FIG. 25) configured to receive the sample holder 10. The support 150 comprises a platform 152 comprising a recessed region 151 shaped to conform to the outer dimensions of the sample holder, such that, when placed within the recessed region, the sample holder cannot move laterally.

The platform 152 is provided on linear tracks 156a, 156b attached to the support, and a motor may be provided to drive the platform in either direction along the tracks. The motor (not shown) may drive movement of the platform along the tracks via a rack and pinion arrangement (not shown), for example.

The platform 152 comprises a platform lid 153 which, particularly during imaging, holds the sample holder 10 in a fixed position with respect to the vertical axis, i.e. such that the sample holder 10 does not move upwardly or downwardly.

The platform lid 153 is hingedly connected to the platform, so that it can pivot upwardly and away from the platform 152 about the hinged connection. In particular, the platform lid 153 is configured to move in this way when the platform 152 is translated to an extreme position at one end of the linear tracks 156a, 156b (to the far right, as shown in FIG. 25). This movement is the result of the platform lid 153 engaging with a guide rail (not shown), shaped so as to lift the platform lid 153 at the extreme position.

The sample holder 10 is loaded from above onto the support 150 (i.e. into the recessed region 151 of the platform 152) at the extreme position. In this position, the sample holder 10 rests on the recessed region 151 and is prevented from lateral movement by the recessed region 151. As the platform 152 moves from the extreme position, the platform lid 153 is guided down by the guide rail to press down on the sample holder 10, so that the sample holder 10 is prevented from movement upwardly by the downward force applied by the platform lid 153. That is, the platform lid 153 provides a vertical clamping function. The sample holder 10 is prevented from movement downwardly by being supported by the recessed region 151.

The support comprises a through-hole 154, below the plane at which the sample holder 10 is supported, which allows a portion of the sample holder 10 to be imaged by the line camera 10, from below.

In order to bring different radial lines of sample chambers 33 into line with the line camera 110 for imaging, the support 150 comprises a drive wheel 157 configured to rotate the sample holder 10 (about a vertical axis of the sample holder 10). When a sample holder 10 is held in the support 150, the drive wheel 157 is located adjacent to the rim of the sample holder 10, to frictionally engage the rim of the sample holder 10. The drive wheel 157 is pressed to the rim using a spring action. The drive wheel is driven by a second motor 155, via a drive belt (not shown).

The drive wheel 157 is configured to disengage from the rim of the sample holder 10 (i.e. the spring action pressing the drive wheel 157 to the rim of the sample holder 10 is relaxed) when the platform 152 is translated to the extreme position at the right-hand end (as shown in FIG. 25) of the linear tracks 156a, 156b. The drive wheel 157 is configured to engage with the rim of the sample holder 10 when the platform 152 is translated away from the extreme position. The drive wheel 157 is configured to rotate the sample holder 10 at a speed of approximately 30° per second.

The support 150 is configured to align the sample holder 10 in a specific position such that the starting position for the imaging is known. The support 150 comprises a dedicated detector (for example, a photodetector, not shown) configured to detect a single alignment structure 38a (see FIG. 1) which is present on the sample holder 10 at a distance from the centre of the sample holder 10 where no other structures are present. The single alignment 38a marker comprises a through-hole through the middle layer 30, similar to the through-holes which form the sample chambers 33, but smaller in size. Alternatively, the alignment marker may be an indexing line provided on the lower layer. The indexing line may be arranged along a radial line, rotationally positioned so that it does not intersect any sample chamber.

Alternatively or additionally, an alignment structure 38b (shown in FIG. 10A) may be provided, which is a notch in the outer edge of the middle layer 30. This notch 38b may be detected by an IR fork sensor, for example provided on the support 150.

The alignment or indexing structure(s) define(s) the absolute position, and then a predetermined offset gives the rotational position of the starting imaging position. The system can find the starting position for the imaging to within ±500 µm, as measured at the outermost sample chamber.

In the use of the device, the sample holder 10 is provided with appropriate samples in sample chambers 33 and images of the samples are gathered using the line camera 110.

Referring to FIG. 24A again, in use, light from the illumination source 130 is incident onto the sample holder 10 from above (via the band-pass filter 131 and condenser 132). The light passes through the sample chambers 33 of the sample holder 10, and is collected by the objective lens 125. After passing through the objective lens 125, the light reflects from the dichroic mirror 120, passes through the tube lens 140, and is then imaged by the line camera 110.

Similarly, in the system shown in FIG. 24B, in use, light from the illumination source 130 is incident onto the sample holder 10 from above (via the band-pass filter 131) and condenser 132. The light passes through the sample chambers 33 of the sample holder 10, and is collected by the objective lens 125. After passing through the objective lens 125, the light passes through the dichroic mirror 120, passes through the tube lens 140, and is then imaged by the line camera 110.

The sample holder 10 is moved in a first linear direction in the horizontal plane, such that the imaging line of the line camera 110 successively images different lines perpendicular to the radial line along which the sample chambers 33 are distributed.

The speed at which the sample holder is translated is, in this example, matched to the imaging rate (line rate) of the line camera, such that the resultant image is not distorted. The speed s of the linear movement of the sample holder is given by:

$$s = \frac{\text{pixel width} \times \text{line camera imaging rate}}{\text{magnification}}$$

Here, the pixel width is 3.5 μm, the line camera imaging rate is 48 kHz and the magnification is 10×. This gives a speed s of 16.8 mm/s. This allows imaging of 50 radial lines, each of 50 mm length, within 6 minutes (including the time taken for rotation to each new radial line, and data transfers). A sample holder 10 comprising 384 sample chambers can be fully scanned in 7 minutes. The total analysis time per sample chamber, including movement to the sample chamber, adjusting the focal plane during imaging, and acquiring images within the sample chamber is less than 2 seconds.

Following the completion of the translational movement of the sample holder 10, the sample holder 10 is rotated by the support 150 in order to bring another radial line of sample chambers 33 into alignment with the imaging line of the line camera 110. The sample holder 10 is then translated in a linear direction in the opposite to the first linear direction, to image the second radial line of sample chambers.

The autofocus system 115 comprises a laser light source (not shown) with wavelength of 785 nm. The laser light 115*a* passes through the dichroic mirror 120 and the objective lens 125 (in the opposite direction to the light gathered by the objective lens 125 from the sample chambers 33), to be incident onto a bottom surface of the sample holder 10. The autofocus system 115 sets the focal plane at the bottom surface of the sample chambers 33 in the sample holder. The focal plane of the line camera 110 may be set at a predetermined upward offset therefrom (such that the focal plane lies at a plane within the sample chamber 33, above and parallel to the bottom surface of the sample chamber 33), by offsetting the line camera 110 along the optical axis (by between 0 mm and 20 mm).

The autofocus system 115 can adjust the focal position (if necessary) every 0.15 ms. This allows the autofocus system 115 to recheck the focal position approximately every 7 lines read by the line camera 110 (which has an imaging rate of 48 kHz). If the focal position needs to be adjusted, the autofocus system 115 outputs a signal which causes the lens holder to translate the objective lens 125 in order to adjust the focal plane. The lens holder translates the objective lens 125 along an axis parallel to a plane of the support 150, with a precision of 1 μm. Movement of the lens holder is driven by a linear actuator (not shown). To image a single sample chamber 33, the line camera 110 may capture thousands of lines (for example, between 10,000 and 15,000), and so the focal plane may be adjusted by the autofocus system 115 hundreds or thousands of times, across each sample chamber 33. Any non-uniformity in the base of the sample chamber 33 can therefore be accounted for in the imaging process.

As a radial line of sample chambers 33 is imaged by the line camera 110, a composite image comprising the plurality of imaged lines is built up. The composite image obtained by the line camera 110 includes all of the sample chambers 33 along the radial line. This composite image may be processed by an image processing algorithm to split the composite into separate image areas, each including one sample chamber 33, for example.

As explained above, as the line of sample chambers 33 is imaged by the line camera 110, a composite image comprising the plurality of imaged lines is built up. The composite image obtained by the line camera 110 includes all of the sample chambers 33 and focus-verification structures 41 along the channel 34. This composite image may be processed by an image processing algorithm to split the composite into separate image areas, each including a sample chamber 33 and at least one focus-verification structure 41. In one example, the focus-verification structure 41 associated with a given sample chamber 33 comprises two pyramid indentations at each end of the sample chamber 33. In another example, there is a focus-verification structure 41 comprising four pyramid indentations 30 at the end of each sample chamber 33. In each case the geometry (i.e. layout of the pyramid indentations) may be the same, but the subsequent association of a focus-verification structure 41 with a sample chamber 33 in the imaging processing is different. In another example, the focus-verification structures are provided as a plurality of concentric circles arranged so that a portion of each concentric circle is visible in the same relative position of each sample chamber.

An image analysis system may check the images to determine if they are in focus by identifying the focus-verification structures 41 and checking whether or not they are in focus (as described for example in Q-Linea AB's application PCT/EP2017/064711 (WO 2017/216310)). If any of the images are not in focus then an indication can be given to the user and/or remedial action can be taken.

An image analysis system may receive the images taken by the system, and may carry out further image analysis, for example to determine the presence, absence, or amount of microscopic objects and/or to determine the type of microscopic objects (for example, as disclosed in Q-Linea AB's application PCT/EP2017/064713 (WO 2017/216312)).

Referring to FIGS. 26A to 26C, in some embodiments, the upper layer 20 of the sample holder 10 may be optically active, and may cause non-uniformity in the light incident onto the sample chambers 33. In particular, the micropillars on the upper layer 20 refract or block light so that the illumination intensity as perceived over the imaged areas is not even, but shows variations dependent on the shape and size of the micropillars. Such variations may be detrimental to the image, and subsequent image processing. To counteract this, a diffuser 160 may be positioned between the illumination source 130 and the upper layer 20 of the sample holder 10 (as shown in FIG. 26B). The diffuser may be an optical diffuser which diffuses the light evenly, or it may be an engineered diffuser comprising an engineered surface having structures designed to cancel out the light intensity variations caused by the micropillars. Alternatively, a plurality of light sources 130' may be provided (as shown in FIG. 26C), positioned to provide different path lengths for illumination of the sample chambers. The diffuser 160 or plurality of light sources 130' act to provide a more even illumination to the sample chambers 33.

The following clauses set out features of the invention which may not presently be claimed in this application, but which may form the basis for future amendment or a divisional application.

1. A sample holder comprising:
   an upper layer;
   a lower layer;
   a middle layer between the upper and lower layers; and
   a sample chamber formed by a through-hole in the middle layer, covered at its upper extent by a portion of the bottom surface of the upper layer, and at its lower extent by a portion of the top surface of the lower layer,
   wherein at least part of the bottom surface of the upper layer overlapping a portion of a top periphery of the sample chamber comprises a hydrophobic surface, wherein a contact angle of a water droplet on the hydrophobic surface exceeds 110°.

2. A sample holder comprising:
   a sample chamber;
   a gas reservoir; and
   an upper layer covering over the sample chamber and gas reservoir,
   wherein a bottom surface of the upper layer comprises a microstructure array which overlies at least a portion of a top periphery of the sample chamber,
   and wherein the microstructure array is in communication with a gas path which extends to the gas reservoir, to allow gas exchange between the sample chamber and gas reservoir.

3. A sample holder comprising a fluidic network comprising an inlet, a fluid filling channel, and a waste reservoir,
   wherein the fluid filling channel has a first end and a second end, the first end being connected to the inlet, and the second end being connected to the waste reservoir,
   wherein the fluidic network further comprises a plurality of sample chambers, each connected to receive sample liquid from the fluid filling channel via a respective branch channel branching off from the fluid filling channel, and
   wherein a restriction to fluid flow is provided at the second end of the fluid filling channel, or wherein the fluid filling channel itself acts as a restriction to fluid flow into the waste reservoir.

4. A sample chamber according to clause 1 or 2, wherein the sample holder comprises a fluidic network comprising an inlet, a fluid filling channel, and a waste reservoir, wherein the fluid filling channel has a first end and a second end, the first end being connected to the inlet, and the second end of being connected to the waste reservoir, wherein the sample chamber is connected to the fluid filling channel via a branch channel branching off from the fluid filling channel, optionally wherein the waste reservoir may be a gas reservoir.

5. A sample chamber according to clause 4, wherein a restriction to fluid flow is provided at the second end of the fluid filling channel.

6. A sample chamber according to clause 4 or 5, wherein the fluidic network comprises a plurality of sample chambers, each connected to the fluid filling channel via a respective branch channel of a plurality of branch channels branching off from the fluid filling channel.

7. A sample holder according clause 1 or any of clauses 4 to 6 when dependent from clause 1, wherein the hydrophobic surface is formed from a microstructure array, and/or wherein the hydrophobic surface is amphiphobic.

8. A sample holder according to clause 1 or any of clauses 4 to 7 when dependent from clause 1, wherein the sample holder comprises a gas reservoir.

9. A sample holder according to clause 8 when dependent from clause 7, wherein the microstructure array is in communication with a gas path which extends to the gas reservoir, to allow gas exchange between the sample chamber and gas reservoir.

10. A sample holder according to clause 2 or any of clauses 4 to 6 when dependent from clause 2, wherein the microstructure array forms a hydrophobic surface, optionally wherein the hydrophobic surface is an amphiphobic surface.

11. A sample holder according to any clause 2, or any of clauses 4 to 6 when dependent from clause 2, or clause 10, wherein the sample holder comprises a middle layer, wherein the sample chamber is formed as a through-hole in the middle layer.

12. A sample holder according to clause 2, or any of clauses 4 to 6 when dependent from clause 2, or clauses 10 or 11, wherein the sample holder comprises a lower layer, wherein the sample chamber is bounded at its lower extent by a portion of a top surface of the lower layer.

13. A sample holder according to clause 3, wherein the sample holder comprises an upper layer, a middle layer and a lower layer.

14. A sample holder according to clause 13, wherein the sample chamber is formed by a through-hole in the middle layer, covered at its upper extent by a portion of the bottom surface of the upper layer, and at its lower extent by a portion of the top surface of the lower layer.

15. A sample holder according to clause 14, wherein at least part of the bottom surface of the upper layer overlapping at least a portion of a top periphery of the sample chamber comprises a hydrophobic surface, optionally wherein the hydrophobic surface is an amphiphobic surface.

16. A sample holder according to clause 14 or 15, wherein at least part of the bottom surface of the upper layer overlapping at least a portion of a top periphery of the sample chamber comprises a microstructure array.

17. A sample holder according to any of clauses 3, or 14 to 16, wherein the sample holder comprises a gas reservoir, and optionally wherein the gas reservoir is also used as a waste reservoir.

18. A sample holder according to clause 17 when dependent from clause 16, wherein the microstructure array is in communication with a gas path which extends to the gas reservoir, to allow gas exchange between the sample chamber and gas reservoir.

19. A sample holder according to clause 2, 9 or 18, wherein the microstructure array overlies at least a portion of the top periphery of the sample chamber at a first position, and overlies at least a portion of a top periphery of the gas reservoir at a second position, and extends between the first position and the second position, such that the gas path is formed by the microstructure array,
   or wherein the gas path comprises a groove in the upper layer or middle layer, which is not provided with microstructures, extending from the microstructure array to at least a portion of a top periphery of the gas reservoir.

20. A sample holder according to clause 2, 9, 18 or 19, wherein the gas reservoir comprises a specific gas or gas mixture, different from air, which is selected so as to provide a particular analysis condition in the sample chamber, and/or wherein the gas reservoir is isolated from the atmosphere, and/or wherein the sample chamber is isolated from the atmosphere.

21. A sample holder according to clause 1, 10 or 15 wherein the hydrophobic surface extends around the entire top periphery of the sample chamber, optionally wherein the hydrophobic surface is amphiphobic.

22. A sample holder according to clause 21, wherein the hydrophobic surface extends across the whole of the upper surface of the sample chamber, optionally wherein the hydrophobic surface is amphiphobic.

23. A sample holder according to clause 21 or 22, wherein the sample chamber is sealed with respect to outward liquid flow at its top periphery by the hydrophobic surface, optionally wherein the hydrophobic surface is amphiphobic.

24. A sample holder according to clause 1, 11 or 13, wherein the sample chamber is partially sealed with respect to outward liquid flow at its top periphery by a bonding pattern which joins the middle layer to the upper layer.

25. A sample holder according to any preceding clause, wherein the sample chamber comprises an opening, optionally at its bottom periphery, for allowing a liquid sample to be supplied into the sample chamber.

26. A sample holder according to clause 1, 12 or 14, wherein the sample chamber is sealed with respect to outward liquid flow at its bottom periphery by a bonding pattern which joins the middle layer to the lower layer.

27. A sample holder according to any preceding clause, wherein the sample holder comprises a gas vent.

28. A sample holder according to clause 27 when dependent from clauses 1, 2 or 13, wherein the gas vent is formed as a through-hole in the upper layer.

29. A sample holder according to clause 27 when dependent from clause 2, 7 or 16, wherein the gas vent opens into an area provided with a microstructure array, such that the microstructure array provides a gas connection between the sample chamber and the gas vent.

30. A sample holder according to clause 27 when dependent from clause 2, 9 or 18, wherein the microstructure array provides a gas connection between the gas reservoir and gas vent, and/or wherein the gas reservoir contains air.

31. A sample holder according to clause 2, 9, 18, 19, or 30, wherein the sample holder comprises a plurality of gas reservoirs.

32. A sample holder according to any of clauses 2, 7 or 16, wherein the microstructures which form the microstructure array are tapered, and optionally have a broadly frustoconical shape, and/or have an overhanging shape.

33. A sample holder according to any of clauses 2, 7, 16 or 32, wherein the microstructure array is formed from a hydrophobic material, optionally wherein the microstructure array formed from a hydrophobic material is mechanically or chemically modified to provide an amphiphobic microstructure array.

34. A sample holder according to clause 7 when dependent from clause 4, clause 4 when dependent from clause 2, or clause 16, wherein the microstructure array optionally covers at least a portion of the top periphery of each sample chamber in the fluidic network.

35. A sample holder according to clause 34, wherein the microstructure array extends to an area over a gas reservoir, and/or an area over a gas path connected to a gas reservoir, and/or an area beneath a gas vent, and/or an area above a venting channel connected to a waste reservoir, and/or an area above a waste reservoir.

36. A sample holder according to any of clauses 7, 11, 16, 34 or 35, wherein the middle layer is joined to the upper layer with a bonding pattern which isolates a microstructure array from the atmosphere.

37. A sample holder according to any of clauses 2, 7, 16, 32 or 33, wherein the sample holder comprises a plurality of spatially separated microstructure arrays.

38. A sample holder according to any of clauses 3, 4, 34 or 35, comprising a plurality of fluidic networks.

39. A sample holder according to clause 38 when dependent from clause 37, wherein a plurality of separate microstructure arrays are provided, and optionally one microstructure array serves one fluidic network.

40. A sample holder according to any preceding clause, wherein the sample holder comprises a plurality of sample chambers.

41. A sample holder according to clause 3 or 5, wherein the degree of the restriction to flow presented by the geometric restriction is chosen to ensure that the sample front stops at this position, as long as any sample chambers upstream of the restriction remain to be filled.

42. A sample holder according to any of clauses 1, 2 or 13, wherein the upper layer includes a through-hole to provide a sample inlet port.

43. A sample holder according to clause 42, wherein the sample inlet port comprises a self-closing seal which is openable to allow sample to be dispensed through the sample inlet port.

44. A sample holder according to clause 42 or 43, wherein the sample inlet port comprises a docking guide, wherein optionally the docking guide takes the form that the sample inlet port has a funnel shape, such that the sample inlet port optionally widens at its upper end and tapers down to a minimum at its lower end.

45. A sample holder according to clause 1, 11 or 13, wherein the middle layer comprises an opaque, optionally black, material.

46. A sample holder according to clause 1, 2, or 13, wherein the upper layer is at semi-transparent or transparent.

47. A sample holder according to clause 1, 12, or 13, wherein the lower layer is transparent to a wavelength(s) of light which is/are measured in the analysis which makes use of the sample holder.

48. A sample holder according to any preceding clause, comprising a flexible membrane layer, or a plurality of flexible membranes.

49. A sample holder according to clause 48, wherein the flexible membrane layer comprises holes or slits therein to form self-closing seals for inlets to the sample holder, or wherein each of the plurality of flexible membranes comprises a hole or slit therein to form a self-closing seal for an inlet to the sample holder.

50. A sample holder according to any preceding clause, comprising a magnetic metal layer.

51. A sample holder according to any preceding clause, wherein the sample holder comprises an alignment marker which is present on the sample holder at a distance from the centre of the sample holder where no other structures are present, optionally wherein the alignment marker comprises a through-hole in a or the middle layer of the sample holder, and/or comprises a notch in the outer edge of a or the middle layer of the sample holder.

52. A sample holder according to any preceding clause, comprising an additional reservoir, or a plurality of additional reservoirs, for example for receiving a sample for carrying out a concentration determination analysis.

53. A sample holder according to any preceding clause, comprising the sample, which optionally includes microscopic objects contained in a sample fluid, wherein for example the microscopic objects are cells, bacteria, viruses, fungal pathogens or macromolecules.

54. A sample holder according to any preceding clause comprising a plurality of antimicrobial agents at a plurality of concentrations, for use in antibiotic susceptibility testing.
55. A sample holder according to any preceding clause, wherein the sample holder is a consumable single-use product that can be disposed of after use.
56. A method of manufacturing an sample holder according to any preceding clause, comprising: injection moulding an upper layer, middle layer, and lower layer; joining the upper surface of the lower layer to the lower surface of the middle layer; and joining the lower surface of the upper layer to the upper surface of the middle layer.
57. A method according to clause 56, wherein the step of joining the upper surface of the lower layer to the lower surface of the middle layer includes producing a pattern of bonding such that a portion of the sample holder is isolated from the atmosphere.
58. A method according to clause 56 or 57 wherein the steps of joining the upper surface of the lower layer to the lower surface of the middle layer and joining the lower surface of the upper layer to the upper surface of the middle layer includes joining the layers using a welding process, or by using glue or solvent bonding.
59. A method according to any of clauses 56 to 58, wherein the steps of joining the upper surface of the lower layer to the lower surface of the middle layer and joining the lower surface of the upper layer to the upper surface of the middle layer includes joining the layers using laser welding.
60. A method according to any of clauses 56 to 59, comprising treating parts of the sample holder to make them more hydrophobic.
61. A method according to any of clauses 56 to 60, comprising treating parts of the sample holder to make them more hydrophilic.
62. A method according to any of clauses 56 to 61, comprising depositing a substance into some or all of the sample chambers, optionally after the step of joining the upper surface of the lower layer to the lower surface of the middle layer, and prior to the step of joining the lower surface of the upper layer to the upper surface of the middle layer.
63. A method according to clause 62, wherein the substance is deposited in different amounts in a plurality of sample chambers,
64. A method according to clauses 62 or 63, wherein the substance is an antimicrobial agent.
65. A method according to any of clauses 56 to 64, comprising forming a microstructure array on the upper layer to form a hydrophobic surface, and optionally modifying the microstructure array mechanically or chemically to form an amphiphobic surface.

The invention claimed is:
1. A sample holder comprising:
a sample chamber;
a gas reservoir;
an upper layer covering over the sample chamber and gas reservoir,
a middle layer, wherein the sample chamber is formed as a through-hole in the middle layer; and
a lower layer, wherein the middle layer is between the upper layer and the lower layer, and wherein the sample chamber is bounded at its lower extent by a portion of a top surface of the lower layer;
wherein a bottom surface of the upper layer comprises a microstructure array which overlies at least a portion of a top periphery of the sample chamber,
wherein the microstructure array is in communication with a gas path which extends to the gas reservoir, to allow gas exchange between the sample chamber and the gas reservoir and wherein the microstructure array forms a hydrophobic surface, such that in use it is not possible for liquid in the sample chamber to escape via the gas path.
2. The sample holder according to claim 1, wherein the microstructure array overlies at least a portion of the top periphery of the sample chamber at a first position, and overlies at least a portion of a top periphery of the gas reservoir at a second position, and extends between the first position and the second position, such that the gas path is formed by the microstructure array,
or wherein the gas path comprises a groove in the upper layer, which is not provided with microstructures, extending from the microstructure array to at least a portion of a top periphery of the gas reservoir.
3. The sample holder according claim 1, wherein the gas path comprises a groove in the middle layer, extending from the microstructure array to at least a portion of a top periphery of the gas reservoir.
4. The sample holder according to claim 1, wherein the middle layer comprises a raised section, and the upper layer comprises a hole which fits around the raised section of the middle layer, wherein a gap is provided between an outer periphery of the raised section of the middle layer and an inner periphery of the upper layer, and wherein the gap is open to the atmosphere.
5. The sample holder according to claim 4, wherein a gas channel connects the microstructure array to the gap,
wherein the gas channel is either:
a channel in the top surface of the middle layer, which extends from underneath the microstructure array to the gap,
or a channel in the bottom surface of the upper layer, which is not provided with microstructures, and which opens into the microstructure array at a first end and into the gap at a second end.
6. The sample holder according to claim 1, wherein the middle layer is joined to the upper layer with a bonding pattern which isolates the microstructure array from the atmosphere.
7. The sample holder according to claim 1, wherein the sample chamber is sealed with respect to outward liquid flow at its top periphery by a combination of the hydrophobic surface and a bonding pattern which joins the middle layer to the upper layer.
8. The sample holder according to claim 1, wherein the lower layer is transparent to a wavelength(s) of light which is/are measured in the analysis which makes use of the sample holder, and wherein the upper layer is at least semi-transparent or transparent.
9. The sample holder according to claim 1, wherein the sample chamber is sealed with respect to outward liquid flow at its bottom periphery by a bonding pattern which joins the middle layer to the lower layer, and wherein the sample chamber comprises an opening at its bottom periphery, for allowing a liquid sample to be supplied into the sample chamber.
10. The sample holder according to claim 1, wherein the sample holder comprises a gas vent formed as a through-hole in the upper layer.
11. The sample holder according to claim 10, wherein the gas vent opens into an area provided with the microstructure array, such that the microstructure array provides a gas connection between the sample chamber and the gas vent.

12. The sample holder according to claim 10, wherein the microstructure array provides a gas connection between the gas reservoir and the gas vent, and wherein the gas reservoir contains air.

13. The sample holder according to claim 1, wherein the microstructures which form the microstructure array are tapered, and have at least one of a broadly frustoconical shape, and an overhanging shape.

14. The sample holder according to claim 1, wherein the microstructure array extends around the entire top periphery of the sample chamber, and the sample chamber is sealed with respect to outward liquid flow at its top periphery by the hydrophobic surface.

15. The sample holder according to claim 1, wherein the sample holder comprises a fluidic network comprising an inlet, a fluid filling channel and a plurality of sample chambers, wherein the fluid filling channel has a first end and a second end, the first end being connected to the inlet, and wherein the sample chambers are each connected to the fluid filling channel via a respective branch channel of a plurality of branch channels branching off from the fluid filling channel.

16. The sample holder according to claim 15, wherein the microstructure array covers at least a portion of the top periphery of each sample chamber in the fluidic network.

17. The sample holder according to claim 15, wherein the fluidic network comprises a plurality of fluid filling channels, a plurality of separate microstructure arrays is provided, and one of the plurality of separate microstructure arrays serves a respective fluid filling channel.

18. The sample holder according to claim 15, wherein the sample holder comprises a plurality of fluidic networks, a plurality of separate microstructure arrays is provided, and one of the plurality of separate microstructure arrays serves a respective one of the plurality of fluidic networks.

19. The sample holder according to claim 1, wherein the gas reservoir comprises a specific gas or gas mixture, different from air, which is selected so as to provide a particular analysis condition in the sample chamber, and wherein the gas reservoir and the sample chamber are isolated from the atmosphere.

20. The sample holder according to claim 1, comprising an additional reservoir which is connected to a gas channel, via a liquid waste channel and a sub-reservoir, to allow gas to be vented as liquid is introduced into the additional reservoir.

21. The sample holder according to claim 1 comprising a plurality of antimicrobial agents at a plurality of concentrations in different sample chambers, for use in antibiotic susceptibility testing.

22. The sample holder according to claim 15, wherein a single microstructure array is provided, which covers the entire underside of the upper layer, or which has a lobed shape, each lobe overlying one fluidic network or one fluid filling channel.

23. A sample holder comprising:
a sample chamber;
a gas reservoir; and
an upper layer covering over the sample chamber and gas reservoir,
wherein a bottom surface of the upper layer comprises a microstructure array which overlies at least a portion of a top periphery of the sample chamber,
wherein the microstructure array is in communication with a gas path which extends to the gas reservoir, to allow gas exchange between the sample chamber and the gas reservoir,
and wherein the microstructure array overlies at least a portion of the top periphery of the sample chamber at a first position, and overlies at least a portion of a top periphery of the gas reservoir at a second position, and extends between the first position and the second position, such that the gas path is formed by the microstructure array.

24. A sample holder comprising:
a sample chamber;
a gas reservoir; and
an upper layer covering over the sample chamber and gas reservoir,
wherein a bottom surface of the upper layer comprises a microstructure array which overlies at least a portion of a top periphery of the sample chamber,
wherein the microstructure array is in communication with a gas path which extends to the gas reservoir, to allow gas exchange between the sample chamber and the gas reservoir,
wherein the sample holder comprises a middle layer, and the sample chamber is formed as a through-hole in the middle layer,
and wherein the middle layer comprises a raised section, and the upper layer comprises a hole which fits around the raised section of the middle layer, wherein a gap is provided between an outer periphery of the raised section of the middle layer and an inner periphery of the upper layer, and wherein the gap is open to the atmosphere.

25. A sample holder comprising:
a sample chamber;
a gas reservoir; and
an upper layer covering over the sample chamber and gas reservoir,
wherein a bottom surface of the upper layer comprises a microstructure array which overlies at least a portion of a top periphery of the sample chamber,
wherein the microstructure array is in communication with a gas path which extends to the gas reservoir, to allow gas exchange between the sample chamber and the gas reservoir,
and wherein the sample holder comprises an additional reservoir which is connected to a gas channel, via a liquid waste channel and a sub-reservoir, to allow gas to be vented as liquid is introduced into the additional reservoir.

* * * * *